(12) United States Patent
Fridman et al.

(10) Patent No.: US 12,171,640 B2
(45) Date of Patent: Dec. 24, 2024

(54) DEVICE PAIRING FOR DISTRIBUTED INTRAORAL SCANNING SYSTEM

(71) Applicant: Align Technology, Inc., San Jose, CA (US)

(72) Inventors: Edi Fridman, Rishon Le Zion (IL); Adi Levin, Nes Tziona (IL); Abraham Albert Burbea, Tel Aviv (IL); Ofer Sagi, Petach Tikva (IL); Shai Farkash, Hod Hasharon (IL); Ran Katz, Hod Hasharon (IL)

(73) Assignee: Align Technology, Inc., San Jose, CA (US)

( * ) Notice: Subject to any disclaimer, the term of this patent is extended or adjusted under 35 U.S.C. 154(b) by 96 days.

(21) Appl. No.: 17/583,073

(22) Filed: Jan. 24, 2022

(65) Prior Publication Data

US 2022/0233283 A1     Jul. 28, 2022

Related U.S. Application Data

(60) Provisional application No. 63/255,905, filed on Oct. 14, 2021, provisional application No. 63/141,884, filed on Jan. 26, 2021.

(51) Int. Cl.
*A61C 9/00*     (2006.01)
*A61B 1/00*     (2006.01)
(Continued)

(52) U.S. Cl.
CPC ........ *A61C 9/0053* (2013.01); *A61B 1/00016* (2013.01); *A61B 1/00034* (2013.01);
(Continued)

(58) Field of Classification Search
CPC ..... A61C 9/0053; G16H 40/67; H04W 76/11; A61B 1/00059; A61B 5/0088; A61B 90/96; A61B 1/00172; A61B 1/00194
See application file for complete search history.

(56) References Cited

U.S. PATENT DOCUMENTS

| | | | |
|---|---|---|---|
| 6,099,314 | A | 8/2000 | Kopelman et al. |
| 6,334,772 | B1 | 1/2002 | Taub et al. |

(Continued)

FOREIGN PATENT DOCUMENTS

| | | |
|---|---|---|
| WO | 2007084727 A1 | 7/2007 |
| WO | 2020064714 A1 | 4/2020 |
| WO | 2020148041 A1 | 7/2020 |

*Primary Examiner* — Mohamed A. Wasel
(74) *Attorney, Agent, or Firm* — Lowenstein Sandler LLP

(57) ABSTRACT

A first computing device receives a command to associate the first computing device with an intraoral scanner, the command comprising an identifier. The first computing device wirelessly connects with a second computing device, and sends the identifier to the second computing device. The second computing device wirelessly connects to the intraoral scanner and associates the first computing device with the intraoral scanner. Subsequently, intraoral scan data generated by the first intraoral scanner is sent to the second computing device, the intraoral scan data is processed by the second computing device to generate a three-dimensional surface of a dental site, the three-dimensional surface or a view of the three-dimensional surface of the dental site is sent to the first computing device, and the three-dimensional surface or the view of the three-dimensional surface of the dental site is displayed by the first computing device.

25 Claims, 26 Drawing Sheets

(51) Int. Cl.
*A61B 1/24* (2006.01)
*A61B 5/00* (2006.01)
*G16H 40/67* (2018.01)
*H04W 76/11* (2018.01)
*A61B 90/96* (2016.01)

(52) U.S. Cl.
CPC ........ *A61B 1/0004* (2022.02); *A61B 1/00045* (2013.01); *A61B 1/00059* (2013.01); *A61B 1/00172* (2013.01); *A61B 1/00188* (2013.01); *A61B 1/24* (2013.01); *A61B 5/0086* (2013.01); *A61B 5/0088* (2013.01); *A61B 5/7435* (2013.01); *A61B 5/7445* (2013.01); *G16H 40/67* (2018.01); *H04W 76/11* (2018.02); *A61B 90/96* (2016.02)

(56) References Cited

U.S. PATENT DOCUMENTS

| | | | |
|---|---|---|---|
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,319,529 | B2 | 1/2008 | Babayoff |
| 7,373,286 | B2 | 5/2008 | Nikolskiy et al. |
| 7,507,088 | B2 | 3/2009 | Taub et al. |
| 7,545,372 | B2 | 6/2009 | Kopelman et al. |
| 7,609,875 | B2 | 10/2009 | Liu et al. |
| 7,698,068 | B2 | 4/2010 | Babayoff |
| 7,916,911 | B2 | 3/2011 | Kaza et al. |
| 8,108,189 | B2 | 1/2012 | Chelnokov et al. |
| 8,244,028 | B2 | 8/2012 | Kuo et al. |
| 8,587,582 | B2 | 11/2013 | Matov et al. |
| 8,948,482 | B2 | 2/2015 | Levin |
| D742,518 | S | 11/2015 | Barak et al. |
| 9,192,305 | B2 | 11/2015 | Levin |
| 9,261,356 | B2 | 2/2016 | Lampert et al. |
| 9,261,358 | B2 | 2/2016 | Atiya et al. |
| 9,299,192 | B2 | 3/2016 | Kopelman |
| D760,901 | S | 7/2016 | Barak et al. |
| 9,393,087 | B2 | 7/2016 | Moalem |
| 9,408,679 | B2 | 8/2016 | Kopelman |
| 9,431,887 | B2 | 8/2016 | Boltanski |
| 9,439,568 | B2 | 9/2016 | Atiya et al. |
| 9,451,873 | B1 | 9/2016 | Kopelman et al. |
| D768,861 | S | 10/2016 | Barak et al. |
| D771,817 | S | 11/2016 | Barak et al. |
| 9,491,863 | B2 | 11/2016 | Boltanski |
| D774,193 | S | 12/2016 | Makmel et al. |
| 9,510,757 | B2 | 12/2016 | Kopelman et al. |
| 9,660,418 | B2 | 5/2017 | Atiya et al. |
| 9,668,829 | B2 | 6/2017 | Kopelman |
| 9,675,430 | B2 | 6/2017 | Verker et al. |
| 9,693,839 | B2 | 7/2017 | Atiya et al. |
| 9,717,402 | B2 | 8/2017 | Lampert et al. |
| 9,724,177 | B2 | 8/2017 | Levin |
| 9,844,426 | B2 | 12/2017 | Atiya et al. |
| 10,076,389 | B2 | 9/2018 | Wu et al. |
| 10,098,714 | B2 | 10/2018 | Kuo |
| 10,108,269 | B2 | 10/2018 | Sabina et al. |
| 10,111,581 | B2 | 10/2018 | Makmel |
| 10,111,714 | B2 | 10/2018 | Kopelman et al. |
| 10,123,706 | B2 | 11/2018 | Elbaz et al. |
| 10,136,972 | B2 | 11/2018 | Sabina et al. |
| 10,380,212 | B2 | 8/2019 | Elbaz et al. |
| 10,390,913 | B2 | 8/2019 | Sabina et al. |
| 10,453,269 | B2 | 10/2019 | Furst |
| 10,456,043 | B2 | 10/2019 | Atiya et al. |
| 10,499,793 | B2 | 12/2019 | Ozerov et al. |
| 10,504,386 | B2 | 12/2019 | Levin et al. |
| 10,507,087 | B2 | 12/2019 | Elbaz et al. |
| 10,517,482 | B2 | 12/2019 | Sato et al. |
| 10,695,150 | B2 | 6/2020 | Kopelman et al. |
| 10,708,574 | B2 | 7/2020 | Furst et al. |
| 10,772,506 | B2 | 9/2020 | Atiya et al. |
| 10,813,727 | B2 | 10/2020 | Sabina et al. |
| 10,888,399 | B2 | 1/2021 | Kopelman et al. |
| 10,952,816 | B2 | 3/2021 | Kopelman |
| 10,980,613 | B2 | 4/2021 | Shanjani et al. |
| 11,013,581 | B2 | 5/2021 | Sabina et al. |
| D925,739 | S | 7/2021 | Shalev et al. |
| 11,076,146 | B1 | 7/2021 | Fisker et al. |
| 11,096,765 | B2 | 8/2021 | Atiya et al. |
| 11,238,586 | B2 | 2/2022 | Minchenkov et al. |
| 2011/0201944 | A1 | 8/2011 | Higgins et al. |
| 2016/0361553 | A1 | 12/2016 | Kaula et al. |
| 2019/0029784 | A1 | 1/2019 | Moalem et al. |
| 2019/0200903 | A1 | 7/2019 | Watson |
| 2019/0388193 | A1 | 12/2019 | Saphier et al. |
| 2020/0281700 | A1 | 9/2020 | Kopelman et al. |
| 2020/0281701 | A1* | 9/2020 | Kim ............ A61B 8/085 |
| 2020/0281702 | A1 | 9/2020 | Kopelman et al. |
| 2020/0315434 | A1* | 10/2020 | Kopelman ......... A61B 1/00103 |
| 2020/0349705 | A1 | 11/2020 | Minchenkov et al. |
| 2020/0404243 | A1 | 12/2020 | Saphier et al. |
| 2021/0030503 | A1 | 2/2021 | Shalev et al. |
| 2021/0059796 | A1 | 3/2021 | Weiss et al. |
| 2021/0068773 | A1 | 3/2021 | Moshe et al. |
| 2021/0121049 | A1 | 4/2021 | Rudnitsky et al. |
| 2021/0128281 | A1 | 5/2021 | Peleg |
| 2021/0137653 | A1 | 5/2021 | Saphier et al. |
| 2021/0196152 | A1 | 7/2021 | Saphier et al. |
| 2021/0212806 | A1* | 7/2021 | Sorimoto ........... A61B 1/00096 |
| 2021/0298874 | A1* | 9/2021 | Katzman ............ G16H 10/60 |
| 2023/0000600 | A1 | 1/2023 | Wong et al. |
| 2023/0031392 | A1 | 2/2023 | Lo Russo |

* cited by examiner

DEVICE PAIRING FOR DISTRIBUTED INTRAORAL SCANNING SYSTEM

RELATED APPLICATIONS

This patent application claims the benefit under 35 U.S.C. § 119 (e) of U.S. Provisional Application No. 63/255,905 filed Oct. 14, 2021, and also claims benefit under 35 U.S.C. § 119 (e) of U.S. Provisional Application No. 63/141,884 filed Jan. 26, 2021, both of which are incorporated by reference herein. This patent application is also related to U.S. patent application Ser. No. 17/583,071 filed Jan. 24, 2022 titled "Distributed Intraoral Scanning System," and is also related to U.S. patent application Ser. No. 17/583,074 filed Jan. 24, 2022 titled "Wireless Intraoral Scanner for Distributed Intraoral Scanning System", both of which are incorporated by reference herein.

TECHNICAL FIELD

Embodiments of the present disclosure relate to the field of dentistry and, in particular, to a distributed intraoral scanning system that includes one or more components (e.g., intraoral scanners and/or computing devices) that are connected via a wireless connection. Embodiments also relate to wireless intraoral scanners.

BACKGROUND

Intraoral scanning systems generally include a handheld intraoral scanner and a computing device connected to the handheld intraoral scanner via a wired connection. The wired connection provides power to the intraoral scanner and via the wired connection the computing device receives intraoral scan data from the handheld intraoral scanner. The computing device processes the intraoral scan data and outputs a result of the processing to a display that is either part of the computing device or that is connected to the computing device via a wired connection.

Intraoral scanning systems are expensive and take up space in a dental office. Accordingly, it is often unfeasible for dentist offices to invest in multiple intraoral scanning systems. This limits the number of intraoral scans that a dental office can perform. Additionally, the dentist needs to move around the entire intraoral scanning system to different rooms or needs to dedicate a single room for intraoral scanning.

SUMMARY

In a first aspect of the disclosure, an intraoral scanning system comprises a first intraoral scanner, a second intraoral scanner, and a first computing device wirelessly connected to both the first intraoral scanner and the second intraoral scanner. The first computing device is to: receive first intraoral scan data from the first intraoral scanner; generate a first three-dimensional (3D) surface of at least a portion of a first patient's dental arch based on the first intraoral scan data; receive second intraoral scan data from the second intraoral scanner; and generate a second 3D surface of at least a portion of a second patient's dental arch based on the second intraoral scan data.

A second aspect of the disclosure may further extend the first aspect of the disclosure. In the second aspect of the disclosure, the intraoral scanning system further comprises a first display or a second computing device wirelessly connected to the first computing device. The first computing device is further to: determine that a view of the first 3D surface of at least the portion of the first patient's dental arch is to be output to the first display or the second computing device; and output the view of the first 3D surface of at least the portion of the first patient's dental arch to the first display or the second computing device.

A third aspect of the disclosure may further extend the second aspect of the disclosure. In the third aspect of the disclosure, the intraoral scanning system further comprises a second display or a third computing device wirelessly connected to the first computing device. The first computing device is further to: determine that a view of the second 3D surface of at least the portion of the second patient's dental arch is to be output to the second display or the third computing device; and output the view of the second 3D surface of at least the portion of the second patient's dental arch to the second display or the third computing device.

A fourth aspect of the disclosure may further extend the second or third aspect of the disclosure. In the fourth aspect of the disclosure, the second computing device is wirelessly connected to the first computing device. Additionally, the computing device is further to: receive a command to manipulate the view of the first 3D surface of at least the portion of the first patient's dental arch from the second computing device; and manipulate the view of the first 3D surface of at least the portion of the first patient's dental arch based on the received command.

A fifth aspect of the disclosure may further extend any of the first through fourth aspects of the disclosure. In the fifth aspect of the disclosure, the first computing device is wirelessly connected to the first intraoral scanner and to the second intraoral scanner via a wireless network.

A sixth aspect of the disclosure may further extend any of the first through fifth aspects of the disclosure. In the sixth aspect of the disclosure, the first intraoral scanner is to compress the first intraoral scan data before sending the first intraoral scan data to the first computing device, and the first computing device is to decompress the first intraoral scan data before generating the first 3D surface of at least the portion of the first patient's dental arch.

A seventh aspect of the disclosure may further extend any of the first through sixth aspects of the disclosure. In the seventh aspect of the disclosure, the first intraoral scanner is further to generate and compress at least one of a) one or more color images or b) one or more near-infrared images. Additionally, the first computing device is further to: receive at least one of a) the one or more color images or b) the one or more near-infrared images; and decompress at least one of a) the one or more color images or b) the one or more near-infrared images.

An eighth aspect of the disclosure may further extend any of the first through seventh aspects of the disclosure. In the eighth aspect of the disclosure, the first intraoral scan data comprises a first plurality of intraoral scans received during a first intraoral scanning session, and the first computing device is further to: continually update the first 3D surface of at least the portion of the first patient's dental arch as further intraoral scans of the first plurality of intraoral scans are received; and stream updates to the view of the first 3D surface of at least the portion of the first patient's dental arch as the first 3D surface of the first patient's dental arch is updated.

A ninth aspect of the disclosure may further extend any of the first through eighth aspects of the disclosure. In the ninth aspect of the disclosure, the intraoral scanning system further comprises a plurality of cradles configured to hold at least one of the first intraoral scanner or the second intraoral scanner, each of the plurality of cradles to periodically broadcast a distinct identifier. Additionally, the first intraoral scanner is to: detect a distinct identifier broadcast by a cradle closest to the first intraoral scanner; and send the distinct identifier broadcast by the cradle closest to the first intraoral scanner to the first computing device. Additionally, the first computing device is to determine a location of the first intraoral scanner based on the distinct identifier received from the first intraoral scanner.

A tenth aspect of the disclosure may further extend any of the first through ninth aspects of the disclosure. In the tenth aspect of the disclosure, the plurality of cradles comprises a plurality of charging stations for at least one of the first intraoral scanner or the second intraoral scanner.

An eleventh aspect of the disclosure may further extend any of the first through tenth aspects of the disclosure. In the eleventh aspect of the disclosure, the first computing device comprises: a base comprising an access point and power port for connecting the first computing device to a power source; a plurality of adaptors, each adaptor of the plurality of adaptors comprising a power supply, a switch connecting the adaptor to the access point, and a power connector connecting the power supply to the power port; and one or more compute units, each compute unit of the one or more compute units removably coupled to an adaptor of the plurality of adaptors.

A twelfth aspect of the disclosure may further extend the eleventh aspect of the disclosure. In the twelfth aspect of the disclosure, for each compute unit of the one or more compute units, a single connector connects that compute unit to the adaptor, and wherein the compute unit is removable from the adaptor via a single action, and is insertable into an alternate adaptor of an alternate computing device via a single action.

A thirteenth aspect of the disclosure may further extend the eleventh aspect of the disclosure. In the thirteenth aspect of the disclosure, the one or more compute units comprise: a first compute unit associated with the first intraoral scanner, wherein the first compute unit is to process the first intraoral scan data from the first intraoral scanner; and a second compute unit associated with the second intraoral scanner, wherein the second compute unit is to process second intraoral scan data from the second intraoral scanner.

A fourteenth aspect of the disclosure may further extend the thirteenth aspect of the disclosure. In the fourteenth aspect of the disclosure, the intraoral scanning system further comprises: a first display to receive first image data from the first compute unit and to display the first image data; and a second display to receive second image data from the second compute unit and to display the second image data.

A fifteenth aspect of the disclosure may further extend the thirteenth aspect of the disclosure. In the fifteenth aspect of the disclosure, the intraoral scanning system further comprises: a second computing device wirelessly connected to the first computing device, the second computing device to control a first instance of an intraoral scan application executing on the first compute unit; and a third computing device wirelessly connected to the first computing device, the third computing device to control a second instance of an intraoral scan application executing on the second compute unit.

A sixteenth aspect of the disclosure may further extend any of the first through fifteenth aspects of the disclosure. In the sixteenth aspect of the disclosure, the intraoral scanning system further comprises a second computing device wirelessly connected to the first computing device. The first computing device is to operate in a slave mode and the second computing device is to operate in a master mode; and the first computing device is to perform one or more operations associated with at least one of dental diagnostics or orthodontic treatment responsive to commands from the second computing device and to output results of the one or more operations to the second computing device.

In a seventeenth aspect of the disclosure, an intraoral scanning system comprises a first intraoral scanner, at least one of a first computing device or a first display, and a second computing device wirelessly connected to the first intraoral scanner and operatively connected to at least one of the first computing device or the first display via a wireless network. The second computing device is to: receive first intraoral scan data from the first intraoral scanner; send the first intraoral scan data to a third computing device that is outside of the local area network; receive, from the third computing device, a first three-dimensional (3D) surface of at least a portion of a first patient's dental arch that was generated by the third computing device based on the first intraoral scan data; and send a view of the first 3D surface of at least the portion of the first patient's dental arch to at least one of the first computing device or the first display.

An eighteenth aspect of the disclosure may further extend the seventeenth aspect of the disclosure. In the eighteenth aspect of the disclosure, the second computing device is further to: receive at least one of a) one or more color images or b) one or more near-infrared images from the first intraoral scanner; and send at least one of a) the one or more color images or b) the one or more near-infrared images from the first intraoral scanner to the third computing device that is outside of the local area network. The first 3D surface received from the third computing device is augmented by information from at least one of a) the one or more color images or b) the one or more near-infrared images.

A nineteenth aspect of the disclosure may further extend seventeenth or eighteenth aspect of the disclosure. In the nineteenth aspect of the disclosure, the second computing device is to: determine that a view of the first 3D surface of at least the portion of the first patient's dental arch is to be output to the first display or the first computing device; and output the view of the first 3D surface of at least the portion of the first patient's dental arch to the first display or the first computing device.

A twentieth aspect of the disclosure may further extend any of the seventeenth through nineteenth aspects of the disclosure. In the twentieth aspect of the disclosure, the second computing device is further to: receive a command to manipulate the view of the first 3D surface of at least the portion of the first patient's dental arch from the first computing device; send the command to the third computing device; and receive a manipulated the view of the first 3D surface of at least the portion of the first patient's dental arch from the third computing device.

A twenty-first aspect of the disclosure may further extend any of the seventeenth through twentieth aspects of the disclosure. In the twenty-first aspect of the disclosure, the first intraoral scanner is to compress the first intraoral scan data before sending the first intraoral scan data to the second computing device, and the second computing device is to send the compressed first intraoral scan data to the third computing device.

A twenty-second aspect of the disclosure may further extend any of the seventeenth through twenty-first aspects of the disclosure. In the twenty-second aspect of the disclosure, the first intraoral scan data comprises a first plurality of intraoral scans received during a first intraoral scanning session. Additionally, the second computing device is further to: receive the first plurality of intraoral scans in sequence; send the first plurality of intraoral scans in sequence to the third computing device; receive a stream of updates to the first 3D surface of at least the portion of the first patient's dental arch as further intraoral scans of the first plurality of intraoral scans are processed by the third computing device; and stream updates to the view of the first 3D surface of at least the portion of the first patient's dental arch to the first computing device or the first display.

A twenty-third aspect of the disclosure may further extend any of the seventeenth through twenty-second aspects of the disclosure. In the twenty-third aspect of the disclosure, the intraoral scanning system further comprises a plurality of cradles configured to hold at least one of the first intraoral scanner or a second intraoral scanner, each of the plurality of cradles to periodically broadcast a distinct identifier. Additionally, the first intraoral scanner is to: detect a distinct identifier broadcast by a cradle closest to the first intraoral scanner; and send the distinct identifier broadcast by the cradle closest to the first intraoral scanner to the second computing device. The second computing device is further to determine a location of the first intraoral scanner based on the distinct identifier received from the first intraoral scanner.

In a twenty-fourth aspect of the disclosure, an intraoral scanning system comprises an intraoral scanner, at least one of a first computing device or a first display, and a second computing device wirelessly connected to the intraoral scanner and operatively connected to at least one of the first computing device or the first display via a wireless network. The second computing device is to: receive intraoral scan data from the intraoral scanner; generate a first three-dimensional (3D) surface of at least a portion of a first patient's dental arch based on the intraoral scan data; and send a view of the first 3D surface of at least the portion of first patient's dental arch to at least one of the first computing device or the first display.

A twenty-fifth aspect of the disclosure may further extend the twenty-fourth aspect of the disclosure. In the twenty-fifth aspect of the disclosure, at least one of the first computing device or the first display is to send a command to the second computing device that causes the second computing device to send the view of the first 3D surface to at least one of the first computing device or the first display.

A twenty-sixth aspect of the disclosure may further extend the twenty-fourth or twenty-fifth aspects of the disclosure. In the twenty-sixth aspect of the disclosure, the second computing device is further to: determine that a view of the first 3D surface of at least the portion of the first patient's dental arch is to be output to the first display or the first computing device; and output the view of the first 3D surface of at least the portion of the first patient's dental arch to the first display or the first computing device.

A twenty-seventh aspect of the disclosure may further extend any of the twenty-fourth through twenty-sixth aspects of the disclosure. In the twenty-seventh aspect of the disclosure, the second computing device is further to: receive a command to manipulate the view of the first 3D surface of at least the portion of the first patient's dental arch from the first computing device; and manipulate the view of the first 3D surface of at least the portion of the first patient's dental arch based on the received command.

A twenty-eighth aspect of the disclosure may further extend any of the twenty-fourth through twenty-seventh aspects of the disclosure. In the twenty-eighth aspect of the disclosure, the intraoral scanner is to compress the intraoral scan data before sending the intraoral scan data to the second computing device, and the second computing device is to decompress the intraoral scan data before generating the first 3D surface of at least the portion of the first patient's dental arch.

A twenty-ninth aspect of the disclosure may further extend the twenty-eighth aspect of the disclosure. In the twenty-ninth aspect of the disclosure, the intraoral scanner is further to generate and compress at least one of a) one or more color images or b) one or more near-infrared images. Additionally, the second computing device is further to: receive at least one of a) the one or more color images or b) the one or more near-infrared images; and decompress at least one of a) the one or more color images or b) the one or more near-infrared images.

A thirtieth aspect of the disclosure may further extend any of the twenty-fourth through twenty-ninth aspects of the disclosure. In the thirtieth aspect of the disclosure, the intraoral scan data comprises a first plurality of intraoral scans received during an intraoral scanning session. Additionally, the second computing device is further to: continually update the first 3D surface of at least the portion of the first patient's dental arch as further intraoral scans of the first plurality of intraoral scans are received; and stream updates to the view of the first 3D surface of at least the portion of the first patient's dental arch as the first 3D surface of the first patient's dental arch is updated.

A thirty-first aspect of the disclosure may further extend any of the twenty-fourth through thirtieth aspects of the disclosure. In the thirty-first aspect of the disclosure, the intraoral scanning system further comprises a plurality of cradles configured to hold the intraoral scanner, each of the plurality of cradles to periodically broadcast a distinct identifier. Additionally, the intraoral scanner is to: detect a distinct identifier broadcast by a cradle closest to the intraoral scanner; and send the distinct identifier broadcast by the cradle closest to the intraoral scanner to the second computing device; wherein the second computing device is to determine a location of the intraoral scanner based on the distinct identifier received from the intraoral scanner.

A thirty-second aspect of the disclosure may further extend the thirty-first aspect of the disclosure. In the thirty-second aspect of the disclosure, the plurality of cradles comprises a plurality of charging stations for at least one of the intraoral scanner or the second intraoral scanner.

A thirty-third aspect of the disclosure may further extend any of the twenty-fourth through thirty-second aspects of the disclosure. In the thirty-third aspect of the disclosure, the second computing device comprises: a base comprising an access point and power port for connecting the first computing device to a power source; a plurality of adaptors, each adaptor of the plurality of adaptors comprising a power supply, a switch connecting the adaptor to the access point, and a power connector connecting the power supply to the power port; and one or more compute units, each compute unit of the one or more compute units removably coupled to an adaptor of the plurality of adaptors.

A thirty-fourth aspect of the disclosure may further extend any of the twenty-fourth through thirty-third aspects of the disclosure. In the thirty-fourth aspect of the disclosure, the first computing device is to control an intraoral scan application executing on the first compute unit.

A thirty-fifth aspect of the disclosure may further extend any of the twenty-fourth through thirty-fourth aspects of the disclosure. In the thirty-fifth aspect of the disclosure, the second computing device is to operate in a slave mode and the first computing device is to operate in a master mode;

and the second computing device is to perform one or more operations associated with at least one of dental diagnostics or orthodontic treatment responsive to commands from the first computing device and to output results of the one or more operations to the first computing device.

In a 36th aspect of the disclosure, a method comprises: receiving, by a first computing device, a user command to associate the first computing device with a first intraoral scanner of a plurality of intraoral scanners, the request comprising an identifier of the first intraoral scanner; wirelessly connecting the first computing device with a second computing device; and sending the identifier of the first intraoral scanner to the second computing device, wherein the second computing device wirelessly connects to the first intraoral scanner and associates the first computing device with the first intraoral scanner; wherein once the first computing device and the first intraoral scanner are both wirelessly connected to the second computing device and associated with one another, intraoral scan data generated by the first intraoral scanner is sent to the second computing device, the intraoral scan data is processed by the second computing device to generate a three-dimensional surface of a dental site, the three-dimensional surface or a view of the three-dimensional surface of the dental site is sent to the first computing device, and the three-dimensional surface or the view of the three-dimensional surface of the dental site is displayed by the first computing device.

A 37th aspect of the disclosure may further extend the 36th aspect of the disclosure. In the 37th aspect of the disclosure, the method further comprises: determining, by the first computing device, an available compute unit from a plurality of compute units of the second computing device, wherein wirelessly connecting the first computing device with the second computing device comprises wirelessly connecting the first computing device to the available compute unit of the second computing device.

A 38th aspect of the disclosure may further extend the 36th or 37th aspect of the disclosure. In the 38th aspect of the disclosure, the method further comprises: receiving, by the first computing device or by the first intraoral scanner, an identifier of a first display device; and sending, by the first computing device or by the first intraoral scanner, the identifier of the first display device to the second computing device, wherein the second computing device wirelessly connects to the first display device and associates the first display device with the first computing device and the first intraoral scanner, and wherein the view of the three-dimensional surface of the dental site is additionally sent to the first display device and displayed by the first display device.

A 39th aspect of the disclosure may further extend the 38th aspect of the disclosure. In the 39th aspect of the disclosure, the identifier of the first display device comprises a code, wherein the first display device displays the code, and wherein receiving the identifier of the first display device by the first intraoral scanner comprises scanning the code by the first intraoral scanner.

A 40th aspect of the disclosure may further extend the 39th aspect of the disclosure. In the 40th aspect of the disclosure, the code comprises a one-dimensional barcode or a two-dimensional barcode.

A 41st aspect of the disclosure may further extend the 38th aspect of the disclosure. In the 41st aspect of the disclosure, the first intraoral scanner comprises a touchscreen, the method further comprising: outputting a touch keypad on the touchscreen of the first intraoral scanner; wherein receiving the identifier of the first display device by the first intraoral scanner comprises receiving the identifier of the first display device via the touch keypad.

A 42nd aspect of the disclosure may further extend any of the 36th through 41st aspects of the disclosure. In the 42nd aspect of the disclosure, the method further comprises: receiving a user command to disconnect the first computing device and the first intraoral scanner from the second computing device; wirelessly sending a disconnect instruction from the first computing device to the second computing device; receiving a disconnect confirmation by the first computing device from the second computing device; and displaying the disconnect confirmation on at least one of the display of the first computing device or a touchscreen of the first intraoral scanner.

In a 43rd aspect of the disclosure, an intraoral scanner comprises: a body; a probe at one end of the body, the probe comprising a scanner head; a wireless communication module disposed within the body; one or more optical sensor to receive light that enters the scanner head and generate intraoral scan data based on the light, wherein the wireless communication module is to wirelessly send the intraoral scan data to a first computing device; and a touchscreen, disposed on the body and configured to: output a plurality of virtual buttons; detect a touch input associated with a virtual button of the plurality of virtual buttons; and provide a signal associated with the touch input of the virtual button to the first computing device.

A 44th aspect of the disclosure may further extend the 43rd aspect of the disclosure. In the 44th aspect of the disclosure, the intraoral scanner is to receive an input from the first computing device indicating a current mode of an intraoral scan application; and determine the plurality of virtual buttons to output on the touchscreen based at least in part on the current mode of the intraoral scan application.

A 45th aspect of the disclosure may further extend the 44th aspect of the disclosure. In the 45th aspect of the disclosure, while the current mode is a scanning mode, the plurality of virtual buttons comprise at least one of a next segment button or a previous segment button.

A 46th aspect of the disclosure may further extend the 44th aspect of the disclosure. In the 46th aspect of the disclosure, while the current mode is a scanning mode, the plurality of virtual buttons comprise a lower dental arch segment button, an upper dental arch segment button, and a bite segment button.

A 47th aspect of the disclosure may further extend the 44th aspect of the disclosure. In the 47th aspect of the disclosure, while the current mode is a three-dimensional surface viewing mode, the plurality of buttons comprise a rotate button, a pan button, and a zoom button.

A 48th aspect of the disclosure may further extend any of the 43rd through 47th aspects of the disclosure. In the 48th aspect of the disclosure, the touchscreen supports multi-touch control, and wherein: dragging of a first number of fingers of a user across the touchscreen causes rotation of a three-dimensional surface on a display; dragging of a second number of fingers of the user across the touchscreen causes panning of the three-dimensional surface on the display; an inward pinching motion of a user's fingers on the touchscreen causes zooming out of the three-dimensional surface on the display; and an outward pinching motion of the user's fingers on the touchscreen causes zooming in of the three-dimensional surface on the display.

A 49th aspect of the disclosure may further extend any of the 43rd through 48th aspects of the disclosure. In the 49th aspect of the disclosure, the touchscreen is to output one or more message button responsive to receipt of a confirmation request message from the first computing device, wherein the one or more message button comprises at least one of a confirm button or a cancel button.

In a 50th aspect of the disclosure, an intraoral scanning system comprises: a first intraoral scanner configured to generate intraoral scan data; a first computing device configured to control an intraoral scan application; and a second computing device configured to execute the intraoral scan application, wherein the second computing device is further configured to: receive a first connection request from the first computing device; wirelessly connect to the first computing device; receive an identifier of the first intraoral scanner from the first computing device; wirelessly connect to the first intraoral scanner using the identifier; and associate the first intraoral scanner with the first computing device.

A 51st aspect of the disclosure may further extend the 50th aspect of the disclosure. In the 51st aspect of the disclosure, once the first computing device is associated with the first intraoral scanner and the first intraoral scanner and first computing device are both wirelessly connected to the second computing device: the first intraoral scanner is to send the intraoral scan data to the second computing device; the intraoral scan application of the second computing device is to process the intraoral scan data to generate or update a three-dimensional surface of a dental site and send a view of the three-dimensional surface to the first computing device; and the first computing device is to output the view of the three-dimensional surface of the dental site to a display of the first computing device.

A 52nd aspect of the disclosure may further extend the 50th or 51st aspect of the disclosure. In the 52nd aspect of the disclosure, the first computing device is one of a plurality of peripheral computing devices of the intraoral scanning system, the first intraoral scanner is one of a plurality of intraoral scanners of the intraoral scanning system, and the second computing device is a server computing device of the intraoral scanning system, the intraoral scanning system further comprising: a second intraoral scanner of the plurality of intraoral scanners; and a third computing device of the plurality of peripheral computing devices; wherein the second computing device is further to: receive a second connection request from the third computing device; wirelessly connect to the third computing device; receive a second identifier of the second intraoral scanner from the third computing device; wirelessly connect to the second intraoral scanner using the second identifier; and associate the second intraoral scanner with the third computing device.

A 53rd aspect of the disclosure may further extend the 52nd aspect of the disclosure. In the 53rd aspect of the disclosure, the second computing device comprises a plurality of compute units, wherein the first computing device and the first intraoral scanner are to connect to a first available compute unit of the plurality of compute units, and wherein the third computing device and the second intraoral scanner are to connect to a second available compute unit of the plurality of compute units.

A 54th aspect of the disclosure may further extend any of the 50th through 53rd aspects of the disclosure. In the 54th aspect of the disclosure, the second computing device comprises a plurality of compute units, and wherein the first computing device is to: determine an available compute unit of the plurality of compute units; and wirelessly connect to the available compute unit.

A 55th aspect of the disclosure may further extend any of the 50th through 54th aspects of the disclosure. In the 55th aspect of the disclosure, the intraoral scanning system further comprises: a display device; wherein the display device is to display an identifier of the display device; wherein the first computing device or the intraoral scanner is to receive the identifier of the display device and send the identifier of the display device to the second computing device; and wherein the second computing device is to wirelessly connect to the display device using the identifier and associate the display device with the first computing device and the first intraoral scanner.

A 56th aspect of the disclosure may further extend the 55th aspect of the disclosure. In the 56th aspect of the disclosure, the first intraoral scanner comprises a touchscreen that is to output a touch keypad; and the first intraoral scanner is to receive user input of the identifier of the display device via the touch keypad, wherein the identifier comprises a code.

A 57th aspect of the disclosure may further extend the 55th or 56th aspect of the disclosure. In the 57th aspect of the disclosure, once the first computing device, the first intraoral scanner and the display device are associated with one another and wirelessly connected to the second computing device: the first intraoral scanner is to send the intraoral scan data to the second computing device; the intraoral scan application of the second computing device is to process the intraoral scan data to generate or update a three-dimensional surface of a dental site and send a view of the three-dimensional surface to the first computing device and to the display device; the first computing device is to output the view of the three-dimensional surface of the dental site to a display of the first computing device; and the display device is to output the view of the three-dimensional surface of the dental site.

A 58th aspect of the disclosure may further extend any of the 55th through 57th aspects of the disclosure. In the 58th aspect of the disclosure, the first intraoral scanner is to scan the identifier and send the identifier to the second computing device.

A 59th aspect of the disclosure may further extend the 58th aspect of the disclosure. In the 59th aspect of the disclosure, the identifier comprises a one-dimensional barcode or a two-dimensional barcode.

A 60th aspect of the disclosure may further extend any of the 50th through 59th aspects of the disclosure. In the 60th aspect of the disclosure, the first intraoral scanner comprises a touchpad configured to output a plurality of virtual buttons and detect a touch input associated with a virtual button of the plurality of virtual buttons; and the first intraoral scanner is configured to provide a signal associated with the touch input of the virtual button to the second computing device.

A 61st aspect of the disclosure may further extend the 60th aspect of the disclosure. In the 61st aspect of the disclosure, the plurality of buttons output by the first intraoral scanner is based on a current mode of the intraoral scan application.

A 62nd aspect of the disclosure may further extend the 61st aspect of the disclosure. In the 62nd aspect of the disclosure, the first intraoral scanner is to receive an input from the second computing device indicating the current mode of an intraoral scan application; and determine the plurality of virtual buttons to output on the touchscreen based at least in part on the current mode of the intraoral scan application.

A 63rd aspect of the disclosure may further extend any of the 60th through 62nd aspects of the disclosure. In the 63rd aspect of the disclosure, while the current mode is a scanning mode, the plurality of virtual buttons output by the touchscreen comprise at least one of a next segment button or a previous segment button.

A 64th aspect of the disclosure may further extend any of the 60th through 63rd aspects of the disclosure. In the 64th aspect of the disclosure, while the current mode is a scanning mode, the plurality of virtual buttons output by the touchscreen comprise a lower dental arch segment button, an upper dental arch segment button, and a bite segment button.

A 65th aspect of the disclosure may further extend any of the 60th through 64th aspects of the disclosure. In the 65th aspect of the disclosure, while the current mode is a three-dimensional surface viewing mode, the plurality of buttons comprise a rotate button, a pan button, and a zoom button.

A 66th aspect of the disclosure may further extend any of the 60th through 65th aspects of the disclosure. In the 66th aspect of the disclosure, the touchscreen is to output one or more message button responsive to receipt of a confirmation request message from the second computing device, wherein the one or more message button comprises at least one of a confirm button or a cancel button.

A 67th aspect of the disclosure may further extend any of the 50th through 66th aspects of the disclosure. In the 67th aspect of the disclosure, the first intraoral scanner comprises a touchscreen that is configured to display the identifier of the first intraoral scanner.

In a 68th aspect of the disclosure, an intraoral scanning system comprises: a plurality of intraoral scanners, the plurality of intraoral scanners including a first number of intraoral scanners; and a first computing device wirelessly connected to the plurality of intraoral scanners via a wireless network, wherein at least one of first computing device or one or more of the plurality of intraoral scanners is to: monitor conditions of the wireless network; determine a second number of intraoral scanners supported by the wireless network according to the conditions of the wireless network; determine whether the first number of intraoral scanners is equal to or less than the second number of intraoral scanners; and output a notice based on whether the first number of intraoral scanners is equal to or less than the second number of intraoral scanners.

A 69th aspect of the disclosure may further extend the 68th aspect of the disclosure. In the 69th aspect of the disclosure, at least one of first computing device or one or more of the plurality of intraoral scanners is further to determine that the first number of intraoral scanners exceeds the second number of intraoral scanners, wherein the notice is a recommendation to use one or more of the plurality of intraoral scanners in a wired configuration.

A 70th aspect of the disclosure may further extend the 68th or 69th aspects of the disclosure. In the 70th aspect of the disclosure, at least one of first computing device or one or more of the plurality of intraoral scanners is further to determine that the first number of intraoral scanners exceeds the second number of intraoral scanners, wherein the notice is a recommendation to update the wireless network so that the wireless network will support more intraoral scanners.

A 71st aspect of the disclosure may further extend the 68th through 70th aspects of the disclosure. In the 71st aspect of the disclosure, at least one of first computing device or one or more of the plurality of intraoral scanners is further to determine that the first number of intraoral scanners is equal to or less than the second number of intraoral scanners, wherein the notice is an indication that the wireless network is sufficient to accommodate the plurality of intraoral scanners.

In a 72nd aspect of the disclosure, an intraoral scanning system comprises: an intraoral scanner comprising: a rechargeable battery; a charging module; a wireless communication module; a wired communication module; and a port connected to the wired communication module and the charging module; and a cable coupled to the port, wherein the cable is to provide power to the charging module while the intraoral scanner is not in use; wherein at least one of the intraoral scanner or the cable is to: detect when the intraoral scanner is in use; and prevent the cable from supplying power to the charging module while the intraoral scanner is in use.

A 73rd aspect of the disclosure may further extend the 72nd aspect of the disclosure. In the 73rd aspect of the disclosure the intraoral scanning system further comprises a cradle, wherein at least one of the intraoral scanner or the cable is to: detect when the intraoral scanner is in the cradle; and enable the cable to supply power to the charging module while the intraoral scanner is in the cradle.

A 74th aspect of the disclosure may further extend the 73rd aspect of the disclosure. In the 74th aspect of the disclosure, at least one of the intraoral scanning system or the cable includes a switch that has a closed state while the intraoral scanner is in the cradle and an open state while the intraoral scanner is removed from the cradle.

A 75th aspect of the disclosure may further extend the 74th aspect of the disclosure. In the 75th aspect of the disclosure, the switch is a magnetic switch, wherein the cradle comprises one or more magnets that provide a magnetic field, and wherein the magnetic field causes the magnetic switch to have the closed state while the intraoral scanner is in the cradle.

A 76th aspect of the disclosure may further extend the 74th or 75th aspects of the disclosure. In the 76th aspect of the disclosure, the intraoral scanner further comprises: a motion sensor to detect a motion state of the intraoral scanner; and a controller to determine whether the intraoral scanner is in use based on an analysis of the motion state.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1A:
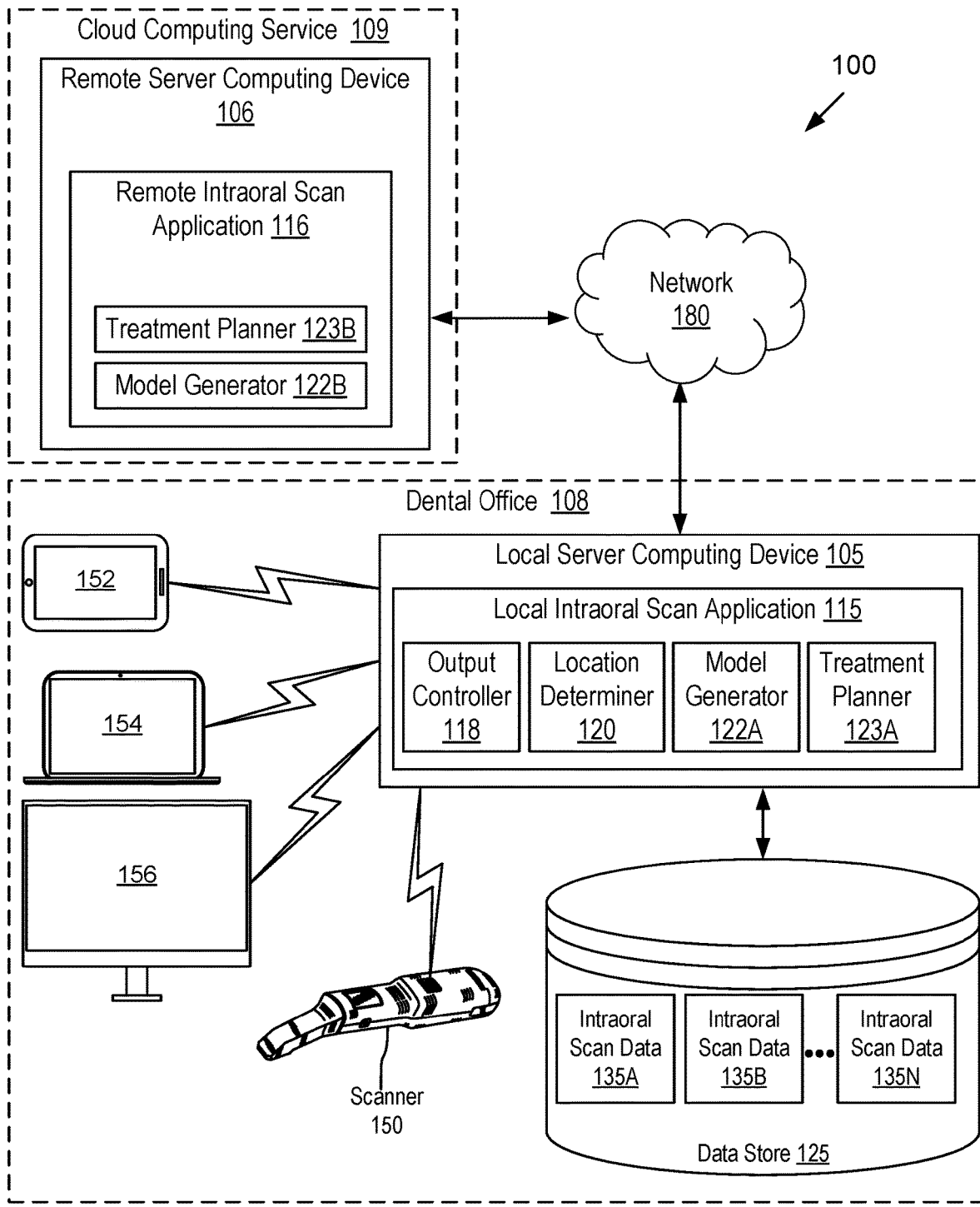
FIG. 1A illustrates a distributed system for performing intraoral scanning and/or generating a virtual three-dimensional model of an intraoral site, in accordance with an embodiment.

Described herein are embodiments of a distributed intraoral scanning system. In embodiments, the distributed intraoral scanning system includes one or more handheld intraoral scanners wirelessly connected to a local server computing device that includes an intraoral scan application, and one or more displays and/or additional computing devices (also referred to as peripheral computing devices or control computing devices) operatively connected to the local server computing device via wired or wireless connections. Each handheld intraoral scanner is configured to scan a patient's oral cavity, and to wirelessly transmit intraoral scan data to the local server computing device. The local server computing device then processes the intraoral scan data or may send the intraoral scan data to a remote server computing device to be processed. In either case, the local server computing device obtains (e.g., generates or receives) a three-dimensional (3D) surface of the patient's oral cavity. The local server computing device then outputs the 3D surface (or a view of the 3D surface) to a display and/or additional computing device operatively connected to the local server computing device. The handheld intraoral scanner, the server computing device, the one or more displays, and the one or more additional computing device (e.g., such as mobile computing devices) may be separate and distinct. The processing resources for processing intraoral scan data may be separate from the scanner that generates the intraoral scan data, and may further be separate from the devices that control the intraoral scan application and the displays that provide a visualization of the scan data and/or of a 3D surface generated from the scan data. Accordingly, displays, additional computing devices and/or intraoral scanners may be added to or removed from the scanning system based on the needs of a dentist office. In embodiments, the local server computing device that runs a local intraoral scan application manages and coordinates between multiple intraoral scanners and multiple displays and/or additional computing devices (e.g., peripheral computing devices) in a seamless manner.

In embodiments, each handheld intraoral scanner wirelessly connected to the local server computing device may send intraoral scan data to the local server computing device. The local server computing device may process the intraoral scan data from multiple intraoral scanners in parallel, and may send the respective outputs of the processing (e.g., views of a 3D surface of respective patient intraoral cavities) to different displays and/or computing devices.

In an example, a first dentist in a first room of a dentist office may scan a first patient's oral cavity using a first intraoral scanner, the first intraoral scanner may send first intraoral scan data to the server computing device in a second room, and a first display and/or first mobile computing device in the first room may receive an up-to-date 3D surface (or a view such as a 2D view or 3D view of the up-to-date 3D surface) of a region of the first patient's oral cavity that has been scanned during the scanning process. Thus, the first dentist may view the progress of the intraoral scan operation as the intraoral scan is being performed. Once the scan is complete, the server computing device may generate a digital 3D model of one or more dental arch of the patient, and may perform one or more treatment planning operations based on the digital 3D model. The first mobile computing device may provide an interface for viewing and manipulating the digital 3D model and/or for controlling the one or more treatment planning operations that are performed on the server computing device.

At the same time or at a different time, a second dentist in a third room of the dentist office may scan a second patient's oral cavity using a second intraoral scanner, the second intraoral scanner may send second intraoral scan data to the server computing device in the second room, and a second display and/or second mobile computing device in the third room may receive an up-to-date 3D surface of a region of the second patient's oral cavity that has been scanned during the scanning process. Thus, the second dentist may view the progress of the intraoral scan operation as the intraoral scan is being performed. Once the scan is complete, the server computing device may generate a digital 3D model of one or more dental arch of the second patient, and may perform one or more treatment planning operations based on the digital 3D model. The second mobile computing device may provide an interface for viewing and manipulating the digital 3D model and/or for controlling the one or more treatment planning operations that are performed on the server computing device.

Embodiments described herein eliminate a need for a dentist to move an entire intraoral scanning system between rooms of a dental office, and reduce the overall cost of ownership for an intraoral scanning system. The handheld intraoral scanners may be small and compact as compared to an entire intraoral scanning system, and may be easily carried between rooms and stations while the displays and server computing device may remain stationary in designated locations. Multiple cradles may be disposed at various locations in the dental office, and may be used to charge the intraoral scanners. The cradles may additionally be used to locate intraoral scanners in embodiments.

Rather than purchasing a complete new intraoral scanning system to increase their scanning capabilities, a dentist office may simply purchase additional handheld intraoral scanners and connect those scanners to an already installed intraoral scanning system as scanning requirements grow. Thus, a dentist may initially purchase a single intraoral scanner, display and server computing device, and as their practice grows they may purchase one or more additional intraoral scanners and/or displays and connect those to the same server computing device that the first intraoral scanner is connected to. A dentist may additionally purchase multiple cradles and place those cradles in various rooms in the dentist office.

Also described herein are techniques and systems for pairing or connecting wireless intraoral scanners, peripheral computing devices and/or display devices to a local server computing device. A first computing device (e.g., a mobile computing device) may receive a user command to associate the first computing device with a first intraoral scanner of a plurality of intraoral scanners, the request comprising an identifier of the first intraoral scanner. The first intraoral scanner may include a touchscreen that displays the identifier in embodiments. A user may read the identifier of the first intraoral scanner and input it into the first computing device. The first computing device may then wirelessly connect with a local server computing device and send the identifier of the first intraoral scanner to the local server computing device. The local server computing device may then use the received identifier to wirelessly connect to the first intraoral scanner, and may associate the first computing device with the first intraoral scanner. Once the first computing device and the first intraoral scanner are both wirelessly connected to the local server computing device and associated with one another, intraoral scan data generated by the first intraoral scanner is sent to the second computing device, the intraoral scan data is processed by the local server computing device to generate a three-dimensional (3D) surface of a dental site, the 3D surface or a view of the 3D surface of the dental site is sent to the first computing device, and the 3D surface or the view of the 3D surface of the dental site is displayed by the first computing device.

Additionally, a user may want to associate a first display device of a plurality of display devices with the first intraoral scanner and the first computing device. The first display device may display an identifier of the display device, which may be a code such as a 1-dimensional or 2-dimensional barcode. The first intraoral scanner or the first computing device may receive the identifier of the display device and send it to the local server computing device. The local server computing device may then connect to the first display device using the received identifier, and may then send the 3D surface or the view of the 3D surface to the first display device as well as to the first computing device.

Also described herein is an intraoral scanner and intraoral scanner manufacturing platform that enables a manufacturer and/or owner to modify and/or select a configuration of a scanner from among multiple possible configurations. A scanner may be configured for wired power during use and wireless data transfer, for wired power during use and wired data transfer, for wireless charging while not in use and wireless data transfer, for wireless charging while not in use and wired data transfer, for complete wireless use, and so on.

Various embodiments are described herein. It should be understood that these various embodiments may be implemented as stand-alone solutions and/or may be combined. Accordingly, references to an embodiment, or one embodiment, may refer to the same embodiment and/or to different embodiments. Some embodiments are discussed herein with reference to intraoral scans and intraoral images. However, it should be understood that embodiments described with reference to intraoral scans also apply to lab scans or model/impression scans. A lab scan or model/impression scan may include one or more images of a dental site or of a model or impression of a dental site, which may or may not include height maps, and which may or may not include color images.

FIG. 1A illustrates a distributed system 100 for performing intraoral scanning and/or generating a virtual three-dimensional model of an intraoral site, in accordance with an embodiment. Distributed system 100 may include only components located at a single location (e.g., at a dentist office 108 or a dental lab) or may include components that are at multiple different locations (e.g., components at dental office 108 or dental lab and components at a second location that is remote from the dental office, such as a server farm that provides a cloud computing service 109). The dental office 108 includes a local server computing device 105. In embodiments that incorporate use of a cloud computing service 109 or other remote server, distributed system 100 further includes a remote server computing device 109 connected to local server computing device 105 via a network 180. The network 180 may be a local area network (LAN), a public wide area network (WAN) (e.g., the Internet), a private WAN (e.g., an intranet), or a combination thereof.

Computing device 105 may be coupled to and/or include a data store 125. Computing device 106 may also be connected to and/or include a data store (not shown). The data stores may be local data stores and/or remote data stores. Computing device 105 and computing device 106 may each include one or more processing devices, memory, secondary storage, one or more input devices (e.g., such as a keyboard, mouse, tablet, and so on), one or more output devices (e.g., a display, a printer, etc.), and/or other hardware components. In some embodiments, computing device 105 and/or computing device 106 does not include input and/or output devices (e.g., is not connected to a keyboard, a mouse, a display, etc.).

In embodiments, one or more handheld intraoral scanner 150 (also referred to as an intraoral scanner or simply a scanner) is wirelessly connected to local server computing device 105. In one embodiment, scanner 150 is wirelessly connected to computing device 105 via a direct wireless connection. In one embodiment, scanner 150 is wirelessly connected to computing device 105 via a wireless network. Alternatively, scanner 150 may be connected to a mobile computing device (e.g., mobile computing device 152, 154) via a wired connection, and the mobile computing device may be wirelessly connected to computing device 105 via the wireless network. Alternatively, the scanner 150 may be connected to a desktop computing device, a mobile cart, or another computing device via a wired connection, and the desktop computing device, mobile cart, or other computing device may be wirelessly connected to computing device 105 via the wireless network. Examples of different connection options are described below with reference to FIGS. 15A-19B. In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, local server computing device 105 may be physically connected to one or more wireless access points and/or wireless routers (e.g., Wi-Fi access points/routers). Intraoral scanner 150 may include a wireless module such as a Wi-Fi module, and via the wireless module may join the wireless network via the wireless access point/router.

Distributed system 100 may further include one or more displays 156 operatively connected to local server computing device 105. Some displays 156 may be physically connected to the computing device 105 via a wired connection. Some displays 156 may be wirelessly connected to computing device 105 via a wireless connection, which may be a direct wireless connection or a wireless connection via a wireless network. In embodiments, display 156 is a smart display such as a smart television (TV). A smart TV may include an application installed thereon for communicating with and/or acting as a remote display for computing device 105. Alternatively, or additionally, a smart TV may include a web browser, which may be used to navigate to a web page that streams data from local server computing device 105. For example, the web page may stream a user interface of intraoral scan application 115.

In some embodiments, a intraoral scanning system display adapter (not shown) is plugged into a data input of a display device. For example, an intraoral scanning system display adapter may be connected to a television via an RCA cable, an high definition multimedia interface (HDMI) cable, an optical cable, a universal serial bus (USB) cable, or other audio/video or data cable. In one embodiment, the intraoral scanning system display adapter is a USB dongle that plugs into a USB port of a television. The intraoral scanning system display adapter may be a small device with an application installed thereon for communicating with a local server computing device of an intraoral scanning system. The intraoral scanning system display adapter may include a wireless module for connecting to a wireless network and/or for connecting directly to local server computing device 105. Intraoral scanning system display adapter may further include a processing device (e.g., a system on a chip SoC) that receives data (e.g., view of 3D surfaces generated by local server computing device and/or viewfinder images generated by intraoral scanner 150) and that streams the data to the television to which it is connected. Use of the intraoral scanning system display adapter mitigates a need to develop intraoral scanning system communication applications for many different television brands and/or models. In some embodiments, an intraoral scanning system communication application may be installed on a digital media player such as a Roku, an Amazon Firestick, an Apple TV, etc., which may be plugged into a display device. This may cause the digital media player to perform the role of the intraoral scanning system display adapter.

Distributed system 100 may further include one or more additional computing devices 152, 154 (optionally referred to as peripheral computing devices or control computing devices) operatively connected to local server computing device 105. Some computing devices 152, 154 may be physically connected to the computing device 105 via a wired connection. Some computing devices 152, 154 may be wirelessly connected to computing device 105 via a wireless connection, which may be a direct wireless connection or a wireless connection via a wireless network. In embodiments, one or more computing devices 152, 154 may be mobile computing devices such as laptops, notebook computers, tablet computers, mobile phones, portable game consoles, and so on. In embodiments, one or more computing devices 152, 154 may be traditionally stationary computing devices, such as desktop computers, set top boxes, game consoles, and so on. In the illustrated example, computing device 152 is a tablet computer and computing device 154 is a notebook computer. The computing devices 152, 154 and/or display 156 may act as thin clients to the local server computing device 105. In one embodiment, computing devices 152, 154 and/or display 156 access local server computing device 105 using remote desktop protocol (RDP). In one embodiment, computing devices 152, 154 and/or display 156 access local server computing device 105 using virtual network control (VNC). Other protocols may also be used to connect devices/displays 152, 154, 156 to and/or control local server computing device 105. Some devices (e.g., devices 152, 154 and/or display 156) may be active clients that have control over local server computing device 105. Some devices (e.g., display 156) may be passive clients that do not have control over server computing device and that receive a visualization of a user interface of intraoral scan application 115. In one embodiment, one or more computing devices 152, 154 may operate in a master mode and local server computing device 105 may operate in a slave mode.

Intraoral scanner 150 may be a wireless handheld device that is not tethered to a computer, display, and/or other hardware. Alternatively, intraoral scanner 150 may have a wired connection to a computing device 152, 154, a power adapter, a power box, a cart, and/or another device. Intraoral scanner 150 may include or be a probe (e.g., a hand held probe) for optically capturing three-dimensional structures. The intraoral scanner 150 may be used to perform intraoral scanning of a patient's oral cavity.

Intraoral scanner 150 may include one or more light source, optics and one or more detectors for generating intraoral scan data (e.g., intraoral scans, color images, NIRI images, etc.), one or more buttons and/or touch sensitive inputs (e.g., touch pads and/or touchscreens), and so on. Intraoral scanner 150 may additionally include a memory and/or a processing device (e.g., a controller) for performing initial processing on some or all of the intraoral scan data before it is transmitted to local server computing device 105. Scanner 150 may additionally include a communication module (e.g., a wireless communication module) such as a network interface controller (NIC) capable of communicating via Wi-Fi, via third generation (3G), fourth generation (4G) and/or fifth generation (5G) telecommunications protocols (e.g., global system for mobile communications (GSM), long term evolution (LTE), Wi-Max, code division multiple access (CDMA), etc.), via Bluetooth, via Zigbee, and/or via other wireless protocols. Alternatively, the scanner 150 may connect to a wide area network (WAN) such as the Internet, and may connect to the local server computing device 105 and/or remote server computing device 106 via the WAN. One example of a scanner 150 is the iTero® intraoral digital scanner manufactured by Align Technology, Inc. Another example of a scanner 150 is set forth in U.S. Publication No. 2019/0388193, filed Jun. 19, 2019, which is incorporated by reference herein. Two example scanners are described in greater detail below with reference to FIGS. 13-14.

In embodiments, the scanner 150 may include a wireless communication module, one or more rechargeable battery, one or more replaceable battery (which may or may not be rechargeable), a charging module for charging the one or more rechargeable battery and/or a controller (e.g., a processing device) for controlling one or more functions of the scanner 150, among many other components, some of which are discussed herein below.

In addition to or instead of including a wireless communication module, scanner 150 may include an Ethernet network interface controller (NIC), a universal serial bus (USB) port, a parallel port, a serial port, or other wired port. In some embodiments, the NIC or port may connect the scanner 150 to a computing device 152, 154 via a wired connection. Rather than wirelessly sending intraoral scan data to the local server computing device 105, scanner 150 may instead send the intraoral scan data to the computing device 152, 154 to which it is connected via the wired connection, which may then forward the intraoral scan data on to local server computing device 105 via a wireless connection. In such an embodiment, the wired connection may also provide power to the scanner 150.

Intraoral scanner 150 may generate intraoral scans, which may be or include color or monochrome 3D information, and send the intraoral scans to local server computing device 105 via the wireless connection. In some embodiments, intraoral scans include height maps. Intraoral scanner 150 may additionally or alternatively generate color two-dimensional (2D) images (e.g., viewfinder images), and send the color 2D images to local server computing device 105 via the wireless connection. Scanner 150 may additionally or alternatively generate 2D or 3D images under certain lighting conditions, such as under conditions of infrared or near-infrared (NIRI) light and/or ultraviolet light, and may send such 2D or 3D images to server computing device 105 via the wireless connection. Intraoral scans, color images, and images under specified lighting conditions (e.g., NIRI images, infrared images, ultraviolet images, etc.) are collectively referred to as intraoral scan data 135A-N. An operator may start recording scans with the scanner 150 at a first position in the oral cavity, move the scanner 150 within the oral cavity to a second position while the scans are being taken, and then stop recording the scans. In some embodiments, recording may start automatically as the scanner 150 identifies teeth and/or other objects.

A local intraoral scan application 115 running on computing device 105 may wirelessly communicate with the scanner 150 to effectuate an intraoral scan. A result of the intraoral scan may be intraoral scan data 135A, 135B through 135N that may include one or more sets of intraoral scans, one or more sets of viewfinder images (e.g., color 2D images showing a field of view of the intraoral scanner), one or more sets of NIRI images, and so on. Each intraoral scan may be a two-dimensional (2D) or 3D image that includes a height information (e.g., a height map) of a portion of a dental site, and thus may include x, y and z information. In one embodiment, each intraoral scan is a point cloud. In one embodiment, the intraoral scanner 150 generates numerous discrete (i.e., individual) intraoral scans and/or additional images. In some embodiments, sets of discrete intraoral scans may be merged into a smaller set of blended intraoral scans, where each blended scan is a combination of multiple discrete intraoral scans.

In embodiments, scanner 150 generates and sends to computing device 105 a stream of intraoral scan data. The stream of intraoral scan data may include separate streams of intraoral scans, color images and/or NIRI images (and/or other images under specific lighting conditions) in some embodiments. In one embodiment, a stream of blended intraoral scans is sent to computing device 105.

In some embodiments, scanner 150 compresses intraoral scan data (e.g., intraoral scans, color images, NIRI images, etc.) prior to sending the intraoral scan data to local server computing device. In some embodiments, video compression techniques (e.g., optionally based on H.264 codec) are used to compress the stream of intraoral scan data. In some embodiments, intraoral scan data is compressed by a factor of 20 to 40. Accordingly, similarities between sequentially generated scans/images may be used to reduce the amount of data sent for each scan/image. For example, scanner 150 may determine a delta or difference between a previously sent scan and a current scan, and may send over the delta or difference rather than the scan or image. This may significantly reduce an amount of information sent over the wireless connection. Scanner 150 may include an onboard (e.g., internal) processing device that performs compression of at least some of the intraoral scan data.

In some embodiments, scanner 150 does not send whole scans and/or whole images to computing device 105. In one embodiment, scanner 150 may perform one or more computations on the intraoral scan data (e.g., intraoral scans, color images, NIRI images, etc.) to determine one or more areas of interest (AOIs) within the intraoral scan data. The one or more computations may be performed using trained machine learning models that are optimized for resource constrained devices and/or using one or more image processing algorithms. Scanner 150 may then perform data reduction such as by cropping the intraoral scans, images, etc. such that areas outside of the AOIs are cropped out of the scans/images and/or by reducing a resolution of areas outside of the AOIs. Scanner 150 may include an onboard processing device that can perform the one or more computations and/or data reduction/cropping of the scan data. The cropped or reduced scans/images are then sent to computing device 105. This, in addition to or instead of performing compression on the intraoral scan data, can reduce a total bandwidth associated with sending intraoral scan data to local server computing device 105. In one embodiment, AOIs are determined for intraoral scans, and intraoral scans are cropped or reduced before sending to computing device 105, but whole color images such as color viewfinder images are sent to computing device 105 without first cropping or reducing the color images. The uncropped viewfinder image may be presented to a doctor/dentist during the scanning process to show a current field of view of the scanner 150.

Local server computing device 105 receives intraoral scan data from scanner 150, then stores the intraoral scan data 135A-N in data store 125. If the intraoral scan data has been compressed, computing device 105 may decompress the intraoral scan data before it is stored. Alternatively, computing device 105 may store the intraoral scan data in a compressed state, and may decompress the intraoral scan data before processing it. In embodiments, each item of intraoral scan data (e.g., each intraoral scan, image, etc.) generated by a scanner 150 includes metadata that indicates a unique identifier of the scanner 150 that generated the intraoral scan data. Accordingly, computing devices 105 that are connected to multiple scanners 150 may easily distinguish between intraoral scan data from different scanners 150 based on the metadata associated with the intraoral scan data.

According to an example, a user (e.g., a practitioner) may subject a patient to intraoral scanning. In doing so, the user may apply scanner 150 to one or more patient intraoral locations. The scanning may be divided into one or more segments. As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan/image data sets, each of which may include 2D intraoral scans/images and/or 3D intraoral scans/images of particular teeth and/or regions of an intraoral site. In one embodiment, separate scan/image data sets are created for the maxillary arch, for the mandibular arch, for a patient bite, and for each preparation tooth. Alternatively, a single large intraoral scan/image data set is generated (e.g., for a mandibular and/or maxillary arch). Such scans/images may be provided from the scanner to the computing device 105 in the form of one or more points (e.g., one or more pixels and/or groups of pixels). For instance, the scanner 150 may provide such a 3D scan/image as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Additionally, the manner in which the oral cavity is to be scanned may depend on a doctor's scanning preferences and/or patient conditions.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

During an intraoral scan session, local intraoral scan application 115 receives and processes intraoral scan data (e.g., intraoral scans) and generates a 3D surface of a scanned region of an oral cavity (e.g., of a dental site) based on such processing. To generate the 3D surface, intraoral scan application 115 may register and "stitch" or merge together the intraoral scans generated from the intraoral scan session in real time or near-real time as the scanning is performed. In one embodiment, performing registration includes capturing 3D data of various points of a surface in multiple scans (views from a camera), and registering the scans by computing transformations between the scans. The 3D data may be projected into a 3D space for the transformations and stitching. The scans may be integrated into a common reference frame by applying appropriate transformations to points of each registered scan and projecting each scan into the 3D space.

In one embodiment, registration is performed for adjacent or overlapping intraoral scans (e.g., each successive frame of an intraoral video). In one embodiment, registration is performed using blended scans and/or reduced or cropped scans. Registration algorithms are carried out to register two or more adjacent intraoral scans and/or to register an intraoral scan with an already generated 3D surface, which essentially involves determination of the transformations which align one scan with the other scan and/or with the 3D surface. Registration may involve identifying multiple points in each scan (e.g., point clouds) of an scan pair (or of a scan and the 3D model), surface fitting to the points, and using local searches around points to match points of the two scan (or of the scan and the 3D surface). For example, intraoral scan application 115 may match points of one scan with the closest points interpolated on the surface of another image, and iteratively minimize the distance between matched points. Other registration techniques may also be used. Intraoral scan application 115 may repeat registration and stitching for all scans of a sequence of intraoral scans and update the 3D surface as the scans are received.

An output controller 118 of local intraoral scan application 115 may determine which external device (e.g., display device 156, computing device 152, computing device 154, etc.) to send the 3D surface or a view of the 3D surface to, and transmit the 3D surface or the view of the 3D surface to the appropriate device. Output controller 118 may stream updated versions and/or views of the 3D surface to the appropriate device 152, 154, 154 or devices as additional scans are received and processed. Output controller 118 may additionally or alternatively stream viewfinder images to the appropriate device 152-156 as the viewfinder images are received. Thus, current scan progress and a current field of view of the scanner 150 may be output to a display and/or computing device in real time or near-real time as scanning is performed. A doctor may therefore assess their progress by viewing a display that is at hand during the scanning process. If the doctor moves to a different room with a different display, the doctor may merely associate the scanner 150 with the different display to cause scans, 3D surfaces, images etc. to be sent to the different display.

In one embodiment, a scanner 150 is associated with a particular device or set of devices 152-156, and output controller 118 identifies the device or devices 152-156 associated with the scanner 150 and outputs the 3D surface and/or viewfinder images to the identified device(s) 152-156. The association between the scanner and device(s) may be changed at any time based on user input and/or automatically based on additional information. In one embodiment, prior to starting a scanning session a doctor selects a device to be associated with scanner 150. One or more device 152-156 may include an endpoint intraoral scan application installed thereon that is configured to communicate with and/or control local intraoral scan application 115. Additionally, or alternatively, one or more device 152-156 may include a web browser, and via the web browser a user may navigate to a web interface for controlling local intraoral scan application 115. From the device 152-156 (e.g., via the web interface or endpoint intraoral scan application), a user may select a particular scanner 150 to associate with the device 152-156.

In one embodiment, a device 152-156 may display a code (e.g., a one dimensional or two dimensional bar code such as a QR code). Scanner 150 may be used to scan the code, which may be a unique code associated with the device displaying the code), and may send an image of the scanned code to local intraoral scan application 115. Output controller 118 may then decode the scanned code, and may determine a device to associate scanner 150 with based on the decoded code. Alternatively, an onboard processing device on scanner 150 may decode the scanned code and determine a value therefrom. Scanner 150 may then send the value to local intraoral scan application 115, and output controller 118 may determine a device 152-156 associated with the value and associate scanner 150 with that device 152-156.

A user (e.g., a practitioner) may navigate through scanning segments (e.g., an upper dental arch segment, a lower dental arch segment, a bite segment, and optionally a separate segment for each preparation tooth) via a user interface (UI) of the intraoral scan application 115 by various input devices, such as a cursor control device (e.g., a mouse), a remote control (e.g., of a smart TV), a touch input device (e.g., touchscreen) of a computing device 152-154 or display 156 wirelessly connected to local server computing device 105. In embodiments, a scanner 150 may allow the user to easily navigate or control the user interface of the intraoral scan application 115 using the touch input and/or buttons of the scanner 150, thereby minimizing instances of the user moving between a computing device 152, 154 and the patient. For example, the user may utilize a combination of buttons and various touch gestures on the touch sensor of the scanner 150 to navigate the intraoral scan application 115 without moving to the computing device 152, 154 to navigate and/or control the user interface. In some embodiments, intraoral scanner 150 includes a touchscreen that outputs one or more virtual buttons. A user may interact with the one or more virtual buttons (e.g., by pressing a virtual button) to send a control signal to the intraoral scan application 115. Which virtual buttons are displayed on the intraoral scanner's 150 touchscreen may depend on a current mode of the intraoral scan application 115.

When a scan session is complete (e.g., all scans for an intraoral site or dental site have been captured), model generator 122A of local intraoral scan application 115 may generate a virtual 3D model (also referred to as a digital 3D model) of one or more scanned dental sites. The virtual 3D model includes a 3D surface of the one more scanned dental sites, but has a higher degree of accuracy than the 3D surface generated during the scanning process. To generate the virtual 3D model, intraoral scan application 115 may register and "stitch" or merge together the intraoral scans generated from the intraoral scan session. In one embodiment, registration is performed for adjacent and/or overlapping intraoral scans (e.g., each successive frame of an intraoral video). In one embodiment, registration is performed using blended scans and/or reduced or cropped scans. Registration algorithms may be carried out to register two or more adjacent intraoral scans and/or to register an intraoral scan with a 3D model, which essentially involves determination of the transformations which align one scan with the other scan and/or with the 3D model. Registration may involve identifying multiple points in each scan (e.g., point clouds) of a scan pair (or of a scan and the 3D model), surface fitting to the points, and using local searches around points to match points of the two scans (or of the scan and the 3D model). For example, intraoral scan application 115 may match points of one scan with the closest points interpolated on the surface of another scan, and iteratively minimize the distance between matched points. Other registration techniques may also be used. The registration and stitching that are performed to generate the 3D model may be more accurate than the registration and stitching that are performed to generate the 3D surface that is shown in real time or near-real time during the scanning process.

Intraoral scan application 115 may repeat registration for all scans of a sequence of intraoral scans to obtain transformations for each scan, to register each scan with the previous one and/or with a common reference frame (e.g., with the 3D model). Intraoral scan application 115 integrates all scans into a single virtual 3D model by applying the appropriate determined transformations to each of the scans. Each transformation may include rotations about one to three axes and translations within one to three planes.

In many instances, data from one or more intraoral scans does not perfectly correspond to data from one or more other intraoral scans. Accordingly, in embodiments intraoral scan application 115 may process intraoral scans to determine which intraoral scans (and/or which portions of intraoral scans) to use for portions of a 3D model (e.g., for portions representing a particular dental site). Intraoral scan application 115 may use data such as geometric data represented in scans and/or time stamps associated with the images to select optimal scans to use for depicting a dental site or a portion of a dental site (e.g., for depicting a margin line of a preparation tooth) in embodiments. In embodiments, intraoral scan application 115 merges or blends together scans with conflicting or differing information for the same points using a weighted or unweighted combination of surface information from multiple scans.

Once a 3D model of a dental site (e.g., a dental arch) is generated, output controller 118 of intraoral scan application 115 may generate a view of the 3D model and output the view to an appropriate device 152-156 for display of the 3D model to a user (e.g., a doctor) via a display of the device 152-156. A doctor may then interface with the device 152-156 to generate commands to change the view of the 3D model (e.g., by zooming in or out, panning, rotating, etc.). The device 152-156 may send the command to scan application 115, which may change the view of the 3D model, and then send the updated view to the device 152-156. In some embodiments, a touchscreen of the intraoral scanner 150 includes virtual buttons for controlling the view of the intraoral scanner 150 and/or interprets touch gestures (e.g., pinch gestures, swipe gestures, etc.) to control the view of the 3D model. In some embodiments, the touchscreen of the intraoral scanner supports multi-touch, and different numbers of detected fingers cause different actions to be performed (e.g., pan, zoom, rotate, etc.). The touchscreen may detect user input, may generate commands based on the user input, and may send the detected commands and/or the user input to the local server computing device for control of the intraoral scan application 115. In this manner, the 3D model can be checked visually by the doctor. The doctor can virtually manipulate the 3D model via the user interface of the device 152-156 and/or via the touchscreen of the intraoral scanner with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model).

In one embodiment, the scanner 150 is used as an input device to control the view of the 3D model or other 3D surface of a dental site. Embodiments of the present invention enable a user to perform operations (such as to control or navigate a user interface of an intraoral scan application and/or to manipulate medical images or a representation generated from medical images) while still engaged with a patient. Scanner 150 may include one or more buttons, one or more touch sensitive inputs (e.g., touch pads and/or touchscreens) and/or one or more inertial measurement devices (e.g., accelerometers and/or gyroscopes) that may be used to navigate the user interface of the intraoral scan application and/or manipulate medical images or a 3D model of one or more dental arches.

Local intraoral scan application 115 may include a user interface (e.g., a graphical user interface (GUI)) that receives user commands and provides a graphical and/or audio output to a device 152-156 that is wirelessly connected to local server computing device 105. The device 152-156 may then use a display and/or speakers of the device to output the graphical and/or audio output to a user. The user interface enables users to interact with intraoral scan application 115 through manipulation of graphical elements such as graphical icons and visual indicators such as buttons, menus, and so on, which are output via the device 152-156. Intraoral scan application 115 may include a number of modes, such as a planning mode, a scan mode, an image processing mode, and a delivery mode. The user interface on the device 152-156 and/or the touchscreen of the intraoral scanner 150 may display different graphical elements for each of the various modes.

Navigation or control of the user interface of the intraoral scan application 115 may be performed via user input. The user input may be performed through various devices, such as a touch input device (e.g., a touchscreen), keyboard, mouse, or other similar control devices of one or more device 152-156 wirelessly connected to local server computing device 105. User input may also be provided via scanner 150 in embodiments, such as via a touchpad and/or touchscreen of the intraoral scanner 150. Navigation of the user interface may involve, for example, navigating between various modules or modes, navigating between various segments, controlling the viewing of the 3D rendering, or any other user interface navigation. A touch sensitive scanner (e.g., which may include a touchscreen) allows the user to navigate or control the user interface without continuously disengaging from the patient.

In one embodiment, intraoral scan application 115 includes a touch input module (not shown) that receives and interprets touch input data from scanner 150. Scanner 150 may receive different types of touch input such as hold gestures, swipe gestures, tap gestures, circular gestures, and so on. Additionally, or alternatively, a touchscreen of the intraoral scanner 150 may display multiple different virtual buttons, and user interaction with each of the virtual buttons may trigger a different action in local intraoral scan application 115. The touch input module may determine a type of touch gesture that a user performed based on the received touch input and/or what virtual button was pressed based on a detected finger. The touch input module may then initiate functions or operations of the user interface (or intraoral scan application generally) responsive to the determined touch gesture. The functions or operations that are initiated may depend both on the current mode of the intraoral scan application 115 and the determined touch gesture and/or pressed virtual button. Accordingly, the same touch gesture or finger interaction with a same region of the touchscreen may cause a first function to be performed in a first mode of the intraoral scan application and may cause a second function to be performed in a second mode. Specific modes of operation and touch gestures and/or virtual buttons that initiate operations or functions for those modes are discussed in greater detail below.

In one embodiment, local server computing device 105 executing local intraoral scan application 115 receives a touch input from a touch sensor (e.g., a touchpad or touchscreen) of scanner 150 (e.g., which may include a press of a virtual button on a touchscreen) and/or a button press from a button of scanner 150 during an intraoral scan session. In one embodiment, local intraoral scan application 115 determines whether the touch input is a hold gesture or a swipe gesture. The computing device may then perform a first function or operation to control a user interface of the intraoral scan application if the touch input is a hold gesture (or a particular button of virtual button is depressed) and a second function or operation to control the user interface of the intraoral scan application if the touch input is a swipe gesture (or another button or virtual button is depressed). Examples of functions that may be performed include activating a gyroscope in the intraoral scanner 150, using data from the gyroscope to control an orientation of a virtual 3D model (e.g., if a hold gesture is detected) and proceeding to next or previous scan segments (e.g., if a swipe gesture is detected). The functions or operations performed responsive to the hold or swipe gestures and/or responsive to a user pressing a virtual button of a touchscreen on the intraoral scanner 150 may be functions that traditionally are performed responsive to a user using a keyboard, mouse and/or touchscreen of a computer. Results of the inputs from the scanner 150 (e.g., button pushes, virtual button pushes, swipe gestures, hold gestures, movement of the scanner 150, etc.) may cause one or more menus or options of the intraoral scan application 115 to be navigated or transitioned between, and/or an updated menu or options to be output to a device 152-156 associated with the intraoral scanner 150 and/or to a touchscreen of the intraoral scanner 150. In some embodiments, pressing a particular button or buttons (including one or more virtual buttons of a touchscreen) or performing a hold gesture of a touch sensitive input causes local intraoral scan application 115 to output a navigation overlay to a device 152-156. While and/or after the button(s) and/or virtual buttons are pushed and/or during the hold gesture of the touch sensitive input, a user may move the scanner 150 and motion of the scanner may be used as an input to navigate the navigation overlay. For example, the scanner 150 may be moved left to select a first menu option (e.g., switch to previous scan segment), right to select a second menu option (e.g., switch to next scan segment), up to select a third menu option or down to select a fourth menu option. The movement of the scanner may register as an input that causes a user interface of the intraoral scan application 115 to be updated, and the updated user interface may be output to the device 152-156 associated with scanner 150.

By providing touch sensors, touchscreens and/or buttons in the intraoral scanner 150 and an intraoral scan application 115 that can respond to touch input from such touch sensors, that can respond to input from touchscreens (e.g., presses of virtual buttons displayed on a touchscreen) and/or that can respond to use of the buttons, embodiments improve the efficiency of performing intraoral scans. Additionally, display 156 may not include an input device for controlling intraoral scan application 115. However, scanner 150 may function as such an input device for controlling intraoral scan application 115. For example, if the intraoral scan application 115 is outputting image data to display 156, then a user of scanner 150 may press a physical button, press a virtual button of a touchscreen on the intraoral scanner 150 and/or use a hold gesture on a touch input of the scanner 150 to activate a view mode. During the view mode, the user may move the scanner and/or interface with the touchscreen or touch pad on the intraoral scanner 150 to rotate a view of a 3D surface or 3D model of a dental site. The user may release the button, virtual button or hold gesture to resume a scanning mode and continue generating intraoral scans. Alternatively, the user may press a different virtual button to resume the scanning mode and continue generating intraoral scans.

In one embodiment, intraoral scan application 115 includes a treatment planner 123A configured to perform treatment planning for orthodontic treatment and/or prosthodontic treatment. Treatment planner 123A may additionally perform dental diagnostics and/or prognostics. Such diagnostics and/or prognostics may be performed, for example, responsive to commands from a computing device 152, 154. Via the user interface of the treatment planner 123A, a practitioner may view one or more of the upper dental arch, the lower dental arch, a particular preparation tooth and/or the patient bite, each of which may be considered a separate scan segment or mode. The treatment planner 123A in embodiments generates an orthodontic treatment plan, including a 3D model for a final tooth arrangement and 3D models for one or more intermediate tooth arrangements. Treatment planner 123A may additionally or alternatively perform diagnostics of a patient's oral cavity and/or provide a prognosis of one or more dental conditions and/or suggested treatments for the one or more dental conditions. The treatment planner 123A may further perform one or multiple different analyses of the patient's dental arches and/or bite. The analyses may include an analysis for identifying tooth cracks, an analysis for identifying gum recession, an analysis for identifying tooth wear, an analysis of the patient's occlusal contacts, an analysis for identifying crowding of teeth (and/or spacing of teeth) and/or other malocclusions, an analysis for identifying plaque, an analysis for identifying tooth stains, an analysis for identifying caries, and/or other analyses of the patient's dentition. Once the analyses are complete, a dental diagnostics summary and/or detailed dental diagnostics information optionally including prognosis and/or treatment options may be presented to a device 152-156. A doctor may control the treatment planner 123A and navigate menus and options of the treatment planner's user interface using the scanner 150 or using one of devices 152-156.

Intraoral scan application 115 may initiate a scanning mode responsive to input from scanner 150. Responsive to further input from scanner 150 or from a device 152-156 associated with scanner 150, intraoral scan application 115 may transition from the scanning mode to an image processing mode to generate one or more 3D models. Responsive to further input from scanner 150 or from a device 152-156 associated with scanner 150, intraoral scan application 115 may transition from the image processing mode to a treatment planning mode or back to the scanning mode.

The following non-limiting example may help understand the process more fully. A patient who wishes to straighten their teeth may opt for Invisalign® treatment. Invisalign is a process that creates a custom made series of clear aligners specifically for the patient. The clear aligners are worn over the patient's teeth and gradually shift the patient's teeth. A new set of aligners may be worn after a specified period of time (e.g., two weeks) until treatment is complete.

The patient may visit a dental practitioner or orthodontist to begin Invisalign treatment. The dental practitioner may utilize distributed scanning system 100 to scan the patient's teeth in a scanning mode. The dental practitioner may use scanner 150 to capture the patient's teeth segments (e.g., upper arch, lower arch, bite segments) in one or more sets of intraoral scans. The intraoral scan application 115 may register and stitch together the intraoral scans to create a 3D rendering of the scanned segments and present the 3D rendering to the dental practitioner on the user interface of the intraoral scan application through one of devices 152-156. Once the scans are completed, the dental practitioner may next navigate to the image processing mode, which may generate a virtual 3D model by registering and stitching together the intraoral images. Once an adequate set of 3D renderings and/or virtual 3D model are complete, the 3D renderings and/or 3D models may be saved to the patient profile.

The dental practitioner may then provide input via the scanner 150 or a computing device 152-154 to switch to a planning mode, in which a final tooth arrangement may be determined and one or more intermediate tooth arrangements may be determined. A treatment plan may be generated to provide a progression of treatment stages from the patient's initial tooth arrangement to the target final tooth arrangement, where a separate 3D model is associated with each treatment stage.

Once an adequate set of 3D models is generated, the 3D models may be saved to the patient profile. The dental practitioner may then navigate to a delivery mode to electronically send the completed patient profile to a processing center. The processing center may then generate the custom made series of clear aligners for the patient and deliver the clear aligners to the dental practitioner. The patient would then return to the dental practitioner to receive the first set of clear aligners and verify the clear aligners properly fit onto the patient's teeth.

In one embodiment, a doctor may erase or remove a portion of the 3D model of the dental arch that the doctor has determined to have a low quality via an interface provided by one of devices 152-156. Intraoral scan application 115 may direct a user to generate one or more additional intraoral images of the dental site corresponding to the portion of the 3D model (and/or corresponding set or sets of intraoral scans) that was deleted or removed. The user may then use the scanner 150 to generate the one or more additional intraoral scans, which at least partially overlaps with previously generated intraoral scans. The one or more additional intraoral scans may be registered with the 3D model (and/or with the intraoral scans data sets used to create the 3D model) to provide a composite of the 3D model and the one or more additional intraoral scans. In the composite, the part of the 3D model that was previously deleted/removed is at least partially replaced with a corresponding part of the one or more additional intraoral scans. However, the portions of the one or more additional scans that are outside of the deleted or removed part of the 3D model may not be applied to the composite or updated 3D model.

In some embodiments, local server computing device 105 offloads one or more operations to remote server computing device 106. Remote server computing device 106 may be provided by a cloud computing service 109, such as Amazon Web Services (AWS). Remote server computing device 106 may have increased resources such as memory resources, processing resources, and so on as compared to local server computing device 105. In some embodiments, rather than operations such as registration, stitching, treatment planning, and so forth being performed at local intraoral scan application 115, some or all of these operations may be performed by remote intraoral scan application 116. For example, as local intraoral scan application 115 receives intraoral scan data, it may send the intraoral scan data to remote intraoral scan application 116 via network 180. Remote intraoral scan application 116 may process the intraoral scan data (e.g., such as by performing registration and stitching of the intraoral scan data, generating a 3D surface, generating a 3D model, generating a treatment plan, etc.), and send back a generated 3D surface and/or other information that results from the processes performed on the intraoral scan data. Local intraoral scan application 115 may then send a view of the 3D surface and/or other information on to a device 152-156 associated with scanner 150. In one embodiment, remote intraoral scan application 116 includes a model generator 1228 that generates 3D models based on scan data and/or a treatment planner 1238 that generates a treatment plan based on a generated 3D model of a patient's oral cavity.

In one embodiment, local server computing device 105 includes credentials for accessing remote server computing device 106 and/or patient records stored at remote server computing device 106. The credentials may be used to identify and authenticate the dentist office that owns the local server computing device 105 and/or the one or more scanners 150 connected to local server computing device 105.

In one embodiment, each scanner 150 and each local server computing device 105 is owned by a particular dental office, and the ownership information may be registered with local server computing device 105 and/or remote server computing device 106. Local server computing device may receive a unique ID of scanner 150 from the scanner, and may determine whether that scanner is registered with local server computing device 105. If local server computing device 105 has a record of scanner 150, then scanner 150 may be permitted to connect to computing device 105. If local server computing device does not have a record of the particular scanner 150 attempting to connect to local server computing device, it may query a remote server (e.g., remote server computing device) for ownership information regarding the scanner 150. The remote server may determine a unique ID of the local server computing device 105 and of scanner 150, and determine whether both are registered to the same entity (or if one is unregistered). If both are registered to the same entity, the remote server may respond to local server to permit connecting to the scanner 150. Local server computing device 105 may then update its records to thenceforth permit connections from scanner 150. If scanner is unregistered, remote server may perform registration to register the scanner 150 to the same entity (e.g., to the same account) associated with local server computing device, and may then send an instruction to local server to permit connecting to the scanner 150. However, if scanner is registered to a different entity or account than local server computing device 105, then remote server may notify local server computing device not to connect to scanner 150.

In some embodiments, scanner 150 may connect to remote server computing device 106 without connecting to local server computing device 105. For example, scanner 150 may include a 5G modem, which may be used to connect to a wireless service provider, and via the wireless service provider may connect to remote server computing device. In such embodiments, local server computing device may be omitted, and scanners 150 and/or computing devices 152, 154 and/or displays 156 may communicate with remote server computing device 106. In such an embodiment, remote server computing device may perform all of the functions discussed herein with reference to local server computing device 105.

In some embodiments, local intraoral scan application 115 includes a location determiner 120, which performs one or more operations to determine a location of scanner 150. Location determiner 120 is discussed in greater detail with reference to FIG. 1B.

Figure 1B:
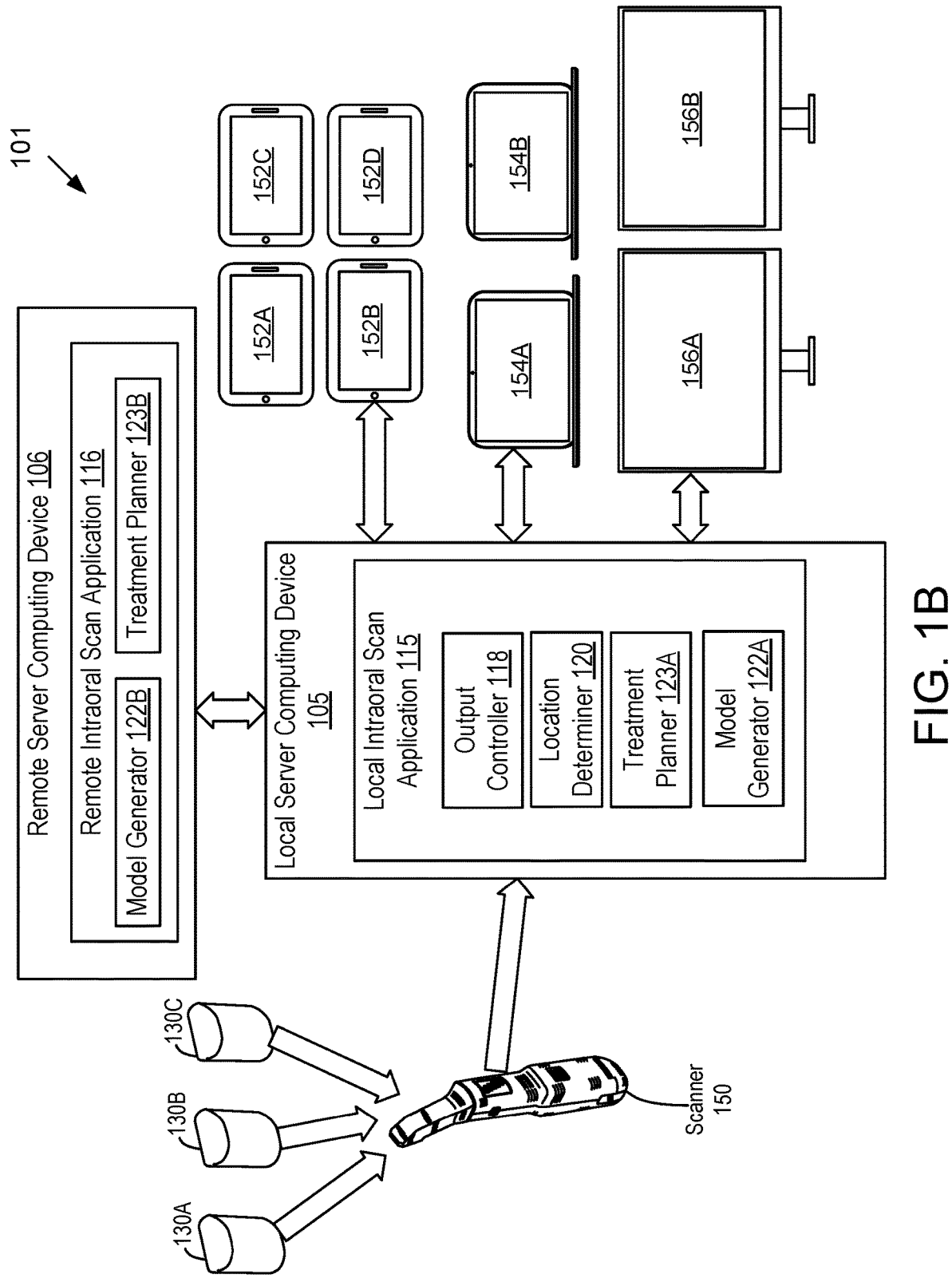
FIG. 1B illustrates a distributed system for performing intraoral scanning and/or generating a virtual three-dimensional model of an intraoral site, in accordance with an embodiment.

FIG. 1B illustrates a distributed system 101 for performing intraoral scanning and/or generating a virtual three-dimensional model of an intraoral site, in accordance with an embodiment. Distributed system 101 includes scanner 150, local server computing device 105, additional computing devices 152A-D, 154A-B, and displays 156A-B. Distributed system 101 may further include remote server computing device 106. Local server computing device 105 includes local intraoral scan application 115, which may include output controller 118, location determiner 120, treatment planner 123A and/or model generator 122A. Remote server computing device 106 includes remote intraoral scan application 116, which may include model generator 122B and/or treatment planner 123B.

Distributed system 101 may substantially correspond to distributed system 100 of FIG. 1A, except that additional computing devices 152A-D, computing devices 154A-B and displays 156A-B are shown for distributed system 101. Additionally, distributed system 101 may include one or more cradles 130A-C.

Each cradle 130A-C may be a charging station used to hold and charge scanner 150. In some embodiments, cradles 130A-C include wireless chargers that wirelessly charge a scanner 150 (e.g., that includes one or more rechargeable batteries) having wireless charging capability that is placed in the cradles 130A-C. For example, a cradle 130A-C may include a primary induction coil and a scanner 150 may include a secondary induction coil. The primary induction coil of the cradle 130A-C may induce a current in the secondary induction coil of the scanner 150 to charge the scanner 150 via resonant inductive coupling. In such embodiments, the scanner 150 may not include exposed charging pins. Additionally, scanner 150 and cradles 130A-C may support other types of wireless charging technologies, such as radio charging, and resonance charging.

In some embodiments, cradles 130A-C include pins that engage with exposed charging pins of a scanner 150 (e.g., that includes one or more rechargeable batteries) when the scanner 150 is placed in the cradle 130A-C. The cradle 130A-C may then perform wired charging of the scanner 150 via contact between the pins of the cradle 130A-C and the exposed charging pins of the scanner 150.

Cradles 130A-C may not be wirelessly connected to any other component of distributed system 101 in embodiments. When scanner 150 is inserted into a cradle 130A-C, a physical connection between the scanner 150 and cradle 130A-C may be established, and the cradle 130A-C may charge a battery of scanner 150 via the physical connection. Alternatively, wireless charging may be performed to charge a battery of scanner 150.

In embodiments, each cradle 130A-C includes a wireless module that periodically or continuously broadcasts a signal that includes a unique identifier of the respective cradle 130A-C. In one embodiment, cradles 130A-C send a wired signal to scanners that are plugged into the cradles 130A-C via a physical connection between the cradle and scanner, where the wired signal includes a unique identifier of the cradle 130A-C. In such an embodiment, the cradles 130A-C may not include a wireless module and may not transmit a wireless signal.

Each cradle 130A-C may send or broadcast a different unique identifier than other cradles 130A-C. Scanner 150 may receive signals broadcast or sent by one or more cradles 130A-C depending on a location of scanner 150. A location of each cradle 130A-C may be input into intraoral scan application 115 during a configuration process, and so may be known by local intraoral scan application 115. Scanner 150 may send information on received unique identifiers from one or more cradles 130A-C to local server computing device 105. Location determiner 120 may then determine a location of the scanner 150 based on the known locations of the cradles 130A-C and the received information regarding unique identifier(s) received by scanner 150. Location determiner 120 may then output a notification to any computing device 152A-D, 154A-B and/or display 156A-B wirelessly connected to local server computing device 105 indicating the determined location of scanner 150. In one embodiment, a doctor or technician uses a computing device 152A-D, 154A-B to request a location of scanner 150, and location determiner 120 outputs the determined location to the requesting computing device 152A-D, 154A-B.

In one embodiment, the signal broadcast by each cradle 130A-C may be a low power signal that is detected by scanner 150 if the scanner is within a threshold distance from a cradle 130A-C. Accordingly, the scanner 150 may detect a signal from a single cradle, and report the unique identifier included in the signal to computing device 105. In one embodiment, the low power signal output by the cradles 130A-C is signal corresponding to a low energy unidirectional wireless protocol (e.g., the iBeacon® protocol or other Bluetooth® low energy (BLE) protocol) to transmit information usable to identify the cradle 130A-C. In one embodiment, scanner 150 detects a signal from a cradle 130A-C if the scanner is inserted into the cradle, but does not detect a signal from a cradle if it is removed from the cradle.

In one embodiment, the signal broadcast by each cradle 130A-C is a Bluetooth signal, a Zigbee signal, a Wi-Fi signal, or a signal broadcast according to another wireless protocol. The cradles 130A-C may broadcast signals that are powerful enough such that scanner 150 may receive signals from multiple cradles 130A-C. Scanner 150 may report the received signals as well as signal strengths, time of flight, delay, angle of signals, etc. of the received signals to computing device 105. Computing device 105 may then use known locations of cradles and signal strengths, time of flight, delay, angle of signals, etc. to determine a location of scanner 150. In one embodiment, scanner 150 is determined to be proximate to a cradle associated with a strongest signal strength. In one embodiment, location determiner 120 performs triangulation using the signal strengths, time of arrival, delay and/or the locations of the cradles from which signals were received to determine a probable location of scanner 150.

In one embodiment, scanner 150 includes a radio frequency identification (RFID) or near field communication (NFC) reader, and periodically broadcasts a signal to read RFID or NFC chips. Each cradle 130A-C may include a unique RFID or NFC identifier, and upon receiving an RFID or NFC reading signal, may respond by emitting a unique identifier. Scanner 150 may then report the unique identifier to computing device 105, which may determine a location of the scanner based on the unique ID as discussed above. Alternatively, each cradle 130A-C may include an RFID or NFC reader, which may read an RFID or NFC chip on scanner 150, and may include a Wi-Fi module to wirelessly connect to computing device 105 and report on a received signal from a scanner 150. Location determiner 120 may then determine a location of scanner 150 based on a known location of the cradle 130A-C that detected the scanner 150.

In one embodiment, a Wi-Fi signal may be used to locate scanner 150 rather than signals from cradles 130A-C. For example, a dentist office may be set up with a Wi-Fi mesh network that includes three or more access points. Scanner 150 may receive signals from and send signals to some or all of the wireless access points. Based on known locations of the wireless access points and information associated with signals to/from the access points such as signal strengths, time of flight, delay, angle of signals, etc., location determiner 120 may determine a location of scanner 150.

In one embodiment, an distributed system 100 includes an indoor positioning system that includes multiple units that are spread throughout a dental office, where each of the units includes transmitters, receivers and/or transceivers. Each unit may be configured to transmit a signal to be received by scanner 150 and/or to receive a signal from scanner 150. The signals may be light signals, radio frequency (RF) signals, magnetic fields, acoustic signals (e.g., ultrasonic signals), or other types of signals. Based on signals received by the scanner 150 from multiple units and/or based on signals received from the scanner 150 by multiple units of the indoor positioning system, the indoor positioning system may determine a location of scanner 150, which may be reported to local server computing device 105.

In FIG. 1B, arrows show the direction of information flow, according to at least one embodiment. As shown, cradles 130A-C broadcast information that can be received by scanner 150. Scanner 150 sends information (e.g., information received from cradles 130A-C and/or intraoral scan data) to location server computing device 105. Local server computing device 105 may exchange information with remote server computing device 106 and may further exchange information with computing devices 152A-D, 154A-B and/or displays 156A-B. For example, computing devices 152A-D, 154A-B and displays 156A-B may receive data to present a user interface including views of 3D models and/or 3D surfaces from computing device 105, and may send instructions to control and/or navigate location intraoral scan application 115 to computing device 105.

Figure 2:
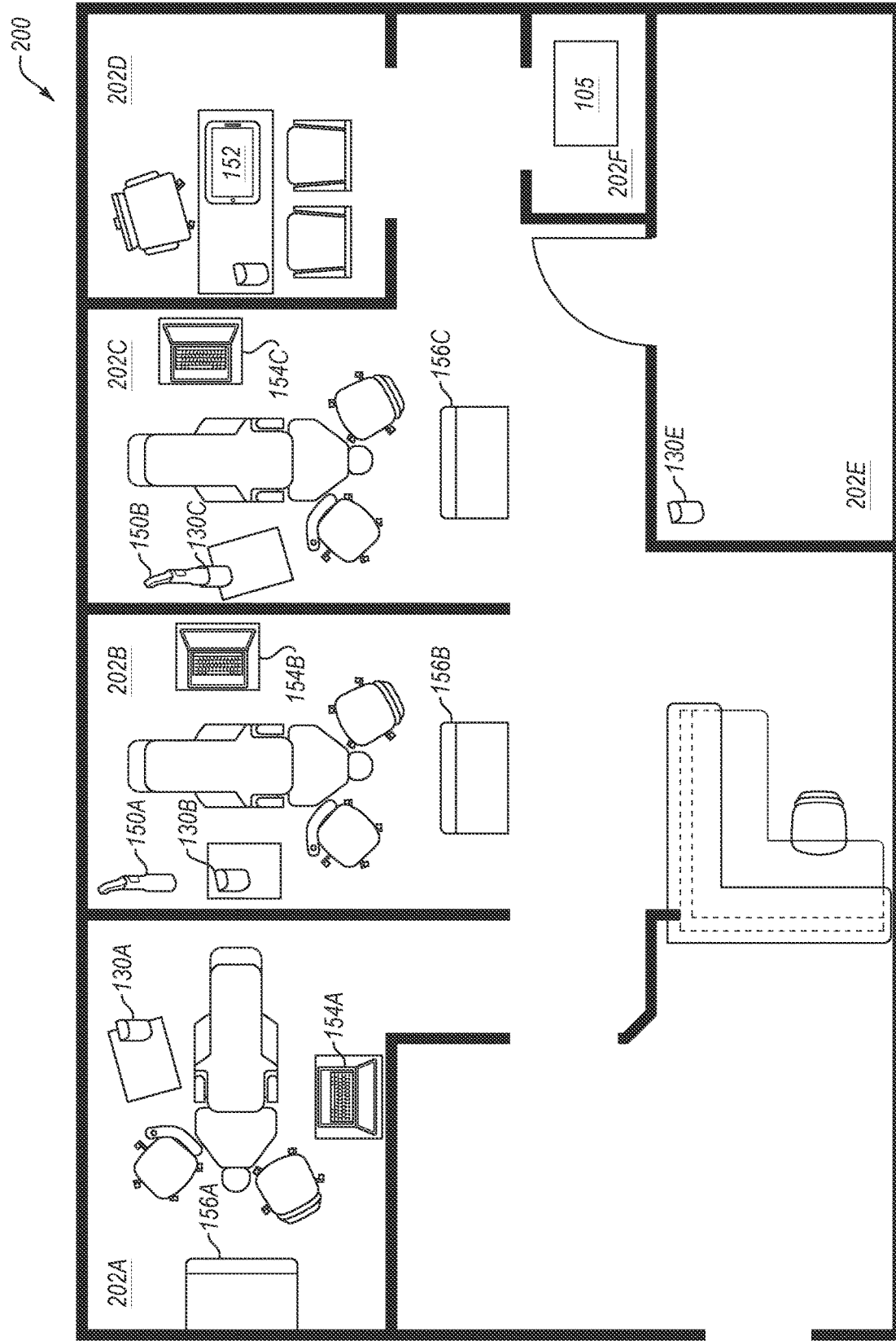
FIG. 2 illustrates an example dentist office that includes a distributed intraoral scanning system, in accordance with an embodiment.

FIG. 2 illustrates an example dentist office 200 that includes a distributed intraoral scanning system, in accordance with an embodiment. The distributed intraoral scanning system may correspond to distributed system 100 or distributed system 101 in embodiments. As shown, the dentist office 200 includes a waiting room, a receptionist area and multiple rooms 202A, 202B, 202C, 202D, 202E, 202F. Rooms 202A-202O are treatment rooms that each include a dental chair and a display 156A, 156B, 156C. The displays 156A-C may be smart TVs or may be displays of desktop computing devices in embodiments. Each treatment room 202A-C additionally is shown to include a mobile computing device 154A, 154B, 154C (e.g., a laptop computer) and a cradle 130A, 130B, 130C. Room 202D is an office, and includes a cradle 130D and a mobile computing device 152 (e.g., a tablet computer). Room 202E also includes a cradle 130E. A small storage or facilities room 202F includes local server computing device 105.

Computing device 105 may be configured to know that room 202A includes cradle 130A, room 202B includes cradle 130B, room 202C includes cradle 130C, room 202D includes cradle 130D and room 202E includes cradle 130E. The dentist office includes two intraoral scanners 150A, 150B that are both wirelessly connected to local server computing device 105. Scanner 150A may receive a first unique ID from cradle 130B, and may transmit the first unique ID to computing device 105. Computing device 105 may determine, based on the received unique ID, that scanner 150A is in room 202B. Scanner 150B may receive a second unique ID from cradle 130C, and may transmit the second unique ID to computing device 105. Computing device 105 may determine, based on the received unique ID, that scanner 150B is in room 202C. A user may request information on the location of scanner 150A and/or scanner 150B by accessing the intraoral scan application running on local server computing device 105 via any of mobile computing devices 152, 154A-C or displays 156A-C. The location information may then be sent from local server computing device 105 to the requesting device and displayed on the requesting device.

Local server computing device 105 may be wirelessly connected to both scanners 150A-B, and may receive intraoral scan data from both scanners 150A-B at the same time or at different times. Local server computing device 105 may process the intraoral scan data from both scanners 150A-B in parallel in embodiments.

Though two scanners 150A-B, four mobile computing devices 152, 154A-C and three displays 156A-B are shown, the distributed intraoral scanning system may include more or fewer scanners, displays and/or computing devices that may each wirelessly connect to local server computing device 105. Additionally, the dentist office 200 may include more or fewer cradles 130A-E. For example, some rooms may include multiple cradles and/or some rooms may not include cradles.

In one example, a doctor may generate intraoral scans of a patient in room 202A and monitor the scanning process by viewing display 156A and/or mobile computing device 154A during the scanning process. After the scanning process is complete, the doctor may move to room 202D and review the scan results via mobile computing device 152. The doctor may initiate generation of a 3D model and generation of a treatment plan from device 152, where the actual generation of the 3D model and/or treatment plan are performed on local server computing device 105. The doctor may then show the treatment plan and anticipated results of the treatment plan to the patient via device 152.

FIGS. 3A-6 illustrate methods related to intraoral scanning and generation and manipulation of virtual 3D models of dental sites using a distributed intraoral scanning system. Operations of the methods may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the methods are performed by a local server computing device executing a local intraoral scan application such as local intraoral scan application 115 of FIG. 1A.

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

Figure 3A:
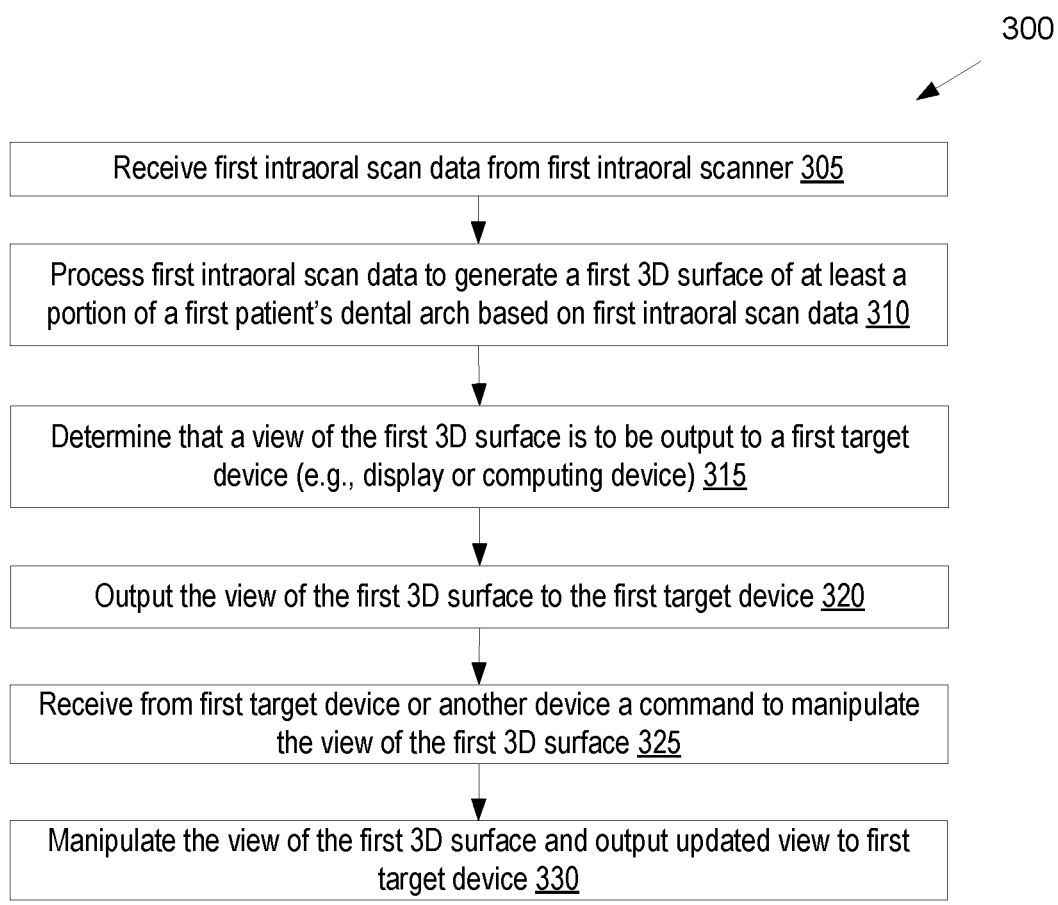
FIG. 3A illustrates a flow diagram for a method of processing intraoral scans from a handheld intraoral scanner by a computing device that is not connected to the handheld intraoral scanners via a wired connection, in accordance with an embodiment.

FIG. 3A illustrates a flow diagram for a method 300 of processing intraoral scans from a handheld intraoral scanner by a computing device that is not connected to the handheld intraoral scanners via a wired connection, in accordance with an embodiment. At operation 305 of method 300, processing logic receives first intraoral scan data from a first intraoral scanner, wherein the first intraoral scan data is of a first patient's oral cavity. The first intraoral scan data may be wirelessly received via a wireless network. The first intraoral scan data may include 2D or 3D scans, color 2D images, NIRI 2D images, and/or other images. At operation 310, processing logic processes the first intraoral scan data (e.g., 3D scans) of at least a portion of a first patient's dental arch based on the first intraoral scan data. At operation 315, processing logic determines that a view of the first 3D surface is to be output to a first target device (e.g., to a display or to a computing device). The first target device may be associated with the scanner 150 such that results of scanning are sent to the first target device. In one embodiment, the first target device is associated with the scanner 150 temporarily (e.g., for a scanning session) responsive to a user inputting a selection to receive data from the scanner 150 into the first target device.

At operation 320, processing logic outputs the view of the first 3D surface to the first target device. For example, The view of the first 3D surface may be wirelessly sent to the first target device. At operation 325, processing logic receives from the first target device or from another device a command to manipulate the view of the first 3D surface. In one embodiment, processing logic receives the command from an intraoral scanner from which the intraoral scan data was received. At operation 330, processing logic manipulates the view of the first 3D surface and outputs the updated view of the first 3D surface to the first target device.

Figure 3B:
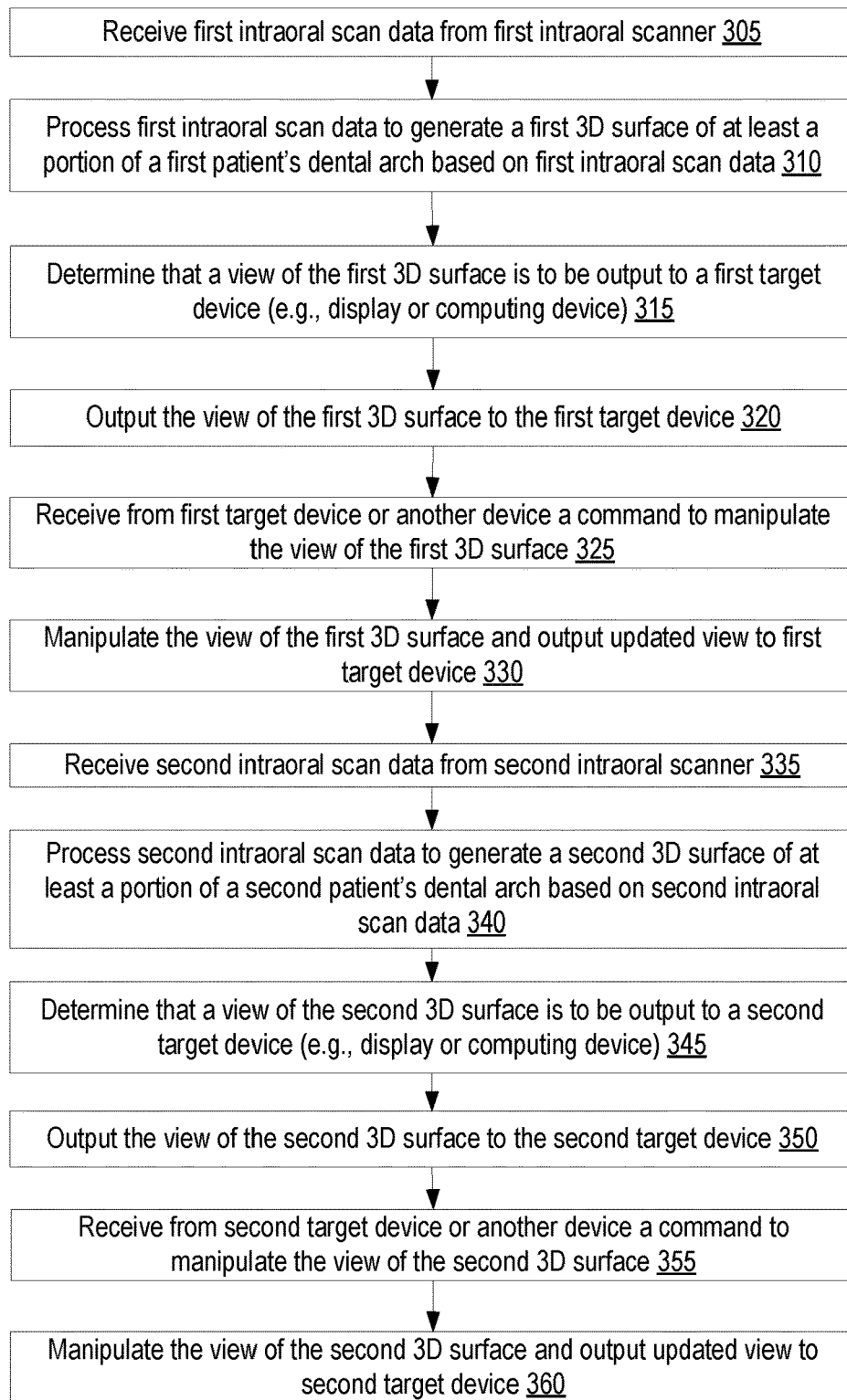
FIG. 3B illustrates a flow diagram for a method of processing intraoral scans from two different handheld intraoral scanners by a computing device that is not connected to the handheld intraoral scanners via a wired connection, in accordance with an embodiment.

FIG. 3B illustrates a flow diagram for a method 302 of processing intraoral scans from two different handheld intraoral scanners by a computing device that is not connected to the handheld intraoral scanners via a wired connection, in accordance with an embodiment. Method 302 is similar to method 300, and includes some of the same operations as method 300. However, method 302 includes receiving and processing intraoral scan data from multiple intraoral scanners, where the data from the multiple intraoral scanners may be received in parallel (and processed in parallel) or may be received in series (and processed in series).

At operation 305 of method 302, processing logic receives first intraoral scan data from a first intraoral scanner, wherein the first intraoral scan data is of a first patient's oral cavity. The first intraoral scan data may be wirelessly received via a wireless network. The first intraoral scan data may include 2D or 3D scans, color 2D images, NIRI 2D images, and/or other images. At operation 310, processing logic processes the first intraoral scan data (e.g., 3D scans) of at least a portion of a first patient's dental arch based on the first intraoral scan data. At operation 315, processing logic determines that a view of the first 3D surface is to be output to a first target device (e.g., to a display or to a computing device). The first target device may be associated with the scanner 150 such that results of scanning are sent to the first target device. In one embodiment, the first target device is associated with the scanner 150 temporarily (e.g., for a scanning session) responsive to a user inputting a selection to receive data from the scanner 150 into the first target device.

At operation 320, processing logic outputs the view of the first 3D surface to the first target device. For example, The view of the first 3D surface may be wirelessly sent to the first target device, for example. At operation 325, processing logic receives from the first target device or from another device a command to manipulate the view of the first 3D surface. In one embodiment, processing logic receives the command from an intraoral scanner from which the intraoral scan data was received. At operation 330, processing logic manipulates the view of the first 3D surface and outputs the updated view of the first 3D surface to the first target device.

At operation 335, processing logic receives second intraoral scan data from a second intraoral scanner, wherein the second intraoral scan data is of a second patient's oral cavity. The second intraoral scan data may be wirelessly received via a wireless network. The second intraoral scan data may include 2D or 3D scans, color 2D images, NIRI 2D images, and/or other images. At operation 340, processing logic processes the second intraoral scan data (e.g., 3D scans) of at least a portion of a second patient's dental arch based on the second intraoral scan data. At operation 345, processing logic determines that a view of the second 3D surface is to be output to a second target device (e.g., to a display or to a computing device). The second target device may be associated with the second scanner such that results of scanning are sent to the second target device. In one embodiment, the second target device is associated with the second scanner temporarily (e.g., for a scanning session) responsive to a user inputting a selection to receive data from the second scanner into the second target device.

At operation 350, processing logic outputs the view of the second 3D surface to the second target device. For example, The view of the second 3D surface may be wirelessly sent to the second target device, for example. At operation 355, processing logic receives from the second target device or from another device a command to manipulate the view of the second 3D surface. In one embodiment, processing logic receives the command from an intraoral scanner from which the intraoral scan data was received. At operation 360, processing logic manipulates the view of the second 3D surface and outputs the updated view of the second 3D surface to the second target device.

Figure 4:
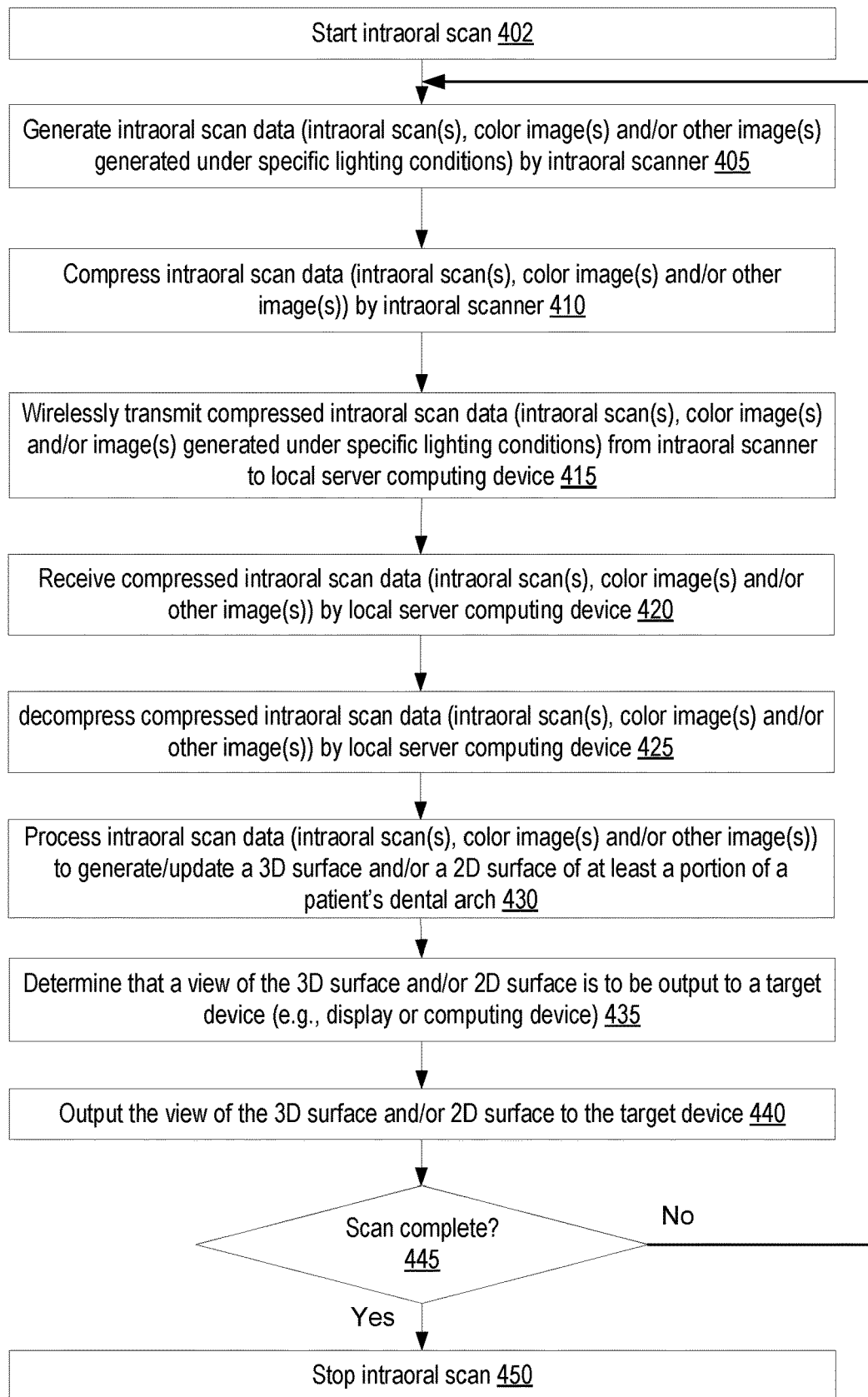
FIG. 4 illustrates a flow diagram for a method of performing intraoral scanning using a distributed intraoral scanning system, in accordance with an embodiment.

FIG. 4 illustrates a flow diagram for a method 400 of performing intraoral scanning using a distributed intraoral scanning system, in accordance with an embodiment. At operation 402 of method 400, an intraoral scanner starts an intraoral scan. At operation 405, the intraoral scanner generates intraoral scan data, which may include intraoral scans, color images and/or other images generated under specific lighting conditions (e.g., under infrared or near-infrared light). At operation 410, the intraoral scanner compresses the intraoral scan data. In one embodiment, video compression techniques are used to compress the intraoral scan data. Compressing the intraoral scan data may include compressing intraoral scans, compressing color images and/or compressing near-infrared images. Additionally, or alternatively, the intraoral scanner may perform reduction on the intraoral scan data (e.g., on intraoral scans) by identifying areas of interest and cropping intraoral scans to include only the areas of interest. At operation 415, the intraoral scanner wirelessly transmits the compressed and/or reduced intraoral scan data to a local server computing device.

At operation 420, the local server computing device receives the compressed and/or reduced intraoral scan data. At operation 425, the local server computing device decompresses the compressed intraoral scan data (if it was compressed). For example, the local server computing device may decompress compressed scans, compressed color images and/or compressed near-infrared images. At operation 430, the local server computing device processes the intraoral scan data (e.g., intraoral scans, color images and/or other images) to generate or update a 3D surface and/or a 2D surface of at least a portion of a patient's dental arch. At operation 435, the local server computing device determines that a view of the 3D surface and/or 2D surface is to be output to a target device (e.g., to a display or computing device). At operation 440, the local server computing device outputs the view of the 3D surface and/or 2D surface to the target device. In one embodiment, a view of the 3D surface that includes data from multiple intraoral scans is output to the target device. The 3D surface may represent a portion of the patient's dental arch that has thus far been scanned. In one embodiment, a copy of a viewfinder image (e.g., a color 2D image) is also output to the target device, where the viewfinder image may represent a current field of view of the intraoral scanner.

At operation 445, the local server computing device determines whether the scan is complete. The scan may be determined to be complete responsive to a command from the intraoral scanner to exit a scanning mode, for example. If the scan is not complete, the method returns to operation 405 and scanner generates additional intraoral scan data. The additional intraoral scan data may be processed to generate an updated 3D surface, and a view of the updated 3D surface may be output to the first target device. While scanning continues, processing logic may continually receive new intraoral scan data and may continually update the first 3D surface of at least the portion of the first patient's dental arch as further intraoral scans are received. Processing logic may stream updates to the view of the first 3D surface of at least the portion of the first patient's dental arch as the first 3D surface is updated. Thus, the doctor may view scan progress in real time or near-real time as the scanning commences. Additionally, a viewfinder image may be received from the intraoral scanner (e.g., as one component of the intraoral scan data), and may be streamed to the first target device. Thus, the doctor may additionally be provided with an up-to-date view of the field of view of the scanner. If the scan is complete, the method continues to operation 450, and the scan is stopped. At any time a user may resume the scan by sending a commend to start scanning again.

Figure 5:
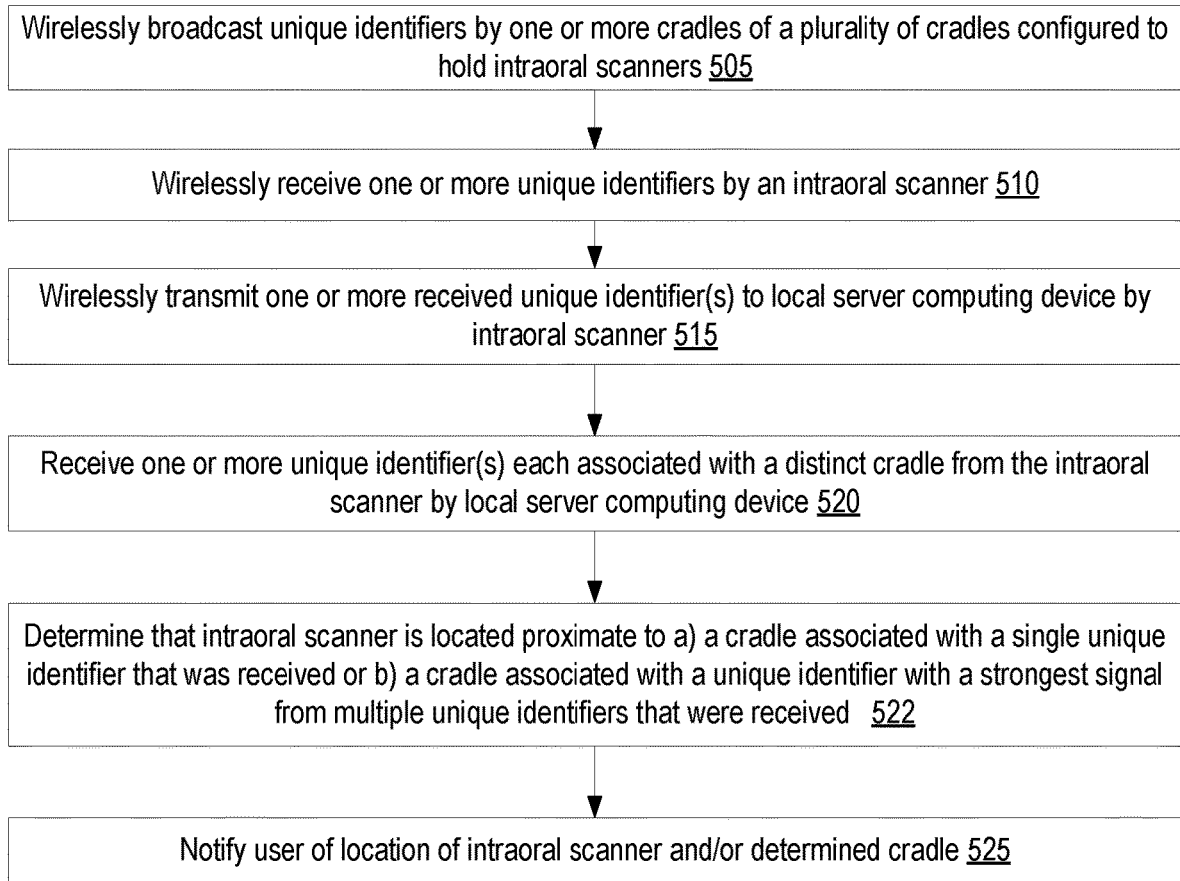
FIG. 5 illustrates a flow diagram for a method of locating a wireless intraoral scanner, in accordance with an embodiment.

FIG. 5 illustrates a flow diagram for a method 500 of locating a wireless intraoral scanner, in accordance with an embodiment. At operation 505 of method 500, one or more cradles each wirelessly broadcasts a unique identifier. Each of the cradles may be a cradle for an intraoral scanner. At operation 510, the intraoral scanner wirelessly receives one or more unique identifiers that were broadcast by cradles. At operation 515, the intraoral scanner wirelessly transmits one or more received unique identifiers to a local server computing device.

At operation 520, the local server computing device receives one or more unique identifiers from the intraoral scanner. Each unique identifier may be associated with a particular cradle. At operation 522, the local server computing device determines a location of the intraoral scanner based on the received unique identifiers. In one embodiment, the local server computing device receives a single unique identifier from the intraoral scanner, and determines that the intraoral scanner is located proximate to a cradle associated with the single unique identifier that was received. In one embodiment, the local server computing device receives multiple unique identifiers each associated with a different signal strength, and determines that the intraoral scanner is proximate to a cradle having with a unique identifier associated with a strongest signal strength. Alternatively, local server computing device may perform triangulation based on multiple signals and known positions of the cradles that output those signals to determine a location of the intraoral scanner. At operation 525, the local server computing device notifies a user of a location of the intraoral scanner and/or the determined cradle to which the intraoral scanner is proximate. The notification may be performed by outputting an indication of the location to a display or computing device that requested a location of the scanner, for example.

Figure 6:
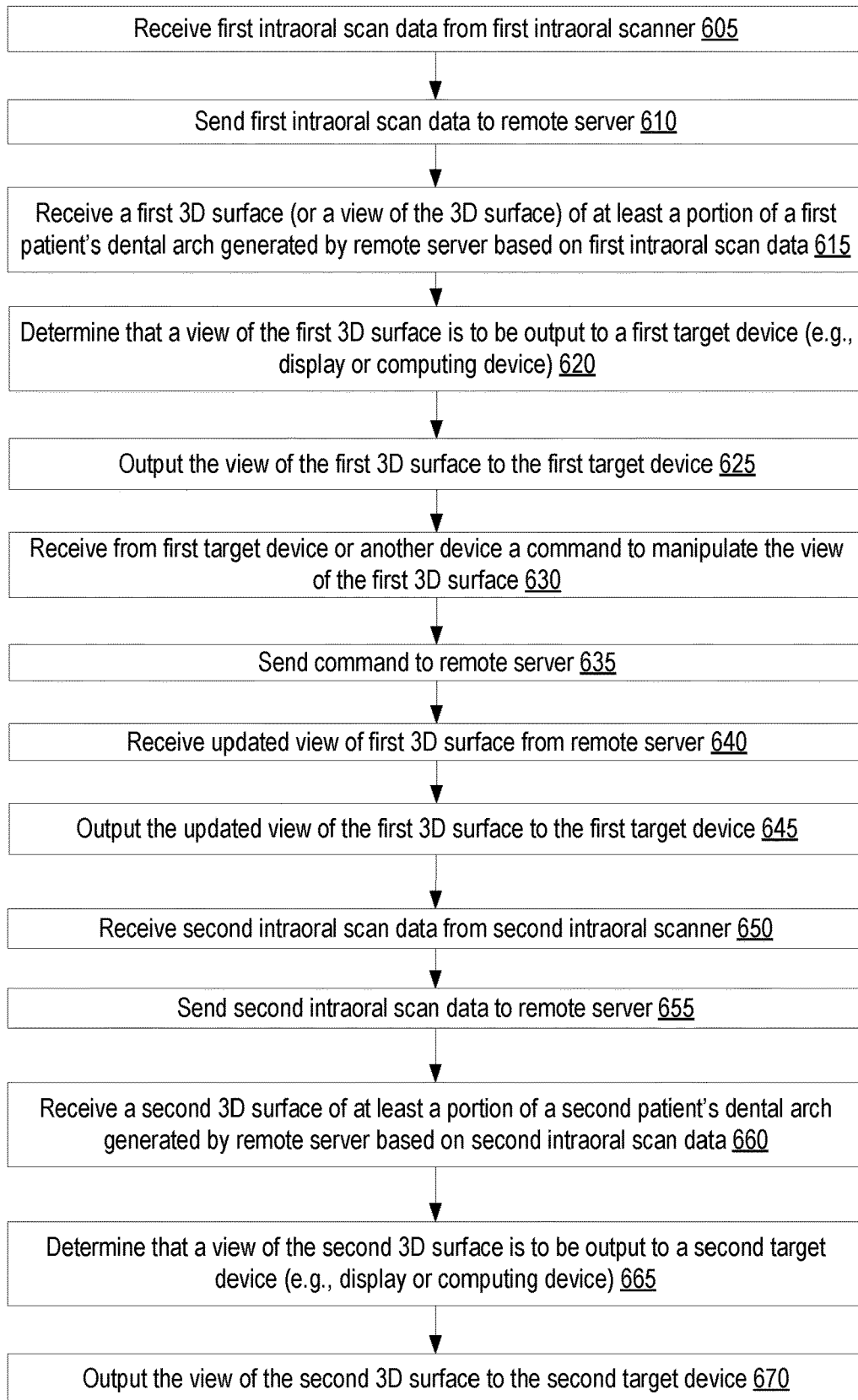
FIG. 6 illustrates a flow diagram for a method of processing intraoral scan data during intraoral scanning using a cloud-based server, in accordance with an embodiment.

FIG. 6 illustrates a flow diagram for a method 600 of processing intraoral scan data during intraoral scanning using a cloud-based server, in accordance with an embodiment. At operation 605 of method 600, processing logic receives first intraoral scan data from a first intraoral scanner, wherein the first intraoral scan data is of a first patient's oral cavity. The first intraoral scan data may be wirelessly received via a wireless network. The first intraoral scan data may include 2D or 3D scans, color 2D images, NIRI 2D images, and/or other images. At operation 610, processing logic sends the intraoral scan data to a remote server. At operation 615, processing logic receives a first 3D surface (or a view of a first 3D surface) of at least a portion of a first patient's dental arch that was generated by the remote server based on the first intraoral scan data. At operation 620, processing logic determines that a view of the first 3D surface is to be output to a first target device (e.g., to a display or to a computing device). The first target device may be associated with a scanner such that results of scanning are sent to the first target device. In one embodiment, the first target device is associated with the scanner temporarily (e.g., for a scanning session) responsive to a user inputting a selection to receive data from the scanner into the first target device.

At operation 625, processing logic outputs the view of the first 3D surface to the first target device. For example, The view of the first 3D surface may be wirelessly sent to the first target device, for example. At operation 630, processing logic receives from the first target device or from another device a command to manipulate the view of the first 3D surface. In one embodiment, processing logic receives the command from an intraoral scanner from which the intraoral scan data was received. At operation 635, processing logic may send a command to the remote server to manipulate the view of the first 3D surface. At operation 640, processing logic may receive an updated view of the first 3D surface after the remote server has manipulated the view in accordance with the command. Alternatively, rather than performing the operations of 635 and 640, processing logic may manipulate the view of the first 3D surface locally. At operation 645, processing logic outputs the updated view of the first 3D surface to the first target device.

At operation 650, processing logic receives second intraoral scan data from a second intraoral scanner, wherein the second intraoral scan data is of a second patient's oral cavity. The second intraoral scan data may be wirelessly received via a wireless network. The second intraoral scan data may include 2D or 3D scans, color 2D images, NIRI 2D images, and/or other images. At operation 655, processing logic sends the second intraoral scan data to the remote server. At operation 660, processing logic receives a second 3D surface of at least a portion of a second patient's dental arch that was generated by the remote server based on the second intraoral scan data. At operation 665, processing logic determines that a view of the second 3D surface is to be output to a second target device (e.g., to a display or to a computing device). The second target device may be associated with the second scanner such that results of scanning are sent to the second target device. In one embodiment, the second target device is associated with the second scanner temporarily (e.g., for a scanning session) responsive to a user inputting a selection to receive data from the second scanner into the second target device.

At operation 670, processing logic outputs the view of the second 3D surface to the second target device. For example, The view of the second 3D surface may be wirelessly sent to the second target device.

Figure 7A:
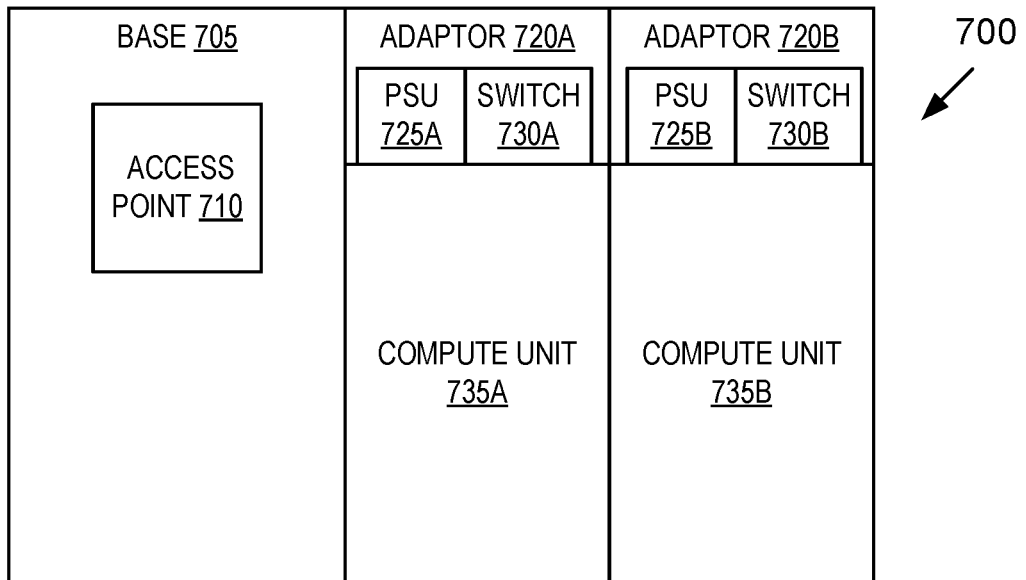
FIGS. 7A-C illustrate a computing device that functions as a local server for a distributed intraoral scanning system, in accordance with an embodiment.
Figure 7B:
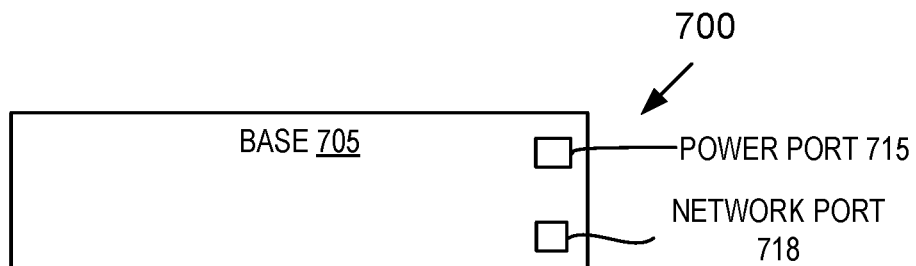
Figure 7C:
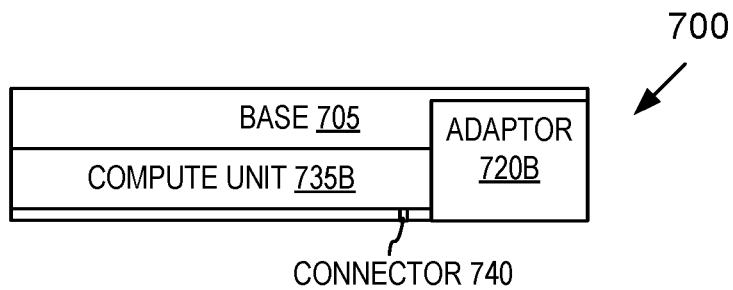

FIGS. 7A-C illustrate a computing device 700 that functions as a local server for a distributed intraoral scanning system, in accordance with an embodiment. FIG. 7A illustrates a top view of the computing device 700. FIG. 7B illustrates a left side view of the computing device 700. FIG. 7C illustrates a right side view of the computing device 700.

In one embodiment, computing device 700 is a modular computing server system designed to provide computing service for a flexible number of intraoral scanners. Computing device 700 may include a base 705 and one or more adaptors 720A-B. Base 705 may include a wireless access point 710 (e.g., a Wi-Fi access point or module), and/or may include a network port 718 (e.g., an Ethernet port 718) for connecting to a wireless access point or wireless router. Base 705 may additionally include a power port 715 for connecting to a power outlet. Each adaptor 720A-B may include a dedicated power supply unit (PSU) 725A-B and a network switch (e.g., an Ethernet switch). In one embodiment, the adaptors 720A-B are daisy chained to the base 705 with power cables or power connectors and/or network cables (e.g., Ethernet cables). Thus, each adaptor 720A-B may be connected to access point 710 and/or network port 718 as well as to power port 715.

Each of the adaptors 720A-B may be configured to receive a single compute unit 735A-B, which may be removably coupled to an adaptor 720A-B. Each compute unit may include one or more processors and/or memory, and may be responsible for performing operations on intraoral scan data from one or a few intraoral scanners. For example, compute unit 735A may be associated with a first intraoral scanner and may process intraoral scan data from the first intraoral scanner, and compute unit 735B may be associated with a second intraoral scanner and may process intraoral scan data from the second intraoral scanner. Similarly, the first compute unit 735A may send first image data to a first target device (e.g., a first display) associated with the first intraoral scanner, and second compute unit 735B may send second image data to a second target device (e.g., a second display) associated with the second intraoral scanner. Additionally, the first compute unit 735A may receive commands from a first computing device associated with the first intraoral scanner to control a first instance of an intraoral scan application executing on the first compute unit, and second compute unit 735B may receive commands from a second device associated with the second intraoral scanner to control a second instance of an intraoral scan application executing on the second compute unit. In one embodiment, each compute unit has its own dedicated network address (e.g., its own internet protocol (IP) address, which may be a dynamic or static IP address).

As shown, the computing device 700 includes two adaptors 720A-B, each with a compute unit 735A-B attached to the respective adaptor 720A-B. However, in other embodiments the computing device 700 may include more than two adaptors (e.g., may include 3, 4, 5, 6 or more adaptors). A customer may select how many adaptors they want and/or how many compute units that they want in embodiments. Each compute unit 735A-B may be designed to perform processing for one or a few intraoral scanners. Thus, a dental office that has only one scanner may use a computing device 700 with a single compute unit 735A. However, a dental office that has 3 scanners may use a computing device 700 with two compute units 735A-B. A dental office may order a computing device 700 with a single compute unit 735A and with one or more empty adaptors. If at some point the dental office expands and adds additional intraoral scanners to their system, then they may order an additional compute unit 735B to add to an empty adaptor to increase the capacity of their computing device 700.

In one embodiment, each adaptor 720A-B includes a connector 740 that is usable to connect a compute unit 735A-B to the adaptor 720A-B. The compute unit 735A-B may be removable from the adaptor via a single action, and may be insertable into the adaptor or another adaptor of the same computing device 700 or a different computing device via a single action. The single connector may be a breakaway connector that provides power and data connections between the compute unit and the adaptor. A compute unit may be inserted and/or removed from a computing device by a simple push/pull action, and may be moved between offices, for example, while leaving the computing device 700 stationary.

Figure 8:
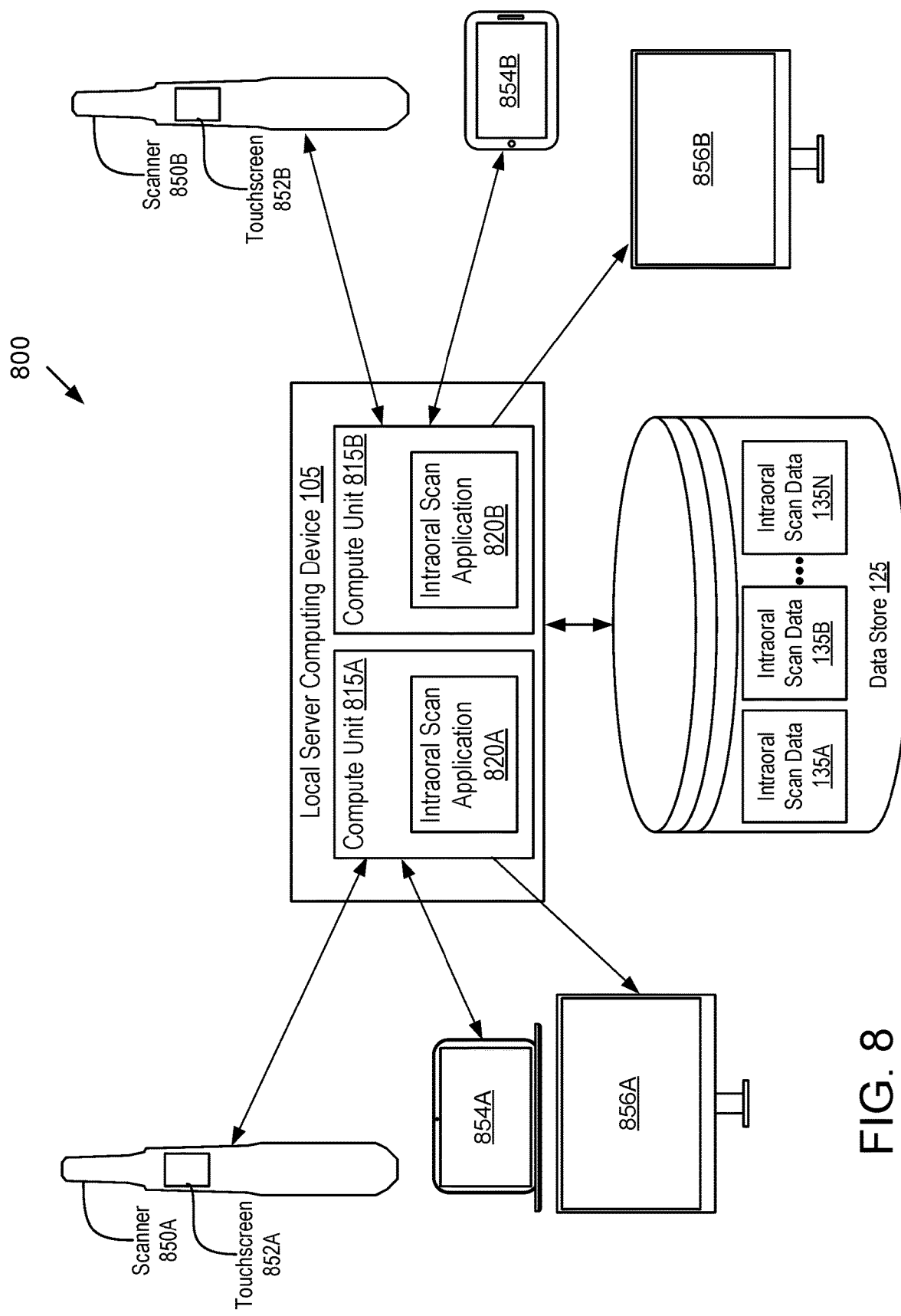
FIG. 8 illustrates a distributed system for performing intraoral scanning and/or generating a virtual three-dimensional model of an intraoral site, in accordance with an embodiment.

FIG. 8 illustrates a distributed system 800 for performing intraoral scanning and/or generating a virtual three-dimensional model of an intraoral site, in accordance with an embodiment. Distributed system 800 includes scanners 850A-B, local server computing device 105, peripheral computing devices 854A-B, and displays 856A-B. Distributed system 800 may further include a remote server computing device (not shown). Local server computing device 105 may correspond to local server computing device 700 of FIGS. 7A-C in embodiments. For example, local server computing device may include multiple compute units 815A-B. Though two compute units are shown, it should be understood that in alternative embodiments, local server computing device 105 may include only a single compute unit or may include more than two compute units. Each compute unit 815A-B may include its own instance of an intraoral scan application 820A-B. Each compute unit 815A-B and intraoral scan application 820A-B may be configured to work with a single intraoral scanner at a time in some embodiments. In some embodiments, a single compute unit may be configured to work with multiple intraoral scanners in parallel. For example, a compute unit may implement multi-tenancy and/or virtualization to segregate interactions with different intraoral scanners. If virtualization is used, then a single compute unit may include a hypervisor on which multiple virtual compute units may reside. Each virtual compute unit may include its own distinct instance of the intraoral scan application.

Distributed system 800 may substantially correspond to distributed system 100 of FIG. 1A in embodiments, except that distributed system 800 shows one embodiment in which local server computing device 105 includes multiple compute units 815A-B, each of which handles intraoral scanning tasks for a different intraoral scanner 850A-B. For example, local server computing device 105 may be connected to data store 125, and may store intraoral scan data 135A-N as discussed with reference to FIG. 1A.

Compute unit 815A and/or intraoral scan application 820A establishes connections to intraoral scanner 850A, peripheral computing device 854A and display device 856A. Compute unit 815A and/or intraoral scan application 820A may associate scanner 850A, peripheral computing device 854A and display device 856A together. Accordingly, intraoral scan data may be sent from scanner 850A to compute unit 815A. Intraoral scan application 820A may process the intraoral scan data to generate a 3D surface, and may send the 3D surface or a view of the 3D surface to peripheral computing device 854A and/or display device 856A, and a doctor may monitor the progress of intraoral scanning based on review of the 3D surface shown on the peripheral computing device 854A and/or display device 856A.

Scanner 850A may include a touchscreen 852A, and intraoral scan application 820A may send data to be displayed on the touchscreen 852A during an intraoral scanning session. The data to be displayed on touchscreen 852A may include virtual buttons, a virtual keypad, a full or partial view of the 3D surface, a viewfinder image, a portion of a viewfinder image, and/or other data. The data to be displayed on touchscreen 852A may be still data (e.g., buttons, menus, icons, etc.) and/or moving data (e.g., video). A user may interface with the touchscreen (e.g., by pressing a virtual button), and the scanner 850A may send control signals to intraoral scan application 820A based on such user interaction with the touchscreen. The control signals may cause the intraoral scan application to change a view of a 3D surface or 3D model, to change to a different scanning segment (e.g., upper dental arch segment, lower dental arch segment, bite segment, preparation tooth segment, etc.), change to a different mode, and so on. A user may additionally or alternatively interface with one or more inputs (e.g., a mouse, touchpad, keyboard, etc.) of peripheral computing device 854A to control the intraoral scan application 820A.

Compute unit 815B and/or intraoral scan application 820B establishes connections to intraoral scanner 850B, peripheral computing device 854B and display device 856B. Compute unit 815B and/or intraoral scan application 820B may associate scanner 850B, peripheral computing device 854B and display device 856B together. Accordingly, intraoral scan data may be sent from scanner 850B to compute unit 815B. Intraoral scan application 820B may process the intraoral scan data to generate a 3D surface, and may send the 3D surface or a view of the 3D surface to peripheral computing device 854B and/or display device 856B, and a doctor may monitor the progress of intraoral scanning based on review of the 3D surface shown on the peripheral computing device 854B and/or display device 856B. Each of these operations may be performed in parallel to operations performed by compute unit 815A for intraoral scanner 850A, peripheral computing device 854A and display device 856A. Scanner 850B may include a touchscreen 852B, and intraoral scan application 820B with may operate as described with reference to touchscreen 852A.

There are multiple different techniques that may be implemented for pairing or connecting intraoral scanners, peripheral computing devices and/or display devices to a local server computing device in embodiments. Embodiments covering a few such techniques are discussed below.

Figure 9A:
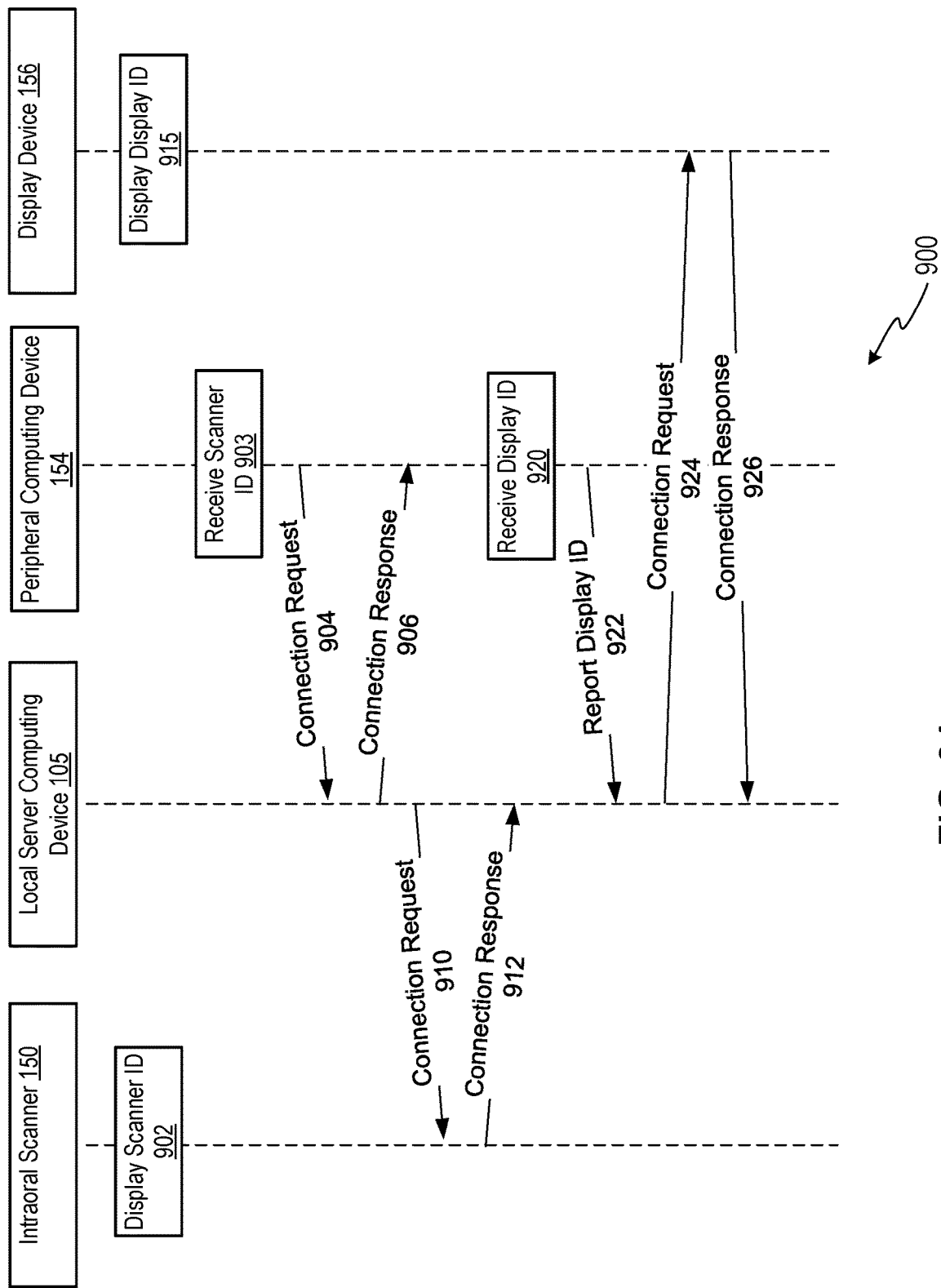
FIG. 9A is a sequence diagram illustrating pairing of an intraoral scanner, a peripheral computing device and a display device to a local server computing device, in accordance with embodiments of the present disclosure.

FIG. 9A is a sequence diagram illustrating a method 900 of pairing and synchronization of an intraoral scanner 150, a peripheral computing device 154 and optionally a display device 156 to a local server computing device 105, in accordance with embodiments of the present disclosure. At block 902, intraoral scanner 150 may display an identifier (ID) of the intraoral scanner 150. The identifier may be a unique identifier assigned to the intraoral scanner 150 that can be used to identify the intraoral scanner 150. In one embodiment, the identifier is a permanent value such as a serial number of the intraoral scanner 150 that may have been assigned at a time of manufacture. In one embodiment, the identifier is an identifier that was previously assigned to the intraoral scanner 150 by local server computing device 105. The identifier may be displayed on a display of the intraoral scanner, which may include a touchscreen and/or a display that is not touch sensitive, such as a small liquid crystal display (LCD) display. In one embodiment, the displayed scanner ID is a code such as a one-dimensional or two-dimensional barcode.

At block 903, peripheral computing device 154 may receive the displayed scanner ID, which may be performed after a doctor chooses a "connect to intraoral scanner" option in the peripheral computing device 154. In one embodiment, a user reads the scanner ID from the scanner, and inputs the scanner ID into the peripheral computing device (e.g., using a keyboard of the peripheral computing device). In one embodiment, the peripheral computing device 154 includes a camera, which may be used to capture an image of the scanner ID displayed on the scanner 150. The peripheral computing device may, for example, scan a quick response (QR) code or another matrix barcode and determine a numerical identifier from the scanned QR or matrix barcode. Alternatively, if the identifier is an alphanumeric code or numeric code, then the peripheral computing device may perform optical character recognition (OCR) to identify the scanner ID.

In some embodiments, intraoral scanner 150 includes a wireless module that periodically or continuously broadcasts a signal that includes a unique identifier of the intraoral scanner. Each intraoral scanner may send or broadcast a different unique identifier than other intraoral scanners. Peripheral computing device 154 may receive signals broadcast or sent by scanner 150. In one embodiment, the signal broadcast by intraoral scanner may be a low power signal that is detected by peripheral computing device 154 if the scanner is within a threshold distance from peripheral computing device. Accordingly, the peripheral computing device 154 may detect a signal from intraoral scanner, and report the unique identifier included in the signal to computing device 105. In one embodiment, the low power signal output by the intraoral scanner is a signal corresponding to a low energy unidirectional wireless protocol (e.g., the iBeacon® protocol or other Bluetooth® low energy (BLE) protocol) to transmit information usable to identify the intraoral scanning system display adapter. In one embodiment, the signal broadcast by intraoral scanner is a Bluetooth signal, a Zigbee signal, a Wi-Fi signal, or a signal broadcast according to another wireless protocol.

In one embodiment, peripheral computing device 154 includes a radio frequency identification (RFID) or near field communication (NFC) reader, and periodically broadcasts a signal to read RFID or NFC chips. Intraoral scanner may include a unique RFID or NFC identifier, and upon receiving an RFID or NFC reading signal, may respond by emitting a unique identifier. Peripheral computing device 154 may then report the unique identifier to computing device 105, which may determine an intraoral scanner to associate with the peripheral computing device 154 based on the unique ID as discussed above. Alternatively, intraoral scanner 150 may include an RFID or NFC reader, which may read an RFID or NFC chip on peripheral computing device 154, and may include a Wi-Fi module to wirelessly connect to computing device 105 and report on a received signal from peripheral computing device 154.

The peripheral computing device 154 may query the local server computing device 105 (e.g., via background polling) to determine one or more available compute units of the local server computing device 105 that are available. In one embodiment, peripheral computing device 154 performs polling of the local server computing device 105 periodically to determine available compute units. The peripheral computing device may receive one or more response indicating one or more available compute units. At block 904, peripheral computing device sends a connection request to local server computing device 105. In one embodiment, the connection request is a request to associate the peripheral computing device with the intraoral scanner, which may be one of a plurality of intraoral scanners. The connection request may be sent to a particular available compute unit and/or may include an identifier of the available compute unit. The connection request may additionally or alternatively include an identifier of the peripheral computing device and the received scanner ID of the intraoral scanner 150. In one embodiment, the connection is initialized with the compute unit using remote desktop protocol (RDP).

At block 906, the local server computing device may send a connection response to peripheral computing device, indicating that a connection has been established. At block 910, local server computing device 105 may send a connection request to intraoral scanner 150 using the received scanner ID associated with the intraoral scanner 150. The intraoral scanner 150 may send a connection response at block 912, after which the local server computing device may be connected to the intraoral scanner. At this point, a particular compute unit of local server computing device 105 may be connected to peripheral computing device 154 and intraoral scanner 150, and each of the compute unit of the local server computing device, the intraoral scanner 150 and the peripheral computing device 154 may be associated with one another in an intraoral scan application.

In some embodiments, display device 156 displays a display identifier of display device 156 at block 915. The display ID may be a unique identifier usable to identify display device, and may be a permanent ID (e.g., a serial number) or a temporary ID previously assigned by local server computing device 105. At block 920, peripheral computing device 154 may receive the display ID. For example, a user may manually input the display ID into the peripheral computing device 154, or the peripheral computing device may include a camera that captures an image of the identifier (e.g., one-dimensional or two-dimensional bar code, or alphanumeric code) displayed by the display device 156.

Note that reference above to connections established between local server computing device 105 and a display device 156 include direct connections between the local server computing device and the display device as well as connections between the local server computing device 105 and an intraoral scanning system display adapter or digital media player plugged into a data input of display device 156. For example, an intraoral scanning system display adapter may be connected to a television via an RCA cable, an high definition multimedia interface (HDMI) cable, an optical cable, a universal serial bus (USB) cable, or other audio/video or data cable. In one embodiment, the intraoral scanning system display adapter is a USB dongle that plugs into a USB port of a television. If the connection to the display device 156 is actually a connection to an intraoral scanning system display adapter or a digital media player plugged into a display device, then the display ID that is displayed on the display device and used to connect to the display device may actually be an ID of the intraoral scanning system display adapter or the digital media player.

In some embodiments, an intraoral scanning system display adapter as previously discussed herein includes a wireless module that periodically or continuously broadcasts a signal that includes a unique identifier of the display device or of the intraoral scanning system display adapter. Additionally, or alternatively, a display device may include such a wireless module. Each intraoral scanning system display adapter or display device may send or broadcast a different unique identifier than other intraoral scanning system display adapters and/or display devices. Peripheral computing device 154 may receive signals broadcast or sent by one or more intraoral scanning system display adapter and/or display device depending on a location of scanner 150. In one embodiment, the signal broadcast by each intraoral scanning system display adapter and/or display device may be a low power signal that is detected by peripheral computing device 154 if the peripheral computing device is within a threshold distance from an intraoral scanning system display adapter or display device. Accordingly, the peripheral computing device 154 may detect a signal from a intraoral scanning system display adapter or display device, and report the unique identifier included in the signal to computing device 105. In one embodiment, the low power signal output by the intraoral scanning system display adapter or display device is a signal corresponding to a low energy unidirectional wireless protocol (e.g., the iBeacon® protocol or other Bluetooth® low energy (BLE) protocol) to transmit information usable to identify the intraoral scanning system display adapter or display device.

In one embodiment, the signal broadcast by each intraoral scanning system display adapter or display device is a Bluetooth signal, a Zigbee signal, a Wi-Fi signal, or a signal broadcast according to another wireless protocol. The intraoral scanning system display adapter or display device may broadcast signals that are powerful enough such that peripheral computing device 154 may receive signals from display adapters and/or display devices. Peripheral computing device 154 may report the received signals as well as signal strengths, time of flight, delay, angle of signals, etc. of the received signals to computing device 105. Computing device 105 may then use the received information to determine which of multiple intraoral scanning system display adapters and/or display devices should be associated with peripheral computing device 154. In one embodiment, peripheral computing device 154 is determined to be proximate to an intraoral scanning system display adapter or display device associated with a strongest signal strength.

In one embodiment, peripheral computing device 154 includes a radio frequency identification (RFID) or near field communication (NFC) reader, and periodically broadcasts a signal to read RFID or NFC chips. Each intraoral scanning system display adapter and/or display device may include a unique RFID or NFC identifier, and upon receiving an RFID or NFC reading signal, may respond by emitting a unique identifier. Peripheral computing device 154 may then report the unique identifier to computing device 105, which may determine an intraoral scanning system display adapter or display device to associate with the peripheral computing device based on the unique ID as discussed above. Alternatively, each intraoral scanning system display adapter and/or display device may include an RFID or NFC reader, which may read an RFID or NFC chip on peripheral computing device 154, and may include a Wi-Fi module to wirelessly connect to computing device 105 and report on a received signal from a peripheral computing device 154.

Peripheral computing device 154 may report the display ID to local server computing device 105 at block 922. Local server computing device 105 may then send a connection request to display device using the received display ID at block 924. In one embodiment, local server computing device 105 broadcasts a connection message that includes the display device's display ID. At block 926, the display device 156 may send a connection response to local server computing device 105, causing a connection to be established between the local server computing device (e.g., the compute unit of the local server computing device) and the display device 156. In one embodiment, a web application or native application running on the display device receives a broadcast message that includes the display ID, and then uses an IP address of the local computing device (which may be indicated in the received broadcast message) to connect to the local computing device 154. The display device may then start receiving a video stream (e.g., a WebRTC video stream). The display device may then be associated with the compute unit of the local server computing device 105, the intraoral scanner 150, and the peripheral computing device 154.

Figure 9B:
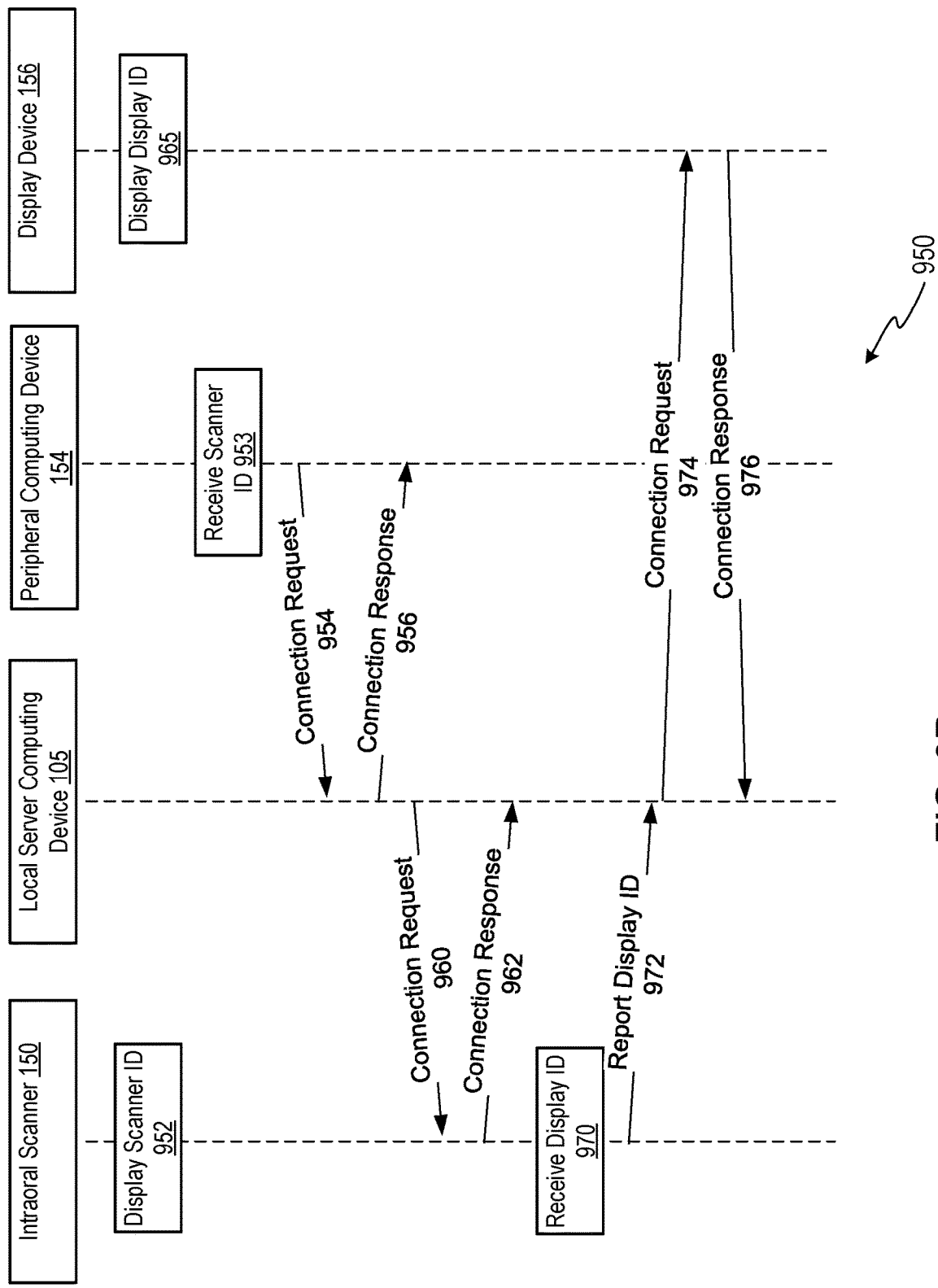
FIG. 9B is another sequence diagram illustrating pairing of an intraoral scanner, a peripheral computing device and a display device to a local server computing device, in accordance with embodiments of the present disclosure.

FIG. 9B is another sequence diagram illustrating a method 950 of pairing and synchronization of an intraoral scanner 150, a peripheral computing device 154 and optionally a display device 156 to a local server computing device 105, in accordance with embodiments of the present disclosure. At block 952, intraoral scanner 150 may display an identifier (ID) of the intraoral scanner 150. The identifier may be a unique identifier assigned to the intraoral scanner 150 that can be used to identify the intraoral scanner 150. In one embodiment, the identifier is a permanent value such as a serial number of the intraoral scanner 150 that may have been assigned at a time of manufacture. In one embodiment, the identifier is an identifier that was previously assigned to the intraoral scanner 150 by local server computing device 105. The identifier may be displayed on a display of the intraoral scanner, which may include a touchscreen and/or a display that is not touch sensitive, such as a small liquid crystal display (LCD) display. In one embodiment, the displayed scanner ID is a code such as a one-dimensional or two-dimensional barcode.

At block 953, peripheral computing device 154 may receive the displayed scanner ID. In one embodiment, a user reads the scanner ID from the scanner, and inputs the scanner ID into the peripheral computing device (e.g., using a keyboard of the peripheral computing device). In one embodiment, the peripheral computing device 154 includes a camera, which may be used to capture an image of the scanner ID displayed on the scanner 150. The peripheral computing device may, for example, scan a quick response (QR) code or another matrix barcode and determine a numerical identifier from the scanned QR or matrix barcode. Alternatively, if the identifier is an alphanumeric code or numeric code, then the peripheral computing device may perform optical character recognition (OCR) to identify the scanner ID.

The peripheral computing device 154 may query the local server computing device 105 to determine one or more available compute units of the local server computing device 105 that are available. The peripheral computing device may receive one or more response indicating one or more available compute units. At block 954, peripheral computing device 154 sends a connection request to local server computing device 105. The connection request may be sent to a particular available compute unit and/or may include an identifier of the available compute unit. The connection request may additionally or alternatively include an identifier of the peripheral computing device and the received scanner ID of the intraoral scanner 150. At block 956, the local server computing device may send a connection response to peripheral computing device, indicating that a connection has been established. At block 960, local server computing device 105 may send a connection request to intraoral scanner 150 using the received scanner ID associated with the intraoral scanner 150. The intraoral scanner 150 may send a connection response at block 962, after which the local server computing device may be connected to the intraoral scanner. At this point, a particular compute unit of local server computing device 105 may be connected to peripheral computing device 154 and intraoral scanner 150, and each of the compute unit of the local server computing device, the intraoral scanner 150 and the peripheral computing device 154 may be associated with one another in an intraoral scan application.

In some embodiments, display device 156 displays a display identifier of display device 156 at block 965. The display ID may be a unique identifier usable to identify display device, and may be a permanent ID (e.g., a serial number) or a temporary ID previously assigned by local server computing device 105. At block 970, intraoral scanner 150 may receive the display ID.

In one embodiment, a user may manually input the display ID into the intraoral scanner 150 using a touchscreen of the intraoral scanner. The touchscreen may display a touch keypad that includes multiple virtual buttons, where each of the virtual buttons may display a number or other character. In some embodiments, the display ID includes a limited number of possible characters (e.g., each digit of the display ID may be a value from 1-6). The size of the touchpad on the intraoral scanner 150 may be relatively small, and so the number of virtual buttons included in the displayed touch keypad may be limited (e.g., there may be 6, 5, 4 or fewer virtual buttons in the touch keypad). The touch keypad may include a different button for each character that may be included in a display ID (e.g., a different virtual button for each of number 1-6). Accordingly, a user may use the touch keypad on the touchscreen of the intraoral scanner 150 to input the display ID. In some embodiments, only a portion of the display ID is received via the touchscreen of the intraoral scanner. For example, a dentist office may have 10-50 display devices, each with a unique identifier. The lower two digits or three digits or four digits of the identifiers for the display devices may be sufficient to distinguish between the display devices. Accordingly, in some embodiments not all digits of the display ID are used.

In one embodiment, the probe head (e.g., scanning face) of the intraoral scanner 150 is pointed at the display and used to capture an image of the display ID (e.g., alphanumeric code, one-dimensional barcode, two-dimensional barcode, etc.) displayed on the display device 156. Intraoral scanner 150 may report the display ID to local server computing device 105 at block 972. Local server computing device 105 may then send a connection request to display device using the received display ID at block 974. At block 976, the display device 156 may send a connection response to local server computing device 105, causing a connection to be established between the local server computing device (e.g., the compute unit of the local server computing device) and the display device 156. The display device 156 may then be associated with the compute unit of the local server computing device 105, the intraoral scanner 150, and the peripheral computing device 154.

Note that reference above to connections established between local server computing device 105 and a display device 156 include direct connections between the local server computing device and the display device as well as connections between the local server computing device 105 and an intraoral scanning system display adapter or digital media player plugged into a data input of display device 156. For example, an intraoral scanning system display adapter may be connected to a television via an RCA cable, an high definition multimedia interface (HDMI) cable, an optical cable, a universal serial bus (USB) cable, or other audio/video or data cable. In one embodiment, the intraoral scanning system display adapter is a USB dongle that plugs into a USB port of a television. If the connection to the display device 156 is actually a connection to an intraoral scanning system display adapter or a digital media player plugged into a display device, then the display ID that is displayed on the display device and used to connect to the display device may actually be an ID of the intraoral scanning system display adapter or the digital media player.

In some embodiments, an intraoral scanning system display adapter as previously discussed herein includes a wireless module that periodically or continuously broadcasts a signal that includes a unique identifier of the display device or of the intraoral scanning system display adapter. Additionally, or alternatively, a display device may include such a wireless module. Each intraoral scanning system display adapter or display device may send or broadcast a different unique identifier than other intraoral scanning system display adapters or display devices. Scanner 150 may receive signals broadcast or sent by one or more intraoral scanning system display adapter or display device depending on a location of scanner 150. In one embodiment, the signal broadcast by each intraoral scanning system display adapter or display device may be a low power signal that is detected by scanner 150 if the scanner is within a threshold distance from an intraoral scanning system display adapter. Accordingly, the scanner 150 may detect a signal from a intraoral scanning system display adapter or display device, and report the unique identifier included in the signal to computing device 105. In one embodiment, the low power signal output by the intraoral scanning system display adapter is a signal corresponding to a low energy unidirectional wireless protocol (e.g., the iBeacon® protocol or other Bluetooth® low energy (BLE) protocol) to transmit information usable to identify the intraoral scanning system display adapter.

In one embodiment, the signal broadcast by each intraoral scanning system display adapter or display device is a Bluetooth signal, a Zigbee signal, a Wi-Fi signal, or a signal broadcast according to another wireless protocol. The intraoral scanning system display adapter or display device may broadcast signals that are powerful enough such that scanner 150 may receive signals from display adapters. Scanner 150 may report the received signals as well as signal strengths, time of flight, delay, angle of signals, etc. of the received signals to computing device 105. Computing device 105 may then use the received information to determine which of multiple intraoral scanning system display adapters should be associated with scanner 150. In one embodiment, scanner 150 is determined to be proximate to an intraoral scanning system display adapter or display device associated with a strongest signal strength.

In one embodiment, scanner 150 includes a radio frequency identification (RFID) or near field communication (NFC) reader, and periodically broadcasts a signal to read RFID or NFC chips. Each intraoral scanning system display adapter or display device may include a unique RFID or NFC identifier, and upon receiving an RFID or NFC reading signal, may respond by emitting a unique identifier. Scanner 150 may then report the unique identifier to computing device 105, which may determine an intraoral scanning system display adapter to associate with the scanner based on the unique ID as discussed above. Alternatively, each intraoral scanning system display adapter or display device may include an RFID or NFC reader, which may read an RFID or NFC chip on scanner 150, and may include a Wi-Fi module to wirelessly connect to computing device 105 and report on a received signal from a scanner 150.

Methods 900 and/or 950 may be performed in parallel or sequentially by multiple different peripheral computing devices that may all be part of the same intraoral scanning system. For example, a first peripheral computing device and a second peripheral computing device may be two of a plurality of peripheral computing devices of the intraoral scanning system. Similarly, a first intraoral scanner and a second intraoral scanner may be two of a plurality of intraoral scanners of the intraoral scanning system. Similarly, a first display device and a second display device may be two of a plurality of display devices of the intraoral scanning system. A first peripheral computing device may connect to a first intraoral scanner and/or a first display device via a first compute unit of local server computing device, and a second peripheral computing device may concurrently connect to a second intraoral scanner and/or a second display device via a second compute unit of the local server computing devices.

In some embodiments, a user may wish to connect a peripheral computing device to local server computing device without also connecting to an intraoral scanner. In such an embodiment, a user may input a connection request via the peripheral computing device, and the peripheral computing device may search for an available compute unit. The peripheral computing device may identify and connect to an available compute unit of local server computing device. While no intraoral scanner is connected to the compute unit to which the peripheral computing device is connected, intraoral scanning may not be performed in association with that peripheral computing device. However, the peripheral computing device may be used to start a patient prescription, to view a 3D model of a patient's dental arch, to review a patient prescription, and so on. At any point while the peripheral computing device is connected to the peripheral computing device, a user may input a scanner ID of an intraoral scanner to cause the local server computing device to connect to a scanner having that scanner ID and begin intraoral scanning.

At any point after an intraoral scanner and a peripheral computing device (and optionally a display device) are connected to local server computing device (e.g., to a particular compute unit of local server computing device) and associated with one another, a user may wish to disconnect one or more of the devices from the local server computing device. For example, a dental office may include more dental chairs and display devices than intraoral scanners. A dentist may carry an intraoral scanner between dental chairs, and may wish to disconnect a first display device located at a first dental chair and connect the intraoral scanner with a second display device located at a second dental chair.

In one embodiment, the peripheral computing device receives a request to disconnect the intraoral scanner, the display device and/or the peripheral computing device from the local server computing device. The peripheral computing device may then send, to the local server computing device, a disconnect instruction identifying one or more devices to be disconnected from the local server computing device. The local server computing device may then close connections to the identified devices. For example, to disconnect from a display device, a peripheral computing device may send a disconnect from display device message to the local server computing device. The local server computing device may then stop streaming a video to the display device, and may cause the display device to switch back to a listening mode in which a display ID of the display device may be displayed.

In one embodiment, to completely close an intraoral scanning session a peripheral computing device may send a close session command to the local server computing device. The local server computing device may then close a connection to the intraoral scanner, and may stop streaming of data to a display device and cause the display device to switch back to a listening mode. The local server computing device may then send a disconnect confirmation to the peripheral computing device, which the peripheral computing device may receive and display. Additionally, disconnect confirmations may be sent to the display device and/or intraoral scanner and display on those devices. Once a user of the peripheral computing device accepts the disconnect confirmation via the peripheral computing device, the peripheral computing device may send a disconnect confirmation message to the local server computing device, causing the connection between the peripheral computing device and the local server computing device to terminate.

In one embodiment, a message is sent to one or more of the devices asking for confirmation to close a connection. For example, a disconnect confirmation message may be sent to the intraoral scanner and/or to the peripheral computing device, and may be displayed on one or more of those devices along with a proceed virtual button or icon and a cancel virtual button or icon. A user may select or press the proceed virtual button or icon to proceed with disconnecting the device(s) from local server computing device, or may select the cancel virtual button or icon to cancel the disconnection process.

Figure 10A:
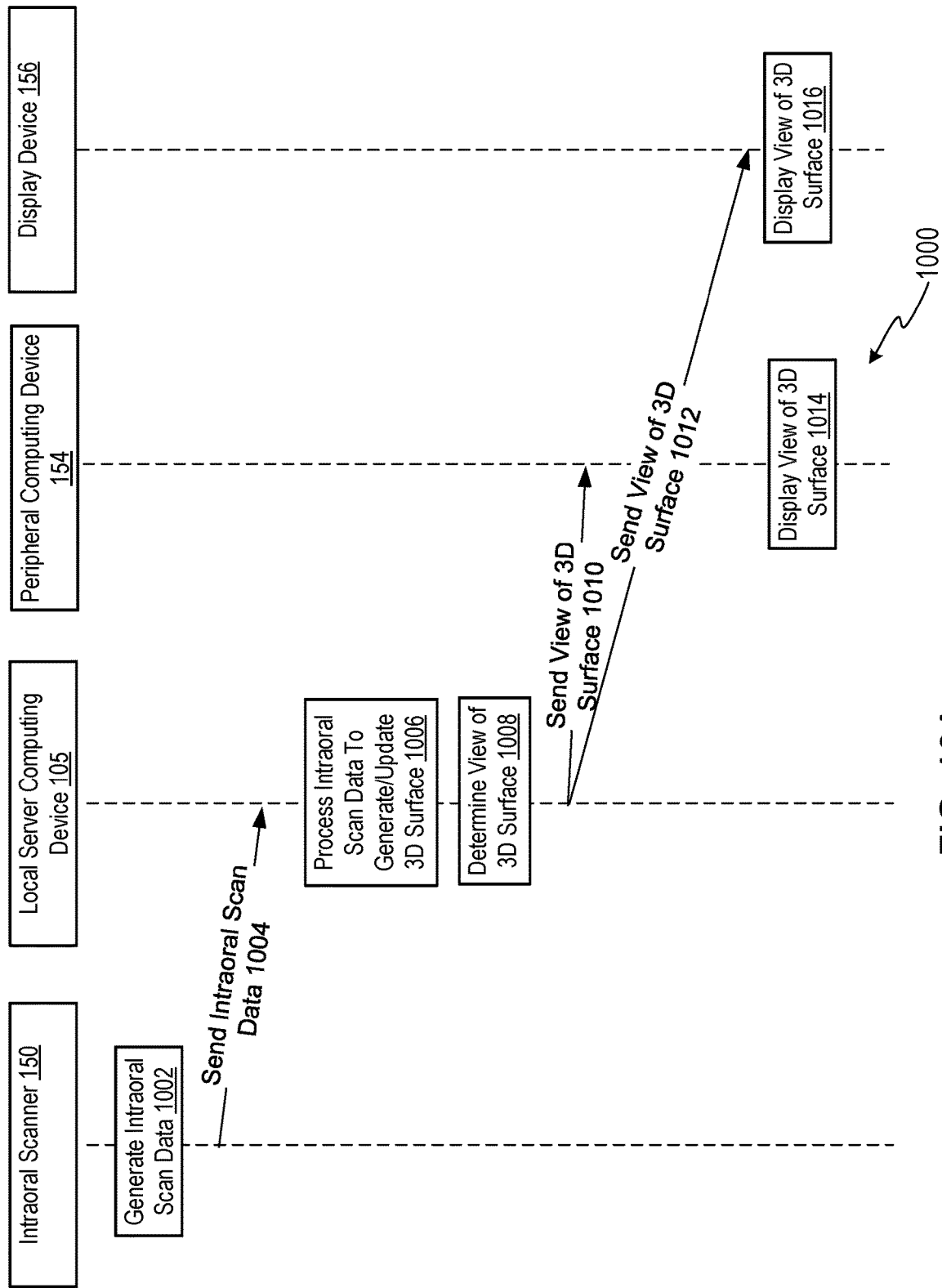
FIG. 10A is a sequence diagram illustrating an intraoral scanning process involving multiple wirelessly connected devices, in accordance with embodiments of the present disclosure.

FIG. 10A is a sequence diagram illustrating an intraoral scanning process 1000 involving multiple wirelessly connected devices, in accordance with embodiments of the present disclosure. At block 1002 of process 1000, intraoral scanner 150 generates intraoral scan data, which may include intraoral scans, 2D color images (e.g., viewfinder images), 2D NIRI images, and so on. At block 1004, the intraoral scanner 150 wirelessly transmits the intraoral scan data to local server computing device 105. At block 1006, local server computing device 105 processes the intraoral scan data to generate or update a 3D surface of a dental site being scanned. At block 1008, the local server computing device 105 may determine a view of the 3D surface. At block 1010, local server computing device 105 may wirelessly transmit the view of the 3D surface to peripheral computing device 154. At block 1012, local server computing device 105 may additionally wirelessly transmit the view of the 3D surface to display device 156. A current viewfinder image may also be sent at block 1010 and 1012. At block 1014, peripheral computing device 154 displays the view of the 3D surface (and optionally the current viewfinder image). At block 1016, display device 156 displays the view of the 3D surface (and optionally the current viewfinder image). This process may repeat until intraoral scanning stops or until an intraoral scan application transitions from a scanning mode to another mode of operation. The intraoral scanner may generate multiple intraoral scans and/or images per second, and with each intraoral scan a 3D surface may be updated, and an updated view of the 3D surface may be streamed to a peripheral computing device and/or display device.

Figure 10B:
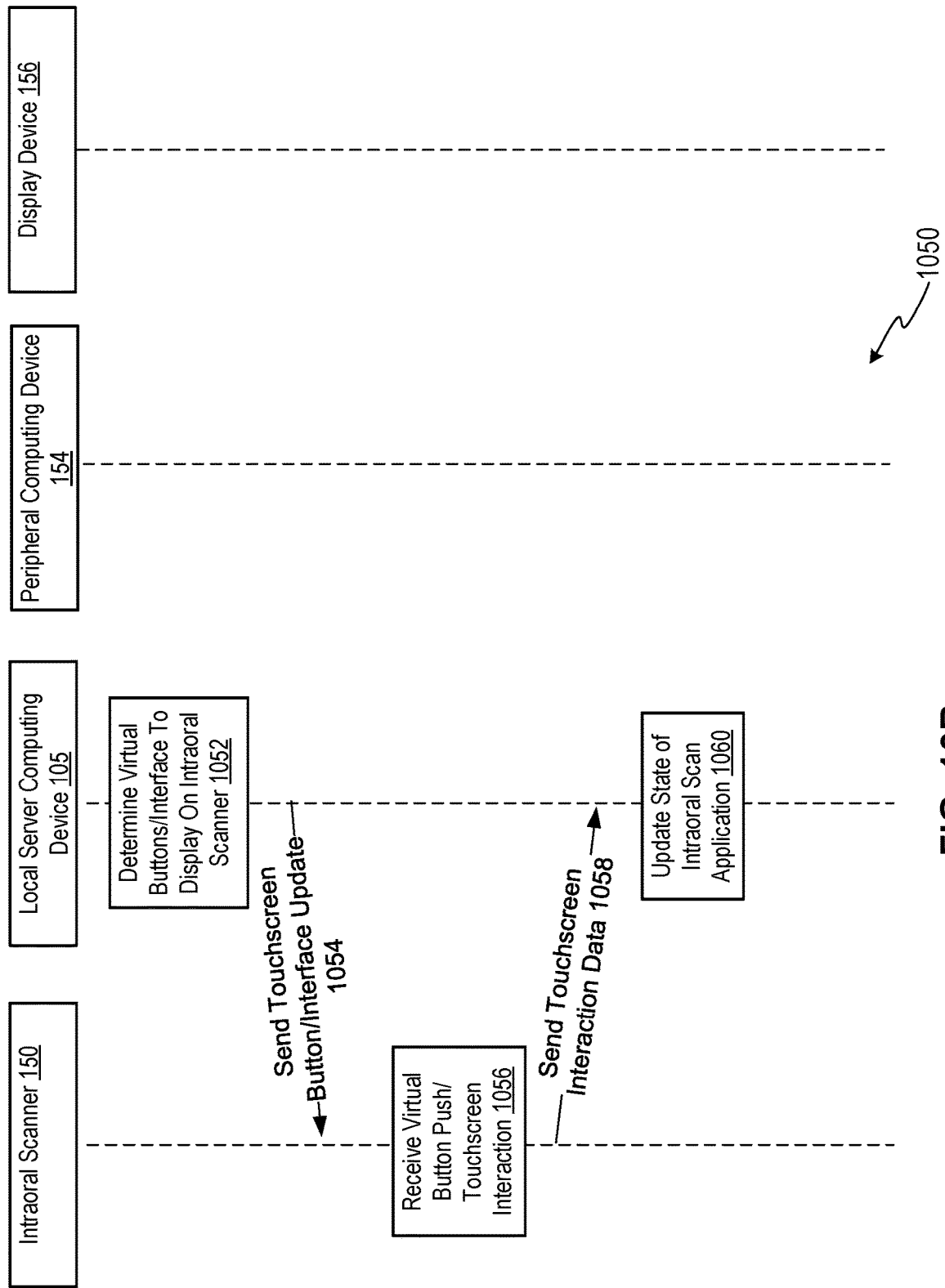
FIG. 10B is a sequence diagram illustrating use of an intraoral scanner touchscreen to control an intraoral scan application, in accordance with embodiments of the present disclosure.

FIG. 10B is a sequence diagram illustrating a method 1050 of using of an intraoral scanner touchscreen to control an intraoral scan application, in accordance with embodiments of the present disclosure. At block 1052, local server computing device 105 determines one or more virtual buttons, an interface and/or other data to display on a touchscreen of intraoral scanner 150. The determination of what virtual buttons to display may be based at least in part on a current mode of operation of an intraoral scan application executing on local server computing device 105. For example, first buttons may be displayed on the touchscreen during a scanning mode, and second buttons may be displayed on the touchscreen during a review mode. At block 1054, the local server computing device 105 sends a touchscreen/button/interface update to the intraoral scanner, where the update indicates what data to display on the touchscreen. In some embodiments, local server computing device 105 sends over actual images and/or videos to be displayed or streamed to the touchscreen. In some embodiments, intraoral scanner 150 includes a memory with multiple different touchscreen virtual buttons and/or interfaces stored therein. In such an embodiment, local server computing device 105 may send over a code indicating what virtual buttons or what interface is to be displayed, and intraoral scanner 150 may access the stored data to determine, based on the code, what images, virtual buttons and/or icons to display on the touchscreen.

At block 1056, intraoral scanner 150 receives a virtual button push and/or other touchscreen interaction. At block 1058, intraoral scanner 150 may wirelessly transmit the touchscreen interaction data (e.g., indication of what virtual button or virtual buttons were pushed, indication of what touch motion or gesture was detected, etc.) to local server computing device 105. At block 1060, local server computing device 105 may update a state of the intraoral scan application based on the receive touchscreen interaction data. For example, a mode of the intraoral scan application may be changed, a view of a 3D surface may be changed, an active scanning segment may be changed, and so on.

A few examples of touchscreen interfaces with virtual buttons are described below. FIGS. 11A-F illustrate example virtual buttons on an intraoral scanner touchscreen, in accordance with embodiments of the present disclosure.

Figures 11A, 11B:
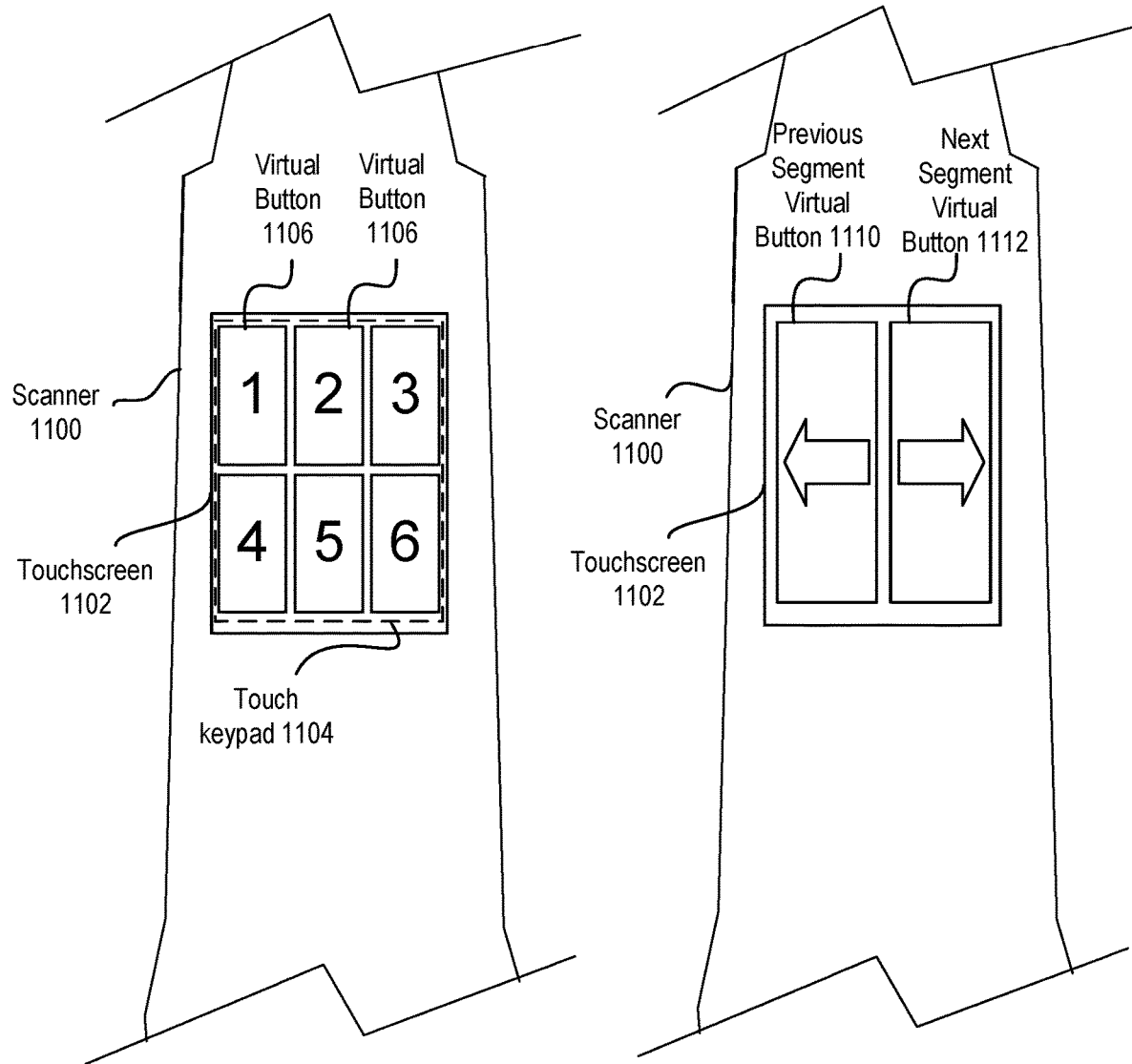
FIGS. 11A-F illustrate example virtual buttons on an intraoral scanner touchscreen, in accordance with embodiments of the present disclosure.

FIG. 11A illustrates an intraoral scanner 1100 having a touchscreen 1102 displaying a touch keypad 1104 including a plurality of virtual buttons 1106. As shown, each virtual button 1106 includes a different character (e.g., a different number). A user may use the touch keypad 1104 to enter a code, such as a display ID of a display device to associated with the intraoral scanner 1100. The touch keypad 1104 may be displayed on touchscreen 1102 responsive to a user inputting a command via the intraoral scanner or via a peripheral computing device to connect to a display device. After the user types the display ID (or a portion of the display ID sufficient to uniquely distinguish a target display device from other nearby display devices), the local server computing device may output a message to the display device indicating that it is being associated with the intraoral scanner. Additionally, the local server computing device may output a message to intraoral scanner asking if the desired display device has been connected, and touchscreen 1102 may display the message. Additionally, touchscreen 1102 may display an accept virtual button 1130 and a cancel virtual button 1132, as shown in FIG. 11E, or an option I virtual button 1134 and an option II virtual button 1136, as shown in FIG. 11F. A user may press the accept virtual button 1116 to confirm that a connection has been established with the correct display device, or may press the cancel virtual button 1118 to indicate that a connection has not been established with the correct display device.

FIG. 11B illustrates an intraoral scanner 1100 having a touchscreen 1102 displaying an interface for navigating between scanning segments during intraoral scanning. The scanning segments may include, for example, an upper dental arch segment, a lower dental arch segment, and a patient bite segment. A user may presently be scanning one of the segments (e.g., upper dental arch segment), and upon completion of that segment may desire to scan a next segment (e.g., a lower dental arch segment). Accordingly, the user may press a next segment virtual button 1112 to transition to scanning of a next segment (e.g., lower dental arch segment). Once that segment is complete, the user may again press the next segment button to transition to scanning of a next segment (e.g., patient bite segment). At any time, a user may press a previous segment virtual button to revisit scanning of an already scanned segment. For example, if a user is presently scanning a bite segment, the user may press the previous segment virtual button to transition to scanning of the lower dental arch segment, and may again press the previous segment virtual button to transition to scanning of the upper dental arch segment.

Figures 11C, 11D:
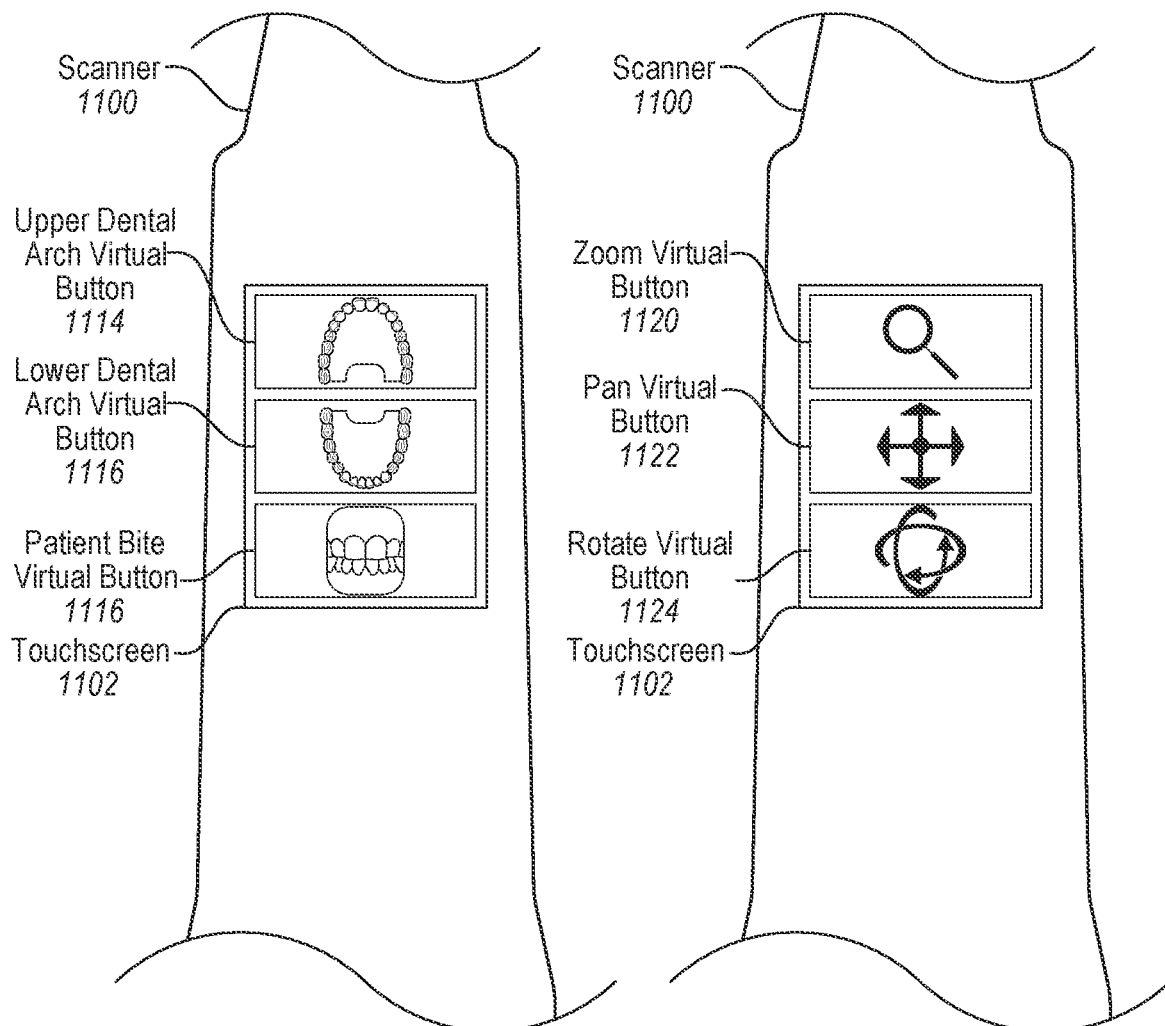
Figures 11E, 11F:
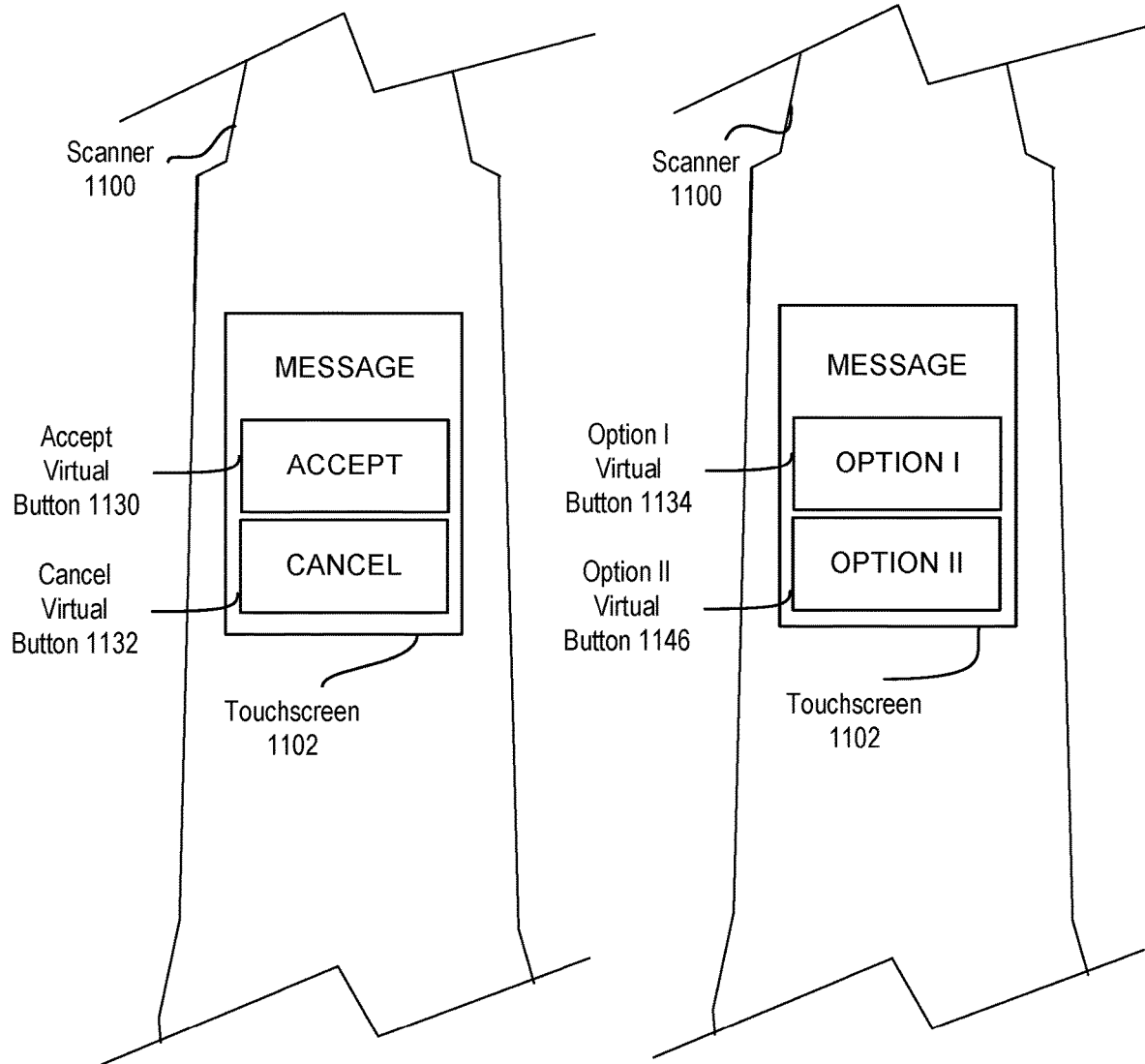

FIG. 11C illustrates an intraoral scanner 1100 having a touchscreen 1102 displaying an alternate interface for navigating between scanning segments during intraoral scanning. The scanning segments may include, for example, an upper dental arch segment, a lower dental arch segment, and a patient bite segment. In one embodiment, the interface of the touchscreen 1102 includes an upper dental arch segment virtual button 1114, a lower dental arch segment virtual button 1116, and a patient bite virtual button 1118. A user may presently be scanning one of the segments (e.g., upper dental arch segment), and upon completion of that segment may desire to scan another segment (e.g., a lower dental arch segment). Accordingly, the user may press a virtual button associated with a segment that the user wishes to scan. Once that segment is complete, the user may press a different segment virtual button to transition to scanning of a next segment (e.g., patient bite segment). At any time, a user may press any of the scan segment virtual buttons to enable further scanning of that segment.

In one embodiment, a user may select a desired interface to use for touchscreen 1102 during scanning for workflow control (e.g., navigating between segments). For example, a user may select to use the interface shown in FIG. 11B for transitioning between scan segments, or may select to use the interface shown in FIG. 11C for transitioning between scan segments.

FIG. 11D illustrates an intraoral scanner 1100 having a touchscreen 1102 displaying an interface for controlling a view of a 3D surface or 3D model of a dental site, referred to a model view manipulation. At any time during scanning, a user may wish to assess a scan progress by viewing a 3D surface from one or more virtual camera positions and/or angles and/or magnification settings. The user may provide an input via scanner 1100 (e.g., via touchscreen 1102 and/or one or more buttons of scanner 1100) to momentarily transition out of a scanning mode and into a viewing mode. While in the viewing mode, touchscreen 1102 may display a zoom virtual button 1120, a pan virtual button 1122, and a rotate virtual button 1124. In one embodiment, a user may press one of the pan virtual button 1122, the zoom virtual button 1120 or the rotate virtual button 1124 to select an appropriate manipulation mode (e.g., a pan mode, zoom mode or rotate mode). In the appropriate mode, further interaction with the touchscreen may cause a particular type of manipulation associated with a current manipulation mode. For example, in the pan mode, dragging a finger across the touchscreen may cause a 3D surface to pan. In the rotate mode, dragging a finger across the touchscreen may cause a 3D surface to rotate. In a zoom mode, dragging a finger across the touchscreen may cause a 3D surface to zoom in or out.

In one embodiment, the user may press on the pan virtual button to pan a view of the 3D surface. In one embodiment, the pan virtual button includes four arrows, and a direction and/or amount of panning depends on where in the pan virtual button a user presses. For example, pressing on a right facing arrow of the pan virtual button may cause panning to the right, pressing on an upward facing arrow may cause upward panning, and so on. In one embodiment, different swipe gestures within the rotate virtual button cause a particular rotation of the view of the 3D surface (e.g., of a virtual camera viewing the 3D surface). For example, a rightward swipe may cause a rotation about a vertical axis in the right direction. In one embodiment, a rightward swipe in the zoom virtual button causes a zoom in command, and a leftward swipe in the zoom virtual button causes a zoom out command. Alternatively, pressing on any of the virtual buttons shown in FIG. 11D causes one or more new virtual buttons associated with the selected viewing operation to be displayed.

In one embodiment, different gestures on the touchscreen cause different operations changing a view of a 3D surface or 3D model. For example, the touchscreen may support multi-touch control. Dragging of a first number of fingers (e.g., one finger) of a user across the touchscreen may cause rotation of a three-dimensional surface on a display. Dragging of a second number of fingers (e.g., two fingers) of the user across the touchscreen may cause panning of the three-dimensional surface on the display. An inward pinching motion of a user's fingers on the touchscreen may cause zooming out of the three-dimensional surface on the display. An outward pinching motion of the user's fingers on the touchscreen may cause zooming in of the three-dimensional surface on the display.

FIG. 11E shows a touchscreen 1102 displaying a message along with an accept virtual button 1130 and a cancel virtual button 1132. The message may be an inquiry asking a user if something is correct or if an operation should be performed, for example. Many other types of messages are also possible. The user may press an accept virtual button 1130 to confirm the action or request, or may press a cancel virtual button 1132 to refuse or cancel the action or request.

FIG. 11F shows a touchscreen 1102 displaying a message along with an option I virtual button 1134 and an option II virtual button 1136. The message may be an inquiry asking a user which of multiple options a user wishes to proceed with. The specific options displayed may be case dependent. The user may press an option I virtual button 1134 to proceed with a first option, or may press an option II virtual button 1146 to proceed with a second option. One or more additional virtual buttons may also present one or more other options.

In some embodiments, once intraoral scanning is complete, touchscreen 1102 displays an icon or message indicating that intraoral scanning is complete. The touchscreen may additionally or alternatively include a virtual button that, when pressed, causes an intraoral scanning application to transition out of a scanning mode and into a subsequent mode (e.g., a review mode).

The touchscreen may provide one or more virtual buttons for feature activation of one or more features of an intraoral scan application. In one embodiment, a long press of the touchscreen (e.g., of a particular icon or virtual button on the touchscreen) will cause a menu to pop-up in the touchscreen and/or on a display of a peripheral computing device. The pop-up menu may provide a menu of multiple different feature options and/or icons/virtual buttons for control of one or more features, for example as shown in FIG. 11F. Some examples of features that may be controlled are visualization features. For example, virtual buttons or menu options may be presented for turning on or off color on a 3D surface or virtual 3D model, for turning on or off occlusal clearance information (e.g., optionally displayed as a heat map overlay on a 3D model of a dental arch), for turning on or off a fast hole detection (FHD) algorithm (a real-time hole detection algorithm that identifies and highlights holes greater than a threshold size), and so on.

Figure 12:
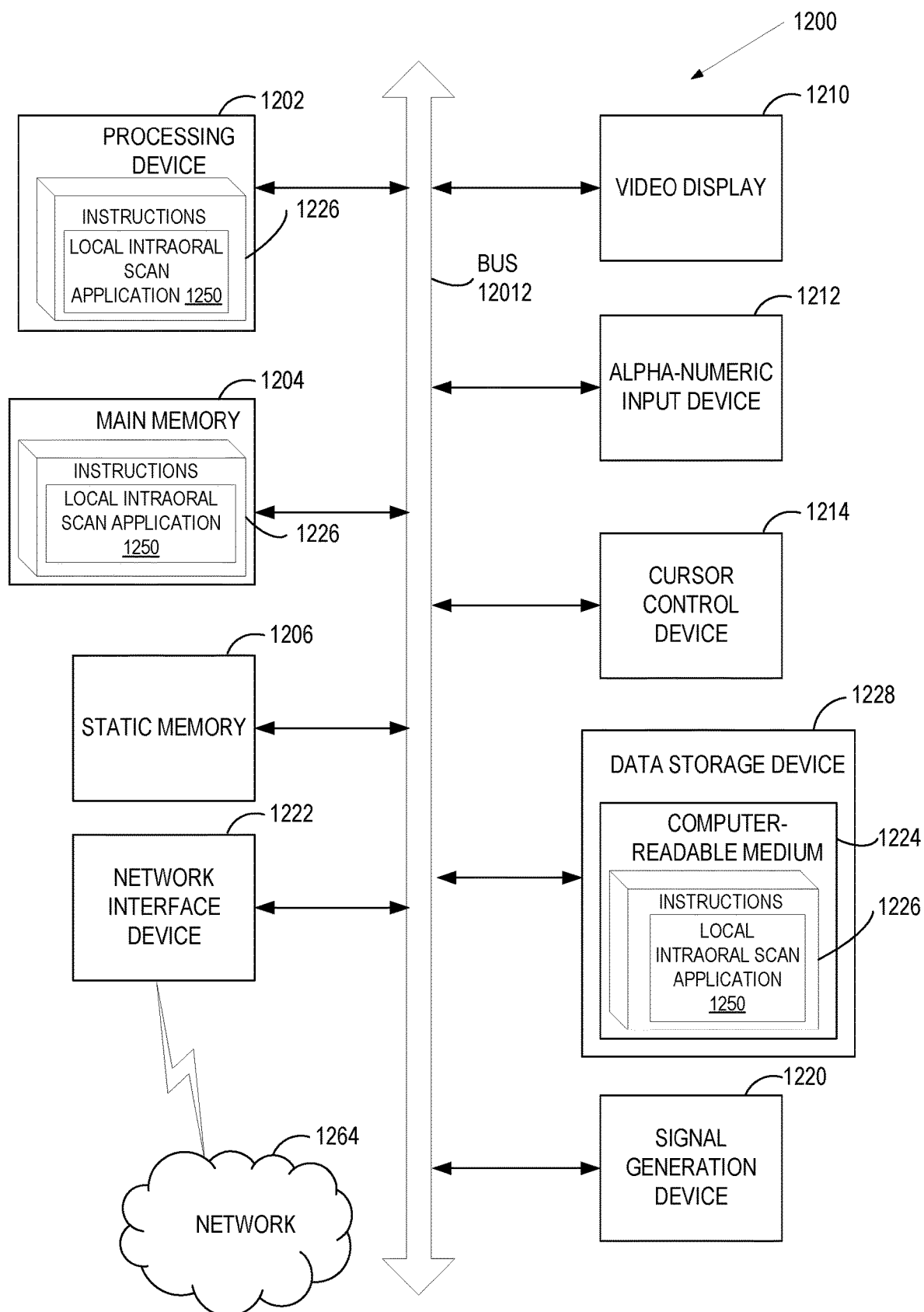
FIG. 12 illustrates a block diagram of an example computing device, in accordance with embodiments of the present disclosure.

FIG. 12 illustrates a diagrammatic representation of a machine in the example form of a computing device 1200 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The computing device 1200 may correspond, for example, to computing device 105 and/or computing device 106 of FIG. 1. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 1200 includes a processing device 1202, a main memory 1204 (e.g., read-only memory (ROM), flash memory, dynamic random access memory (DRAM) such as synchronous DRAM (SDRAM), etc.), a static memory 1206 (e.g., flash memory, static random access memory (SRAM), etc.), and a secondary memory (e.g., a data storage device 1228), which communicate with each other via a bus 1208.

Processing device 1202 represents one or more general-purpose processors such as a microprocessor, central processing unit, or the like. More particularly, the processing device 1202 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. Processing device 1202 is configured to execute the processing logic (instructions 1226) for performing operations and steps discussed herein.

The computing device 1200 may further include a network interface device 1222 for communicating with a network 1264. The computing device 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse), and a signal generation device 1220 (e.g., a speaker).

The data storage device 1228 may include a machine-readable storage medium (or more specifically a non-transitory computer-readable storage medium) 1224 on which is stored one or more sets of instructions 1226 embodying any one or more of the methodologies or functions described herein, such as instructions for dental modeling logic 1250. A non-transitory storage medium refers to a storage medium other than a carrier wave. The instructions 1226 may also reside, completely or at least partially, within the main memory 1204 and/or within the processing device 1202 during execution thereof by the computer device 1200, the main memory 1204 and the processing device 1202 also constituting computer-readable storage media.

The computer-readable storage medium 1224 may also be used to store local intraoral scan application 1250 or remote intraoral scan application (not shown), which may perform the operations described herein above. The computer readable storage medium 1224 may also store a software library containing methods for the dental modeling logic 1250. While the computer-readable storage medium 1224 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

Figure 13:
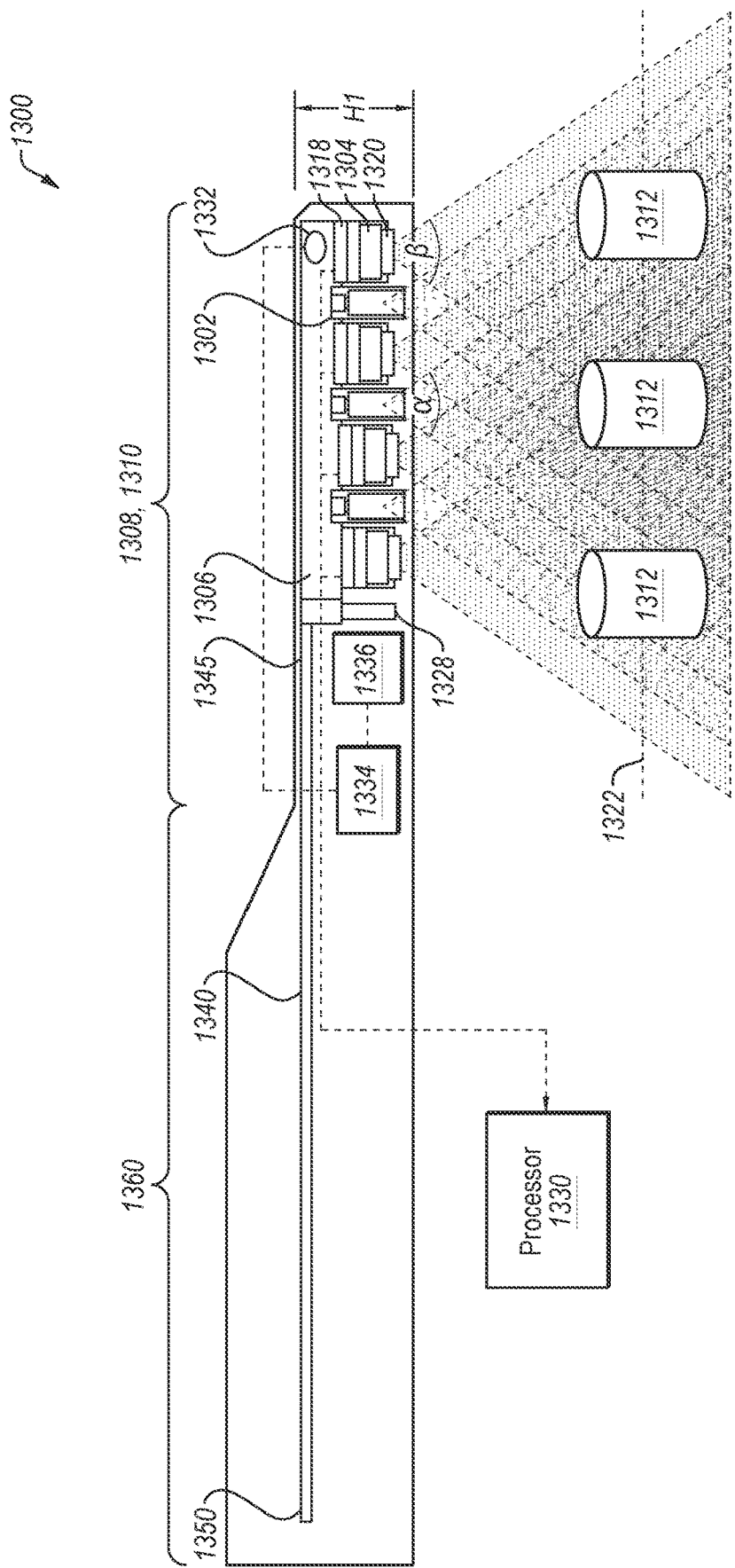
FIG. 13 illustrates an example intraoral scanner, in accordance with embodiments of the present disclosure.

Reference is now made to FIG. 13, which is a schematic illustration of an intraoral scanner 1300 comprising an elongate handheld wand (e.g., a body with a probe at one end of the body), in accordance with some applications of the present disclosure. The intraoral scanner 1300 may include a wireless module (not shown) disposed in a body of the intraoral scanner 1300. The intraoral scanner 1300 may correspond to intraoral scanner 150 of FIGS. 1A-B in embodiments. Intraoral scanner 1300 includes a plurality of structured light projectors 1302 and a plurality of cameras 1304 that are coupled to a rigid structure 1306 disposed within a probe 1308 at a distal end 1310 of the body of the intraoral scanner 1300. In some applications, during an intraoral scanning procedure, probe 1308 is inserted into the oral cavity of a subject or patient.

For some applications, structured light projectors 1302 are positioned within probe 1308 such that each structured light projector 1302 faces an object 1312 outside of intraoral scanner 1300 that is placed in its field of illumination, as opposed to positioning the structured light projectors in a proximal end of the handheld wand and illuminating the object by reflection of light off a mirror and subsequently onto the object. Alternatively, the structured light projectors may be disposed at a proximal end of the handheld wand. Similarly, for some applications, cameras 1304 and/or other optical sensors are positioned within probe 1308 such that each camera 1304 faces an object 1312 outside of intraoral scanner 1300 that is placed in its field of view, as opposed to positioning the cameras in a proximal end of the intraoral scanner and viewing the object by reflection of light off a mirror and into the camera. This positioning of the projectors and the cameras within probe 1308 enables the scanner to have an overall large field of view while maintaining a low profile probe. Alternatively, the cameras may be disposed in a proximal end of the handheld wand.

In some applications, cameras 1304 each have a large field of view β (beta) of at least 45 degrees, e.g., at least 70 degrees, e.g., at least 80 degrees, e.g., 85 degrees. In some applications, the field of view may be less than 120 degrees, e.g., less than 100 degrees, e.g., less than 90 degrees. In one embodiment, a field of view β (beta) for each camera is between 80 and 90 degrees, which may be particularly useful because it provided a good balance among pixel size, field of view and camera overlap, optical quality, and cost. Cameras 1304 may include an image sensor 1318 and objective optics 1320 including one or more lenses. To enable close focus imaging, cameras 1304 may focus at an object focal plane 1322 that is located between 1 mm and 30 mm, e.g., between 4 mm and 24 mm, e.g., between 5 mm and 11 mm, e.g., 9 mm-10 mm, from the lens that is farthest from the sensor. In some applications, cameras 1304 may capture images at a frame rate of at least 30 frames per second, e.g., at a frame of at least 75 frames per second, e.g., at least 100 frames per second. In some applications, the frame rate may be less than 200 frames per second.

A large field of view achieved by combining the respective fields of view of all the cameras may improve accuracy due to reduced amount of image stitching errors, especially in edentulous regions, where the gum surface is smooth and there may be fewer clear high resolution 3D features. Having a larger field of view enables large smooth features, such as the overall curve of the tooth, to appear in each image frame, which improves the accuracy of stitching respective surfaces obtained from multiple such image frames.

Similarly, structured light projectors 1302 may each have a large field of illumination α (alpha) of at least 45 degrees, e.g., at least 70 degrees. In some applications, field of illumination α (alpha) may be less than 120 degrees, e.g., than 100 degrees.

For some applications, in order to improve image capture, each camera 1304 has a plurality of discrete preset focus positions, in each focus position the camera focusing at a respective object focal plane 1322. Each of cameras 1304 may include an autofocus actuator that selects a focus position from the discrete preset focus positions in order to improve a given image capture. Additionally or alternatively, each camera 1304 includes an optical aperture phase mask that extends a depth of focus of the camera, such that images formed by each camera are maintained focused over all object distances located between 1 mm and 30 mm, e.g., between 4 mm and 24 mm, e.g., between 5 mm and 11 mm, e.g., 9 mm-10 mm, from the lens that is farthest from the sensor.

In some applications, structured light projectors 1302 and cameras 1304 are coupled to rigid structure 1306 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected pattern of light are in the field of view of at least one of the cameras at an object focal plane 1322 that is located at least 4 mm from the lens that is farthest from the sensor. Due to different possible configurations of the projectors and cameras, some of the projected pattern may never be seen in the field of view of any of the cameras, and some of the projected pattern may be blocked from view by object 1312 as the scanner is moved around during a scan.

Rigid structure 1306 may be a non-flexible structure to which structured light projectors 1302 and cameras 1304 are coupled so as to provide structural stability to the optics within probe 1308. Coupling all the projectors and all the cameras to a common rigid structure helps maintain geometric integrity of the optics of each structured light projector 1302 and each camera 1304 under varying ambient conditions, e.g., under mechanical stress as may be induced by the subject's mouth. Additionally, rigid structure 1306 helps maintain stable structural integrity and positioning of structured light projectors 1302 and cameras 1304 with respect to each other.

For some applications, there is at least one uniform light projector 1328 (which may be an unstructured light projector that projects light across a range of wavelengths) coupled to rigid structure 1306. Uniform light projector 1328 may transmit white light onto object 1312 being scanned. At least one camera, e.g., one of cameras 1304, captures two-dimensional color images of object 1312 using illumination from uniform light projector 1328. Light reflecting off of the object 1312 may enter the scanner head and be received by the cameras. The cameras may then generate intraoral scan data based on the received light. The wireless communication module may wirelessly send the intraoral scan data to a local server computing device in embodiments.

A processor or processing device 1330 of the local server computing device may run a surface reconstruction algorithm that may use detected patterns (e.g., dot patterns) projected onto object 1312 to generate a 3D surface of the object 1312. In some embodiments, the processor 1330 may combine at least one 3D scan captured using illumination from structured light projectors 1302 with a plurality of intraoral 2D images captured using illumination from uniform light projector 1328 in order to generate a digital three-dimensional image of the intraoral three-dimensional surface. Using a combination of structured light and uniform illumination enhances the overall capture of the intraoral scanner and may help reduce the number of options that processor 1330 needs to consider when running a correspondence algorithm used to detect depth values for object 1312. In one embodiment, the intraoral scanner and correspondence algorithm described in U.S. application Ser. No. 16/446,181, filed Jun. 19, 2019, is used. U.S. application Ser. No. 16/446,181, filed Jun. 19, 2019, is incorporated by reference herein in its entirety. In embodiments, processor 1330 may be a processor of local server computing device 105 of FIGS. 1A-B. Alternatively, processor 1330 may be a processor integrated into the intraoral scanner 1300.

For some applications, all data points taken at a specific time are used as a rigid point cloud, and multiple such point clouds are captured at a frame rate of over 10 captures per second. The plurality of point clouds are then stitched together using a registration algorithm, e.g., iterative closest point (ICP), to create a dense point cloud. A surface reconstruction algorithm may then be used to generate a representation of the surface of object 1312.

For some applications, at least one temperature sensor 1332 is coupled to rigid structure 1306 and measures a temperature of rigid structure 1306. Temperature control circuitry 1334 disposed within handheld wand 1300 (a) receives data from temperature sensor 1332 indicative of the temperature of rigid structure 1306 and (b) activates a temperature control unit 1336 in response to the received data. Temperature control unit 1336, e.g., a PID controller, keeps probe 1308 at a target temperature (e.g., between 35 and 43 degrees Celsius, between 37 and 41 degrees Celsius, etc.). Keeping probe 1308 above 35 degrees Celsius, e.g., above 37 degrees Celsius, reduces fogging of the glass surface of handheld wand 1300, through which structured light projectors 1302 project and cameras 1304 view, as probe 1308 enters the oral cavity, which is typically around or above 37 degrees Celsius. Keeping probe 1308 below 43 degrees, e.g., below 41 degrees Celsius, prevents discomfort or pain.

In some embodiments, heat may be drawn out of the probe 1308 via a heat conducting element 1340, e.g., a heat pipe, that is disposed within handheld wand 1300, such that a distal end 1345 of heat conducting element 1340 is in contact with rigid structure 1306 and a proximal end 1350 is in contact with a proximal end 1360 of handheld wand 1300. Heat is thereby transferred from rigid structure 1306 to proximal end 1360 of handheld wand 1300. Alternatively or additionally, a fan disposed in a handle region of handheld wand 1300 may be used to draw heat out of probe 1308.

In one embodiment, intraoral scanner 150 corresponds to the intraoral scanner described in U.S. application Ser. No. 16/910,042, filed Jun. 23, 2020 and entitled "Intraoral 3D Scanner Employing Multiple Miniature Cameras and Multiple Miniature Pattern Projectors", which is incorporated by reference herein. In one embodiment, intraoral scanner 150 corresponds to the intraoral scanner described in U.S. application Ser. No. 16/446,181, filed Jun. 19, 2019 and entitled "Intraoral 3D Scanner Employing Multiple Miniature Cameras and Multiple Miniature Pattern Projectors", which is incorporated by reference herein.

In some embodiments, intraoral scanner 1300 includes a touchscreen (not shown) disposed on the body of the intraoral scanner 1300. The touchscreen may be configured to output a plurality of virtual buttons, to detect a touch input associated with a virtual button of the plurality of virtual buttons, and to provide a signal associated with the touch input of the virtual button to the processor of the local server computing device. In some embodiments, intraoral scanner 1300 may receive an input from the local server computing device indicating a current mode of an intraoral scan application. Intraoral scanner 1300 may then determine the plurality of virtual buttons to output on the touchscreen based on the current mode of the intraoral scan application and/or based on past inputs. Alternatively, the local server computing device may determine what virtual buttons are to be displayed on the touchscreen, and may provide data on what is to be displayed on the touchscreen to intraoral scanner 1300.

In some embodiments an intraoral scanner that performs confocal focusing to determine depth information may be used.

Figure 14:
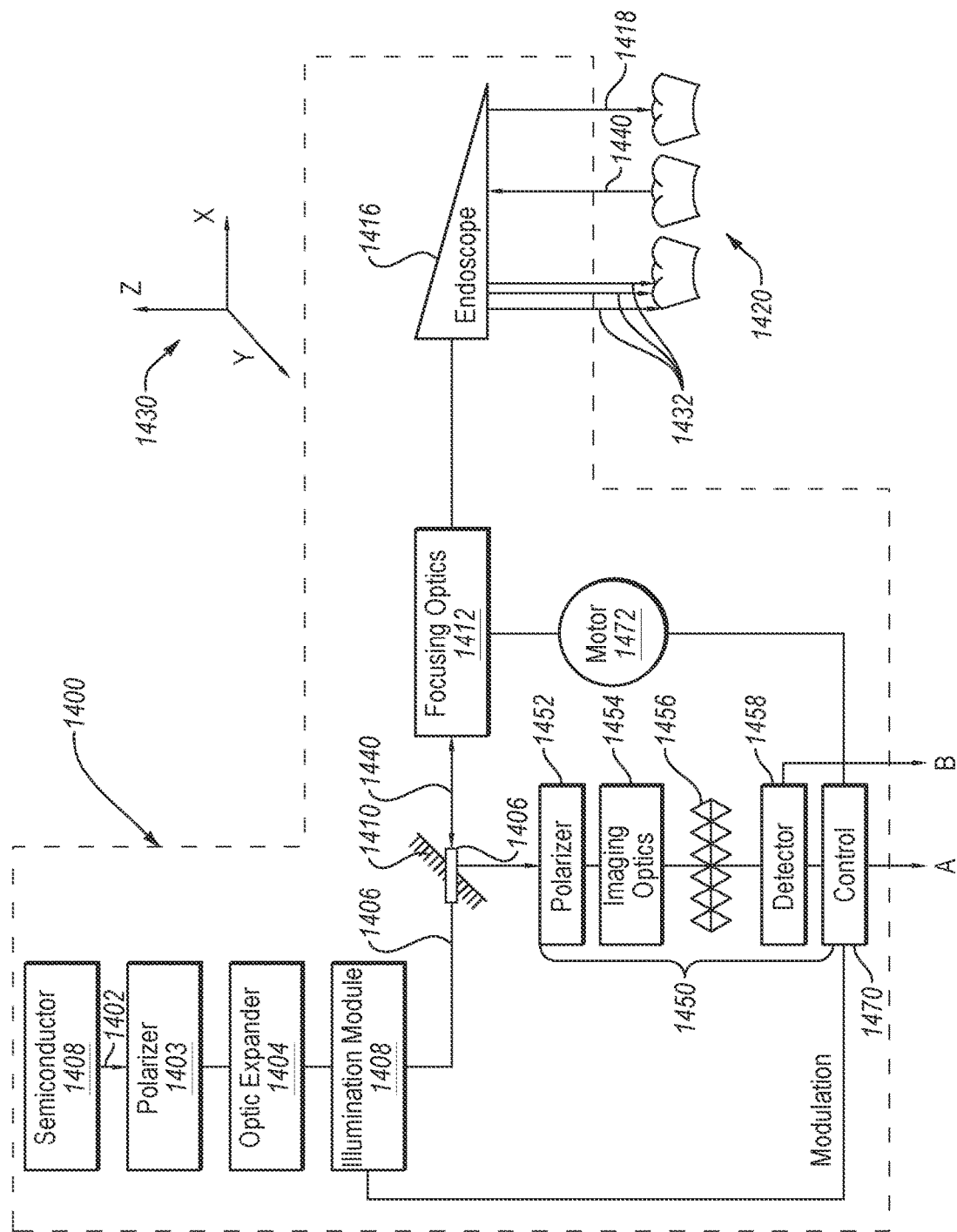
FIG. 14 illustrates another example intraoral scanner, in accordance with embodiments of the present disclosure.

FIG. 14 illustrates a functional block diagram of an intraoral scanner 1400 according to one embodiment. Intraoral scanner 1400 may correspond to intraoral scanner 150 of FIGS. 1A-B in embodiments. Together, the intraoral scanner 1400 and one or more computing device (e.g., local server computing device 105 and/or one or more additional computing devices 152, 154 of FIGS. 1A-B) may form a system for generating three dimensional surfaces and/or models of scanned intraoral objects. In one embodiment, the intraoral scanner is a confocal intraoral scanner. In one embodiment, intraoral scanner 1400 includes a touchscreen and a wireless communication module, as discussed above.

In one embodiment intraoral scanner 1400 includes a body comprising a probe at one end of the body. The probe includes a scanner head. The probe may include, for example, an endoscope 1416. Intraoral scanner 1400 includes a semiconductor laser unit 1408 in the body that emits focused light (e.g., a focused light beam), as represented by arrow 1402. The light 1402 passes through a polarizer 1403. Polarizer 1403 polarizes the light beam passing through polarizer 1403. Alternatively, polarizer 1403 may be omitted in some embodiments. The light then enters into an optic expander 1404 in the body that improves a numerical aperture of the light 1402. The light 1402 then passes through an illumination module 1408 in the body, which may split the light 1402 into an array of incident light beams 1406, represented here, for ease of illustration, by a single line. The illumination module 1408 may be, for example, a grating or a micro lens array that splits the light 1402 into an array of light beams 1406. In one embodiment, the array of light beams 1406 is an array of telecentric light beams. Alternatively, the array of light beams may not be telecentric.

The intraoral scanner 1400 further includes a unidirectional mirror or beam splitter (e.g., a polarizing beam splitter) 1410 in the body that passes the array of light beams 1406. A unidirectional mirror 1410 allows transfer of light from the semiconductor laser 1408 through to downstream optics, but reflects light travelling in the opposite direction. A polarizing beam splitter allows transfer of light (e.g., light beams) having a particular polarization and reflects light beams having a different (e.g., opposite) polarization. In one embodiment, the unidirectional mirror or beam splitter 1410 has a small central aperture. The small central aperture may improve a measurement accuracy of the intraoral scanner 1400. In one embodiment, as a result of a structure of the unidirectional mirror or beam splitter 1410, the array of light beams will yield a light annulus on an illuminated area of an imaged object as long as the area is not in focus. Moreover, the annulus will become a completely illuminated spot once in focus. This ensures that a difference between measured intensities of out-of-focus points and in-focus points will be larger.

Along an optical path of the array of light beams after the unidirectional mirror or beam splitter 1410 are focusing optics 1412 in the body, and an endoscopic probing member 46 at one end of the body. In one embodiment, the focusing optics are confocal focusing optics. Additionally, a quarter wave plate may be disposed along the optical path after the unidirectional mirror or beam splitter 1410 to introduce a certain polarization to the array of light beams. In some embodiments this may ensure that reflected light beams will not be passed through the unidirectional mirror or beam splitter 1410. Focusing optics 1412 may additionally include relay optics (not shown). Focusing optics 1412 may or may not maintain the same magnification of an image over a wide range of distances in the Z direction, wherein the Z direction is a direction of beam propagation (e.g., the Z direction corresponds to an imaging axis that is aligned with an optical path of the array of light beams 1406). The relay optics enable the intraoral scanner 1400 to maintain a certain numerical aperture for propagation of the array of light beams 1406.

The endoscopic probing member 1416 may include a rigid, light-transmitting medium, which may be a hollow object defining within it a light transmission path or an object made of a light transmitting material, e.g. a glass body or tube. In one embodiment, the endoscopic probing member 1416 include a prism such as a folding prism. At its end, the endoscopic probing member 1416 may include a mirror of the kind ensuring a total internal reflection. Thus, the mirror may direct the array of light beams towards a teeth segment 1420 or other intraoral object. The endoscope probing member 1416 thus emits light 1418 (e.g., an array of light beams), which impinges on to surfaces of the teeth section 1420.

The light 1418 (e.g., array of light beams) may be arranged in an X-Y plane, in the Cartesian frame 1430, propagating along the Z axis. As the surface on which the incident light hits is an uneven surface, illuminated points or locations 1432 are displaced from one another along the Z axis, at different $(X_i, Y_i)$ locations. Thus, while a point at one location may be in focus of the focusing optics 1412, points at other locations may be out-of-focus. Therefore, the light intensity of returned light (e.g., returned light beams) of the focused points will be at its peak, while the light intensity at other points will be off peak. Thus, for each illuminated point, multiple measurements of light intensity are made at different positions along the Z-axis. For each of such $(X_i, Y_i)$ location, the derivative of the intensity over distance (Z) may be made, with the $Z_i$ yielding maximum derivative, $Z_0$, being the in-focus distance. As pointed out above, the incident light from the light 1418 may form a light disk or a blurry image on the surface when out of focus and a complete light spot or a sharp image when in focus. Thus, the distance derivative will be larger when approaching in-focus position, increasing accuracy of the measurement.

The light scattered from each of the points may include a beam travelling initially in the Z axis along the opposite direction of the optical path traveled by the light beam 1418. Each returned light beam in an array of returning light beams 1440 may correspond to one of the incident light beams in array of light beams 1406. Given the asymmetrical properties of unidirectional mirror or beam splitter 1410, the returned light is reflected in the direction of detection optics 1450 in the body.

The detection optics 1450 may include a polarizer 1452 that has a plane of preferred polarization oriented normal to the plane polarization of polarizer 1403. Alternatively, polarizer 1403 and polarizer 1452 may be omitted in some embodiments. The array of returning light 1440 (e.g., array of returning light beams) may pass through imaging optics 1454 in one embodiment. The imaging optics 1454 may include one or more lenses. Alternatively, the detection optics 1450 may not include imaging optics 1454. In one embodiment, the returning light 1440 further passes through a matrix 1456, which may be an array of pinholes. Alternatively, no matrix 1456 is used in some embodiments. The returning light 1440 is then directed onto a detector 1458 in the body.

The detector 1458 is an image sensor having a matrix of sensing elements each representing a pixel of the image. If a matrix 1456 is used, then each pixel further corresponds to one pinhole of matrix 1456. In one embodiment, the detector is a charge coupled device (CCD) sensor. In one embodiment, the detector is a complementary metal-oxide semiconductor (CMOS) type image sensor. Other types of image sensors may also be used for detector 1458. In one embodiment, the detector 1458 detects light intensity at each pixel.

In one embodiment, detector 1458 provides data to a local server computing device, such as local server computing device 105 of FIG. 1. Thus, each light intensity measured in each of the sensing elements of the detector 1458, is then captured and analyzed.

Intraoral scanner 1400 further includes a control module 1470 in the body connected both to semiconductor laser 1308 and a motor 1472, voice coil or other translation mechanism. In one embodiment, control module 1470 is or includes a field programmable gate array (FPGA) configured to perform control operations. Motor 1472 is linked to focusing optics 1412 for changing a focusing setting of confocal focusing optics 1412. This may adjust the relative location of an imaginary flat or non-flat focal surface of focusing optics 1442 along the Z-axis (e.g., in the imaging axis). Control module 1470 may induce motor 1472 to axially displace (change a location of) one or more lenses of the focusing optics 1412 to change the focal depth of the imaginary flat or non-flat focal surface. In one embodiment, motor 1472 or intraoral scanner 1400 includes an encoder (not shown) that accurately measures a position of one or more lenses of the focusing optics 1412. The encoder may include a sensor paired to a scale that encodes a linear position. The encoder may output a linear position of the one or more lenses of the focusing optics 1412. The encoder may be an optical encoder, a magnetic encoder, an inductive encoder, a capacitive encoder, an eddy current encoder, and so on. After receipt of feedback that the location of the one or more lenses has changed, control module 1470 may induce laser 1308 to generate a light pulse.

Processing logic of the local server computing device may determine the relative intensity in each pixel of a received intraoral scan over the entire range of focal settings of focusing optics 1412 from received intraoral scan data. Once a certain light point associated with a particular pixel is in focus, the measured intensity will be maximal for that pixel. Thus, by determining the Z corresponding to the maximal light intensity or by determining the maximum displacement derivative of the light intensity, for each pixel, the relative position of each light point or spot along the Z axis can be determined for each pixel. Thus, data representative of the three-dimensional pattern of a surface in the teeth segment 1420 or other intraoral object can be obtained.

FIGS. 15A-19B illustrate examples of different wired and/or wireless connection options for a scanner 1500 according to embodiments. In embodiments, the scanner 1500 may correspond to scanner 150 of FIG. 1, scanner 1300 of FIG. 13 and/or scanner 1400 of FIG. 14. Accordingly, the scanner 1500 may include components of scanner 150, scanner 1300 and/or scanner 1400 in addition to the components described with reference to FIGS. 15A-19B.

Scanner 1500 may be designed such that at manufacture time the scanner 1500 can easily be configured and manufactured to accommodate one or more use cases, such as those set forth in FIGS. 15A-19B. A Scanner manufacturing platform may include a wireless communication module 1515, a wired communication module 1518, a controller module 1525, one or more battery module 1522 (e.g., a replaceable battery module and/or an integrated rechargeable battery module), and/or a charging module 1520. A manufacturer may determine a scanner configuration to be manufactured (e.g., for a particular market, for a particular product level, etc.), which may include or exclude one or more of the pre-configured modules. The scanner 1500 may then be manufactured with the appropriate modules according to the scanner configuration.

In some embodiments, the scanner 1500 is manufactured with all modules (e.g., with wireless communication module 1515, wired communication module 1518, controller module 1525, battery module(s) 1522 and charging module 1520). The capabilities of the scanner 1500 may then be controlled via software and/or firmware. For example, the scanner 1500 may be manufactured to support many different use cases and capabilities. However, different scanner capabilities may be associated with different scanner subscription packages. Depending on a subscription package of a user, one or more capabilities of the scanner may be automatically activated or deactivated. At any time, the user may change the subscription package to which they subscribe, and a command may be sent to the scanner 1500 to change software and/or firmware settings that adjust the activated and/or deactivated capabilities of the scanner 1500. For example, a user may elect to use a wired scanner subscription, and wireless communication module 1515 of the scanner may be deactivated. In such a use case, the scanner 1500 would need a wired connection to a computing device to implement scanning. In another example, a user may elect to use wired charging and wireless data. In another example, a user may elect to use a pure wireless scanner. Many other options are also possible, some of which are discussed below.

In some embodiments, scanner 1500 includes wireless communication module 1515, wired communication module 1518, one or more battery module 1522, a charging module 1520 for charging one or more rechargeable battery and/or a controller module 1525 (e.g., a processing device) for controlling one or more functions of the scanner 1500. Wireless communication module 1515 may include a network interface controller (NIC) capable of communicating via Wi-Fi, via third generation (3G), fourth generation (4G) and/or fifth generation (5G) telecommunications protocols (e.g., global system for mobile communications (GSM), long term evolution (LTE), Wi-Max, code division multiple access (CDMA), etc.), via Bluetooth, via Zigbee, and/or via other wireless protocols.

Wired communication module 1518 may include an Ethernet network interface controller (NIC), a universal serial bus (USB) port, a parallel port, a serial port, or other wired port. Wired communication module 1518 may be connected to and/or include a port of scanner 1500. A cable 1505, 1605, 1705, 1805, 1905 may be plugged into the port to provide a wired connection to wired communication module 1518, and through the wired communication module 1518 to the scanner 1500. In one embodiment, cable 1505, 1605, 1705, 1805, 1905 is an easily detachable connector pair that includes power and data lines and that can sustain up to 15000 insertion cycles for charging and can provide USB connectivity.

Battery modules 1522 may include an integrated rechargeable battery module that includes a removable or non-removable rechargeable battery. Battery modules 1522 may additionally or alternatively include a replaceable battery module that can receive non-rechargeable batteries. Accordingly, battery modules 1522 may include just one or more rechargeable batteries, just one or more replaceable batteries, or both one or more rechargeable batteries and one or more replaceable batteries.

Charging module 1520 may include a charger for charging a rechargeable battery in a battery module 1522. The charging module 1520 may include a traditional charger that receives a current via a wired connection (e.g., via a cable 1505, 1605, 1705, 1805, 1905). The charging module 1520 may additionally or alternatively include an inductive or wireless charger component that includes a secondary coil configured to inductively couple with a primary coil of an external wireless charger that is external to the scanner 1500 (e.g., that is integrated into a cradle for the scanner 1500).

Controller module 1525 may include a processing device, memory, and/or other components for controlling one or more operations of scanner 1500. In one embodiment, controller module 1525 includes a system on a chip (SoC) including a processor and memory. In one embodiment, controller module 1525 includes firmware and/or software installed thereon that controls a functionality of scanner 1500.

Figure 15A:
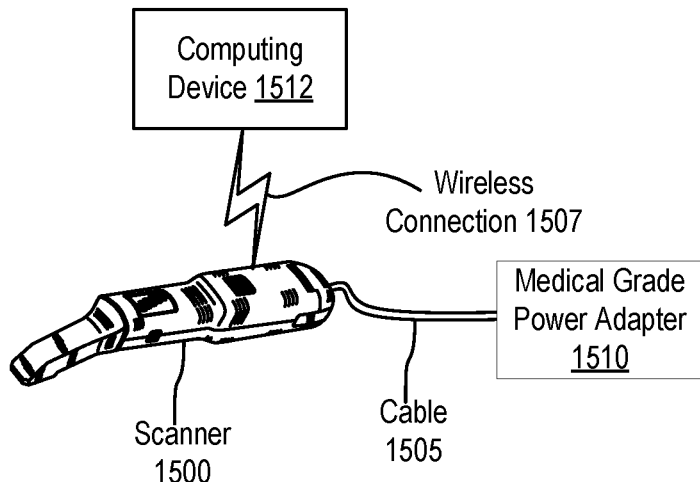
FIGS. 15A-B illustrate a scanner physically connected to a medical grade power adapter via a cable and wirelessly connected to a computing device via a wireless connection.
Figure 15B:
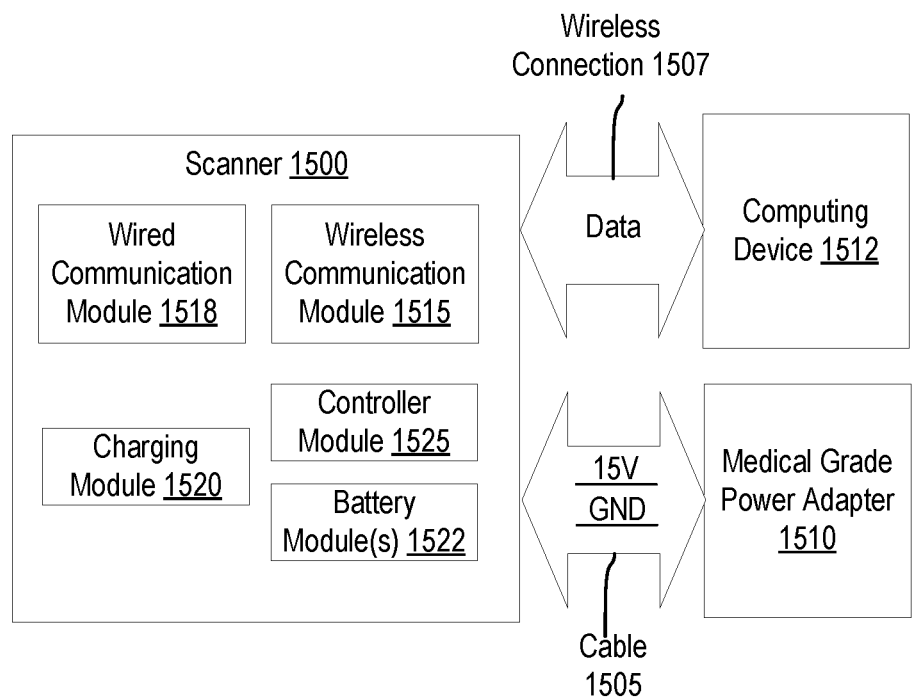

FIGS. 15A-B illustrate a scanner 1500 physically connected to a medical grade power adapter 1510 via a cable 1505 and wirelessly connected to a computing device 1512 via a wireless connection 1507. Computing device 1512 may be, for example, local server computing device 105 of FIGS. 1A-2 and/or local server computing device 700 of FIGS. 7A-C.

Power supplies designed for use with medical and healthcare equipment need to conform to the internationally recognized safety standard IEC 60601-1-2:2015. This standard defines the safety criteria and specifications for any item of equipment connected to a main power supply used to monitor, diagnose and treat a patient. In particular, the standard covers applications where the patient is physically attached to the equipment. Accordingly, for scanner 1500 to be provided with power during use on a patient, the power supply providing power to the scanner 1500 should satisfy strict safety criteria (e.g., comply with IEC 60601). Medical grade power adapter 1510 satisfies appropriate safety criteria (e.g., complies with IEC 60601). Accordingly, medical grade power adapter 1510 provides power (e.g., via a 15V wire and a ground wire) to scanner 1500 via cable 1505 during use, which may be used to power scanner 1500 and/or to recharge any rechargeable batteries in battery module 1522.

Data transfer between scanner 1500 and computing device 1512 (which may run an intraoral scan application as discussed above) may be performed via wireless connection 1507.

Figure 16A:
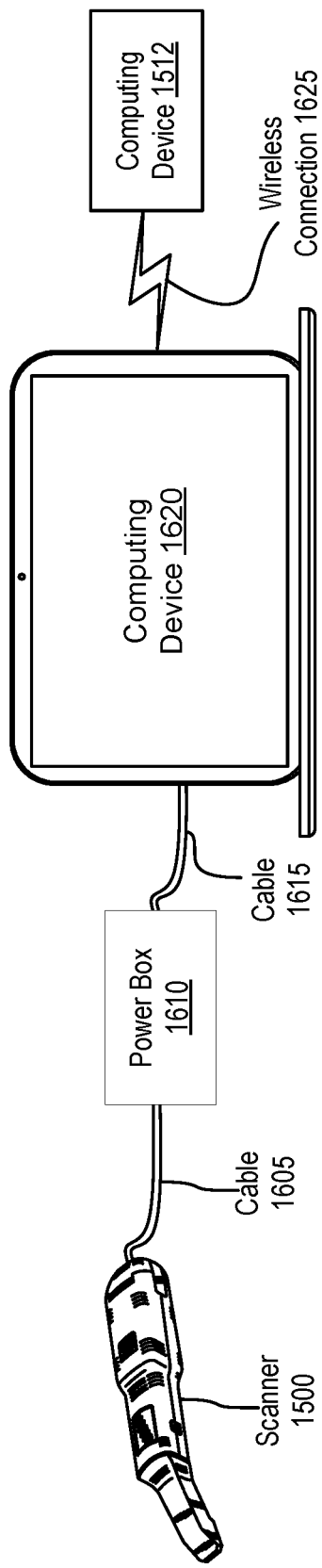
FIGS. 16A-B illustrate scanner physically connected to a power box via a cable.
Figure 16B:
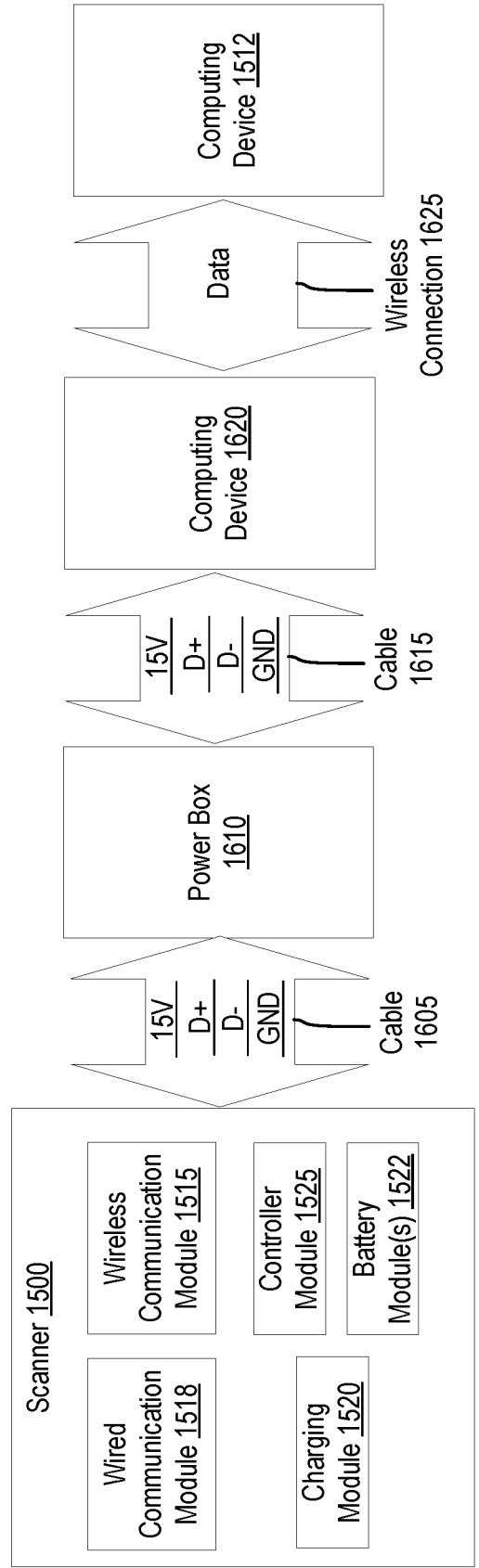

FIGS. 16A-B illustrate scanner 1500 physically connected to a power box 1610 via a cable 1605. Power box 1610 may include a medical grade power adapter that applies isolated power to scanner 1500 and that complies with appropriate safety criteria (e.g., complies with IEC 60601). Power box 1610 may connect to a power source via a cable (not shown) and to a computing device 1620 via cable 1615, which may be a stationary or mobile computing device. In one embodiment, computing device 1620 corresponds to computing device 152 or 154 of FIG. 1A. In one embodiment, computing device 1620 is a standard (e.g., off-the-shelf) laptop or tablet computer. Computing device 1620 may then be wirelessly connected to computing device 1512 via a wireless connection 1625.

Power box 1610 provides power (e.g., via a 15V wire and a ground wire) to scanner 1500 via cable 1605 during use, which may be used to power scanner 1500 and/or to recharge any rechargeable batteries in battery module 1522. Power box 1610 may additionally provide power to computing device 1620. Alternatively, a different power source may be provided for computing device 1620. Power box 1610 may additionally provide wired data transfer between scanner 1500 and computing device 1620 via cables 1605, 1615. Alternatively, or additionally, scanner 1500 may have a wireless connection to computing device 1512, and may exchange data with computing device 1512 via the wireless connection.

Computing device 1620 may run an intraoral scan application that processes scans generated by scanner 1500 in embodiments. In such embodiments, computing device 1620 may not be connected to computing device 1512. Alternatively, computing device 1620 may be connected to computing device 1512 via wireless connection 1625, and may perform data transfer with computing device 1512 via the wireless connection 1625.

In the embodiment shown in FIGS. 16A-B, the scanner 1500 may lack a wireless communication module 1515, or may have a deactivated wireless communication module 1515, and may instead rely on the wireless communication capabilities of computing device 1620 for communicating with computing device 1512.

Figure 17A:
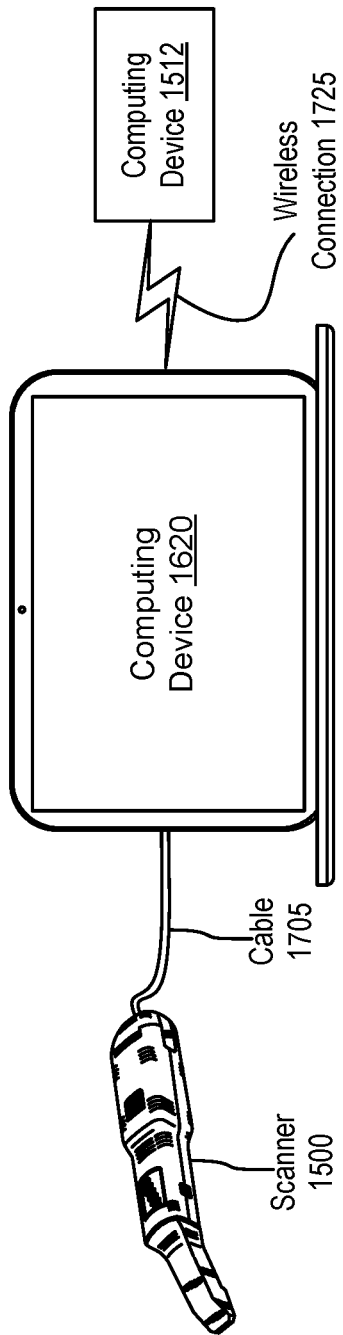
FIGS. 17A-B illustrate scanner physically connected to a computing device via a cable.
Figure 17B:
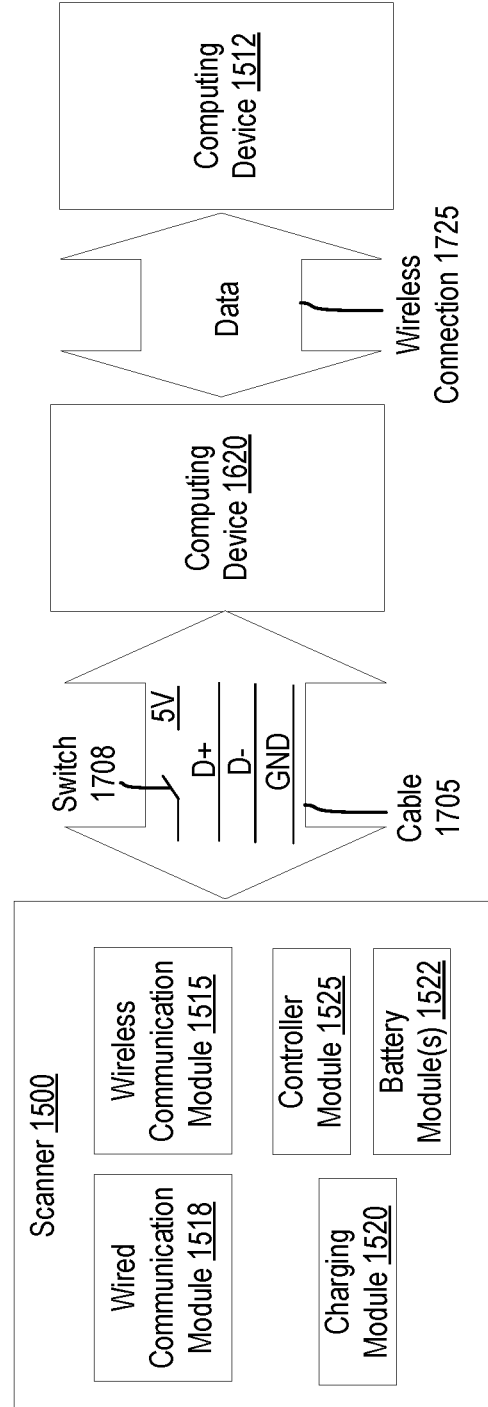

FIGS. 17A-B illustrate scanner 1500 physically connected to a computing device 1620 via a cable 1705. Computing device 1620 may be wirelessly connected to computing device 1512 via a wireless connection 1725. Alternatively, or additionally, scanner 1500 may have a wireless connection to computing device 1512, and may exchange data with computing device 1512 via the wireless connection. The cable 1705 that connects scanner 1500 to computing device 1620 may be, for example, a USB cable that plugs into a USB port of computing device 1620. Data may be transferred via cable 1705 according to the USB 2.0 protocol or another USB protocol, for example. Computing device 1620 may provide power to scanner 1500 via cable 1705. However, the supplied power may be a lesser voltage than a voltage supplied by medical grade power adapter 1510 of FIGS. 15A-B or power box 1610 of FIGS. 16A-B. For example, medical grade power adapter 1510 and power box 1610 may provide 15V via cable 1505, 1605 in one embodiment, and computing device 1620 may provide 5V via cable 1705 in one embodiment. In embodiments, the power provided to scanner 1500 by computing device 1620 does not satisfy medical power requirements (e.g., does not comply with IEC 60601). Accordingly, it may be impermissible for computing device 1620 to provide power to scanner 1500 while scanner is in use on a patient. However, while scanner 1500 is not in use, power may be provided to scanner 1500 from computing device 1620.

In one embodiment, cable 1705 is a special cable that includes an integrated switch 1708 that opens under certain circumstances and that closes under other circumstances. Alternatively, switch 1708 may be integrated into scanner 1500 rather than into cable 1705. The switch 1708 may be configured to open while the scanner 1500 is in use and to close while the scanner 1500 is idle or not in use. While the switch 1708 is open, no power is supplied to scanner 1500. However, data transfer (e.g., via data lines D+ and D−) is still possible between scanner 1500 and computing device 1620 while the switch 1708 is open. Accordingly, while scanner 1500 is in use, it draws on power from batteries from one or more battery modules 1522. While the switch is closed, power is supplied to scanner 1500, and charging module 1520 uses the power to charge rechargeable batteries of battery module 1522. Accordingly, switch 1708 enables scanner to be charged by computing device 1620 while still complying with appropriate standards for powering medical devices.

In one embodiment, switch 1708 is a magnetic switch, such as a reed switch. Switch 1708 may close when it is subject to a magnetic field, and may open when not subject to the magnetic field. In one embodiment, a cradle for scanner 1500 includes one or more magnets (e.g., permanent magnets and/or electromagnets) that generate a magnetic field that causes the switch 1708 to close while the scanner 1500 is in the cradle. When the scanner 1500 is removed from the cradle, the switch 1708 is no longer subject to the magnetic field produced by the one or more magnets of the cradle, and the switch 1708 opens. Thus, in embodiments scanner 1500 is charged while it is in the cradle, and is not charged while it is away from the cradle.

In other embodiments, switch 1708 may be any other type of switch, such as a momentary switch that receives a signal or command to switch while scanner 1500 is in the cradle, and does not receive such a signal or command when the scanner 1500 is not in the cradle. For example, scanner 1500 may include an accelerometer, gyroscope and/or other motion sensor that may be used to detect when the scanner 1500 is in the cradle. In another example, the cradle may transmit a wireless signal, as described above, and scanner 1500 may determine when it is in close proximity to the cradle based on the wireless signal. Scanner 1500 may then send a switch signal to switch 1708 when it is detected to be in the cradle or in close proximity to the cradle.

In some embodiments, hardware detection is performed to determine whether scanner 1500 is not in use (and can thus receive power), such as via switch 1708. In some embodiments, software detection is performed to determine whether scanner 1500 is not in use. Such software detection may include receiving data from motion sensors and using the data to determine that the scanner 1500 is not in use (e.g., because the scanner has been motionless for a threshold amount of time). Software detection may additionally or alternatively include generating scan data and/or image data, and processing the scan data and/or image data to determine whether a probe of the scanner 1500 is in an oral cavity of a patient (e.g., via application of machine learning and/or image processing). If the probe is not in an oral cavity, controller module 1525 may determine that scanner 1500 is not under use.

In some embodiments, both hardware detection and software detection are performed to determine whether scanner 1500 is in use. In such embodiments, power may be supplied to scanner 1500 if both the hardware detection and the software detection indicate that the scanner 1500 is not in use. However, if either the hardware detection or the software detection indicate that the scanner is in use, power may not be supplied to the scanner 1500. For example, in an embodiment, scanner 1500 is only provided power if switch 1708 is closed and a motion sensor of scanner 1500 fails to detect any motion (or detects motion that is below a motion threshold).

Computing device 1620 may run an intraoral scan application that processes scans generated by scanner 1500 in embodiments. In such embodiments, computing device 1620 may not be connected to computing device 1512. Alternatively, computing device 1620 may be connected to computing device 1512 via wireless connection 1625, or scanner 1500 may have a wireless connection to computing device 1512, and may perform data transfer with computing device 1512 via the wireless connection (e.g., wireless connection 1625).

In the embodiment shown in FIGS. 17A-B, the scanner 1500 may lack a wireless communication module 1515, or may have a deactivated wireless communication module 1515, and may instead rely on the wireless communication capabilities of computing device 1620 for communicating with computing device 1512.

Figure 18A:
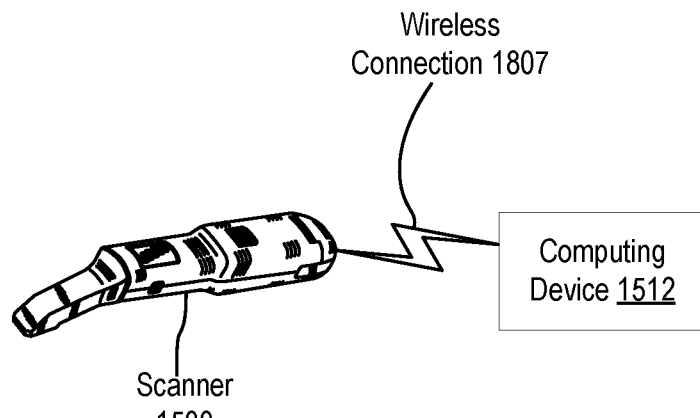
FIGS. 18A-B illustrate a scanner wirelessly connected to a computing device via a wireless connection.
Figure 18B:
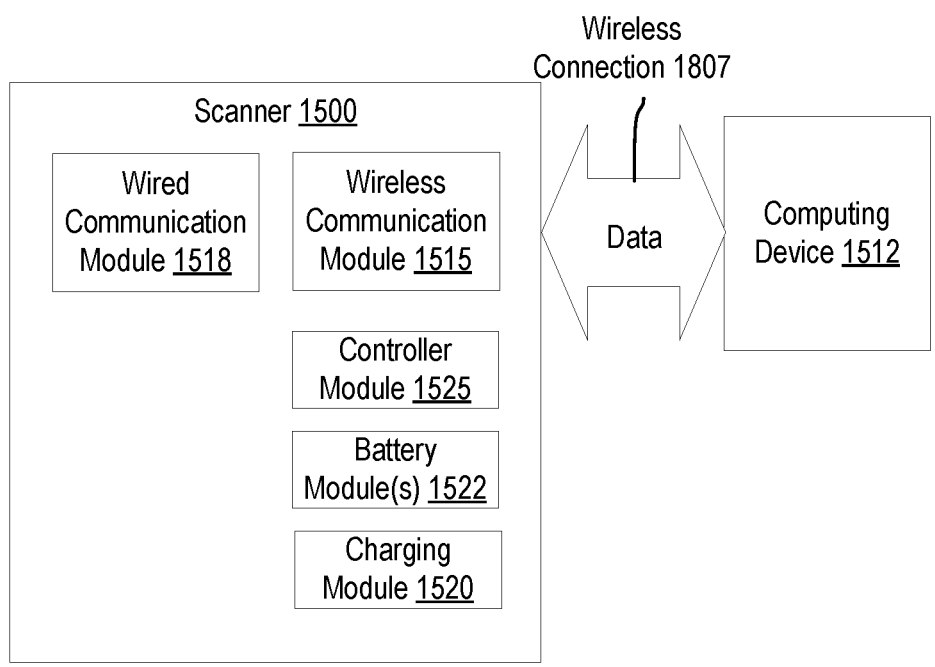

FIGS. 18A-B illustrate a scanner 1500 wirelessly connected to a computing device 1512 via a wireless connection 1807. Scanner 1500 is not physically connected (e.g., via a cable) to any computing device or power supply. Accordingly, scanner 1500 operates in a fully wireless mode of operation, and draws on power from onboard batteries of battery module 1522, and exchanges data with computing device 1512 via wireless connection 1807.

Figure 19A:
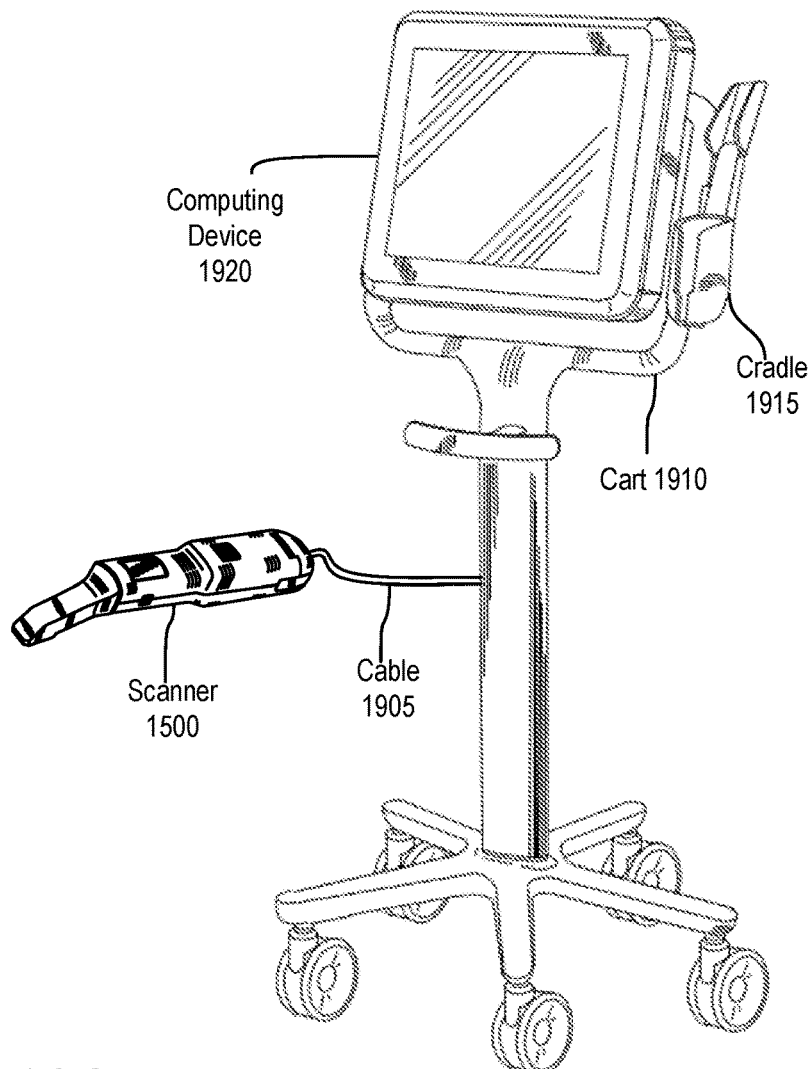
FIGS. 19A-B illustrate a scanner physically connected to a scanner cart via a cable.
Figure 19B:
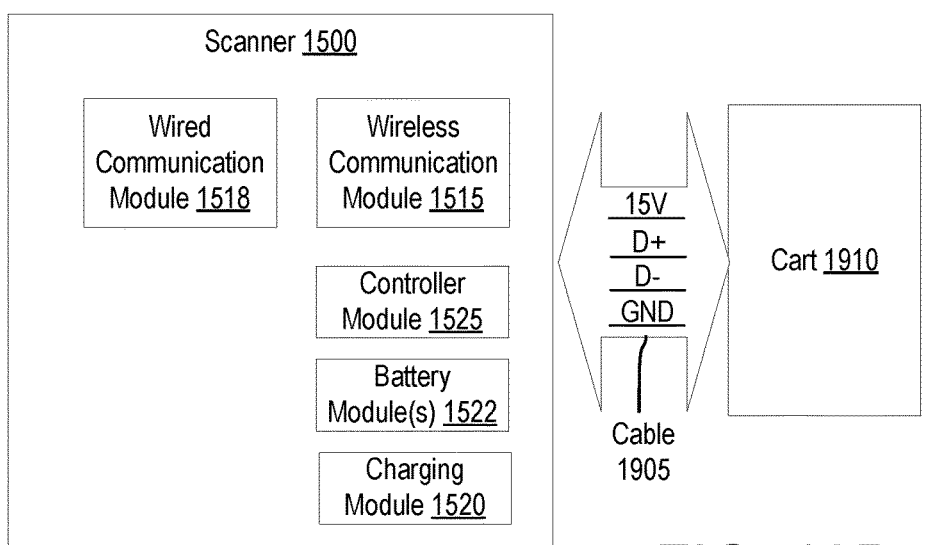

FIGS. 19A-B illustrate a scanner 1500 physically connected to a scanner cart 1910 via a cable 1905. Cart 1910 may include an onboard medical grade power adapter (not shown), and may 1510 provide power (e.g., via a 15V wire and a ground wire) to scanner 1500 via cable 1905 during use, which may be used to power scanner 1500 and/or to recharge any rechargeable batteries in battery module 1522. Cart 1910 may further include an onboard cradle 1915 for holding the scanner 1500 when scanner 1500 is not in use. Additionally, cart 1910 may include a computing device 1920 that may run a scan application for processing scans from scanner 1500. Scanner 1500 may perform data transfer with cart 1910 via cable 1905. In some embodiments, cart 1910 is wirelessly connected to a computing device (e.g., location server computing device 105 of FIGS. 1A-2). Alternatively, or additionally, scanner 1500 may have a wireless connection to computing device 1512, and may exchange data with computing device 1512 via the wireless connection.

As shown in FIGS. 15A-19B, scanner 1500 may be used in multiple different environments and/or configurations, each with different types of wired and/or wireless connections. In some embodiments, controller module 1525 controls which of the types of scanner configurations may be used (e.g., based on a subscription associated with scanner 1500). In some embodiments, controller module 1525 automatically detects a type of configuration to use, such as by detecting whether a cable is connected to scanner 1500, detecting a type of power being provided to scanner (e.g., a supplied voltage, a supplied current, etc.), detecting whether cable data transfer is possible via a cable connected to scanner 1500 (e.g., detecting whether data lines are present in a connected cable), detecting whether scanner 1500 has wireless connections to a computing device 1512, and so on. Controller module 1525 may then automatically set a configuration based on the detected parameters. In one embodiment, if no cable is connected to scanner 1500, scanner is configured in a fully wireless configuration, as shown in FIGS. 18A-B. In one embodiment, if a wired connection that provides power that fails to satisfy medical power requirements is detected and a wired data connection is detected, scanner is configured to operate in the mode shown in FIGS. 17A-B. In one embodiment, if a wired connection that provides power that satisfies medical power requirements is detected and a wired data connection is detected, scanner 1500 is configured to operate in the mode shown in FIGS. 16A-B or the mode shown in FIGS. 19A-B. In one embodiment, if a wired connection that provides power that satisfies medical power requirements is detected and a wireless data connection is detected, scanner 1500 is configured to operate in the mode shown in FIGS. 15A-B.

In one embodiment, a user selects which type of configuration they plan on using rather than the configuration being automatically detected. For example, the user may select the configuration type via a touchscreen interface of the scanner 1500 or via a graphical user interface provided via computing device 1620. In one embodiment, scanner 1500 includes a ranked list of modes of operation. Scanner 1500 may determine which of the modes of operation are appropriate (e.g., based on a wireless connection and/or wired connection), and automatically select a highest ranked option from the modes of operation that are appropriate. Alternatively, scanner 1500 may output an indication of those modes of operation that are appropriate, or of a highest ranked mode of operation that is among the determined appropriate modes of operation. A user may then select to use the scanner 1500 according to the highest ranked mode of operation or one of the other appropriate modes of operation (e.g., by plugging the scanner into a computing device 1620, medical grade power adapter 1510, power box 1610, etc. as appropriate).

In one embodiment, scanner 1500 (e.g., controller module 1525) includes a network analyzer, which may be implemented, for example, in hardware, firmware and/or software. Alternatively, or additionally, computing device 1620 and/or computing device 1512 may include a network analyzer. The network analyzer periodically or continuously monitors a network environment of the scanner 1500, computing device 1512 and/or computing device 1620 to determine whether the network environment is sufficient to support wireless scanning for one or more scanners. In embodiments, scanner 1500 or computing device 1620 analyzes wireless network traffic (e.g., of a Wi-Fi network or other wireless network) to determine signal strength, lag, delay, data transfer rate, number of occupied channels (e.g., in a 5 GHz to 6 GHz range, or in another frequency range), pattern of use of channels and/or other signal and/or message properties for the wireless network. In some embodiments, each scanner 1500 on a wireless network may use a channel width of 40 Mhz, 80 Mhz or 160 Mhz. Alternatively, other channel widths may be used. In embodiments, each scanner 1500 automatically selects a best channel to use (e.g., a channel that is unused by scanners or a channel that has highest bandwidth, lowest lag, highest strength, highest transfer speeds, etc.). The network analyzer may additionally determine a number of scanners connected to the network, channels occupied by scanners, and/or an amount of data (e.g., scan data) being transmitted by the scanners and/or computing devices 1620 to computing device 1512 over the wireless network in some embodiments. The network analyzer may determine a data transfer threshold and/or wireless connection criteria based on the analyzed conditions of the network (e.g., based on signal strength, lag, delay, etc.). Alternatively, a data transfer threshold and/or wireless connection criteria may be preconfigured.

The network analyzer may determine whether the wireless network satisfies one or more wireless scanning criteria based on the analyzed network traffic. For example, the network analyzer may determine whether a determined data transfer value (e.g., that would be used if an additional scanner were to be added to the network) exceeds a data transfer threshold (and thus fails to satisfy the wireless scanning criteria), whether any unused channels are present, whether a number of scanners on the network exceeds a threshold, etc. The network analyzer may then generate an output recommending that a wired connection be used or that the wireless network be updated to accommodate wireless scanning with the scanner 1500 if one or more wireless scanning criteria are not satisfied. In one embodiment, the wireless network supports simultaneous operation of up to five scanners 1500. In some embodiments, the network analyzer outputs a recommendation of a maximum number of scanners that can be operated in parallel given the analyzed wireless network. For example, each scanner may have a known average bandwidth usage. A total bandwidth of the network may be determined, and the total bandwidth may be divided by the average bandwidth usage of scanners to determine a number of scanners supports by the network. Recommendations may be output via a touchscreen of scanner 1500 or via a graphical user interface of computing device 1620.

In one embodiment, an intraoral scanning system includes an intraoral scanner that includes a rechargeable battery, a charging module, a wireless communication module, a wired communication module, and a port connected to the wired communication module and the charging module. The intraoral scanning system further includes a cable coupled to the port, wherein the cable is to provide power to the charging module while the intraoral scanner is not in use. The cable may further connect to a computing device, such as a mobile computing device or a desktop computing device that provides power to the intraoral scanner, where the provided power is not medical grade power. The intraoral scanner and/or the cable detects when the intraoral scanner is in use, and prevents the cable from supplying power to the charging module while the intraoral scanner is in use. The intraoral scanner and/or cable further detects when the intraoral scanner is not in use, and provides power to the intraoral scanner while it is not in use. The intraoral scanner may have a wireless connection to another computing device (e.g., a local server computing device), and may perform wireless data transmission to/from the additional computing device via the wireless connection. Additionally, or alternatively, the intraoral scanner may perform wired data transmission with the computing device connected to the cable.

In one embodiment, the intraoral scanning system additionally includes a cradle that may hold the intraoral scanner while it is not in use. The intraoral scanner and/or the cable may detect when the intraoral scanner is in the cradle, and may enable the cable to supply power to the charging module while the intraoral scanner is in the cradle. In one embodiment, at least one of the intraoral scanning system or the cable includes a switch that has a closed state while the intraoral scanner is in the cradle and an open state while the intraoral scanner is removed from the cradle. In one embodiment, the switch is a magnetic switch, the cradle comprises one or more magnets that provide a magnetic field, and the magnetic field causes the magnetic switch to have the closed state while the intraoral scanner is in the cradle. In one embodiment, the intraoral scanner comprises one or more image sensor to generate at least one of intraoral scans or two-dimensional images of a field of view of the scanner and a motion sensor to detect a motion state of the intraoral scanner. The intraoral scanner may further include a controller to determine whether the intraoral scanner is in use based on an analysis of at least one of the intraoral scans, the two-dimensional images, or the motion state. If either the controller determines that the scanner is in use (via software detection) or the switch indicates that the scanner is in use, then power may not be provided to the scanner.

Figure 20:
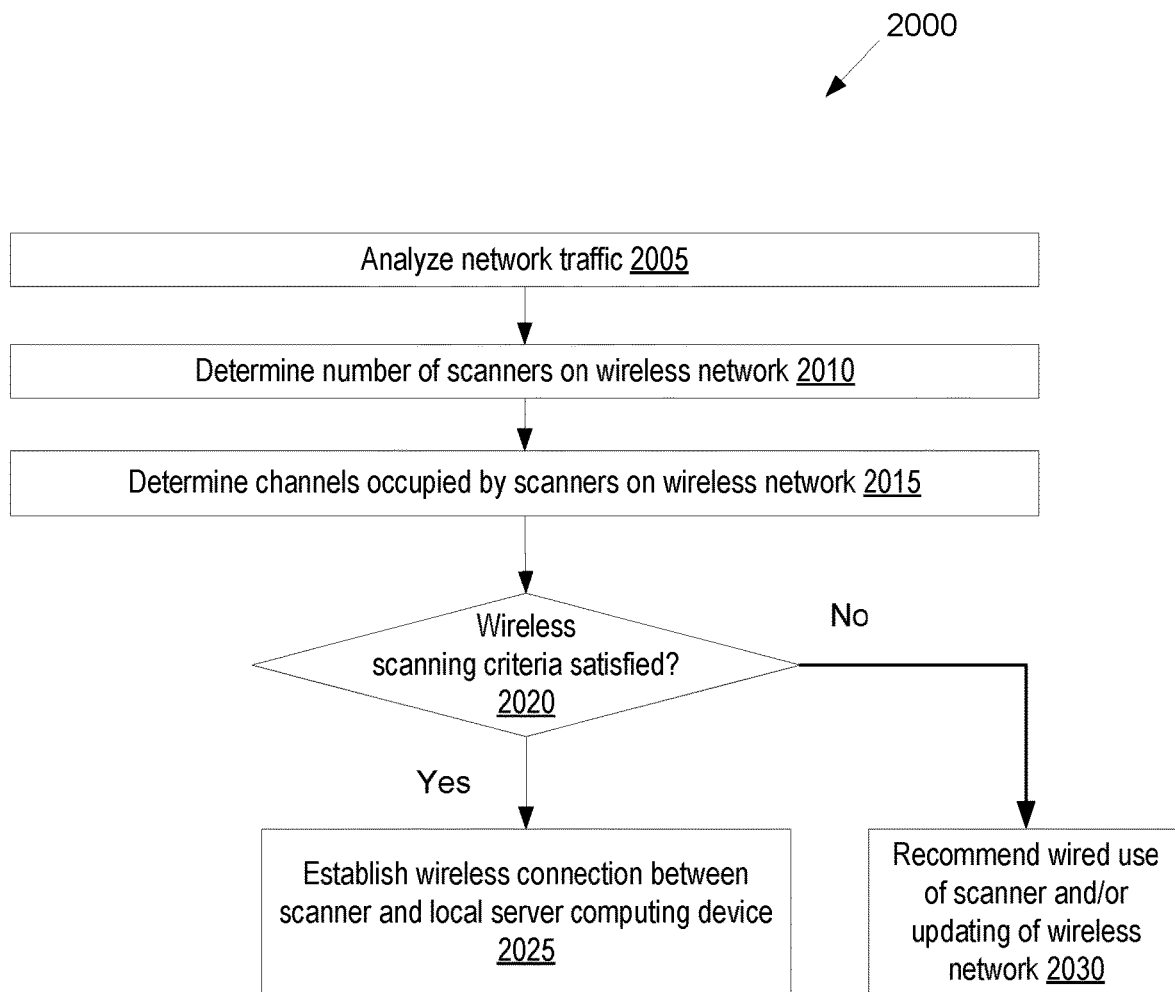
FIG. 20 illustrates a flow diagram for a method of analyzing a wireless network and determining whether it is appropriate to use a scanner in a wireless scanning mode on the wireless network, in accordance with an embodiment.

FIG. 20 illustrates a flow diagram for a method 2000 of analyzing a wireless network and determining whether it is appropriate to use a scanner in a wireless scanning mode on the wireless network, in accordance with an embodiment. Operations of method 2000 may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the method 2000 are performed by a local server computing device, by a mobile computing device and/or by a scanner.

For simplicity of explanation, method 2000 is depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

At block 2005 of method 2000, processing logic analyzes network traffic. This may include determining signal strength, lag, delay, data transfer rate, number of occupied Wi-Fi channels (e.g., in a 5 GHz to 6 GHz range), pattern of use of channels and/or other signal and/or message properties for the wireless network. In one embodiment, at block 2010 processing logic determines a number of scanners on the wireless network. In one embodiment, at block 2015 processing logic determines which channels (e.g., in a 5 Ghz to 6 Ghz range) are under use by scanners.

At block 2020, processing logic determines whether the wireless network satisfies one or more wireless scanning criteria. In one embodiment, processing logic determines a number of concurrent scanners that can be supported by the wireless network based on the analysis of the network traffic. Wireless scanning criteria may then be satisfied if a total number of scanners on the wireless network is at or below the determined number of concurrent scanners supported by the wireless network. Other criteria may also be used, as discussed above. If the wireless scanning criteria are satisfied, the method continues to block 2025, and wireless connections may be established between one or more scanners and a local server computing device. Alternatively, the connections may already have been established. If one or more wireless scanning criteria are not satisfied, the method continues to block 2030, and processing logic may output a recommendation for wired use of one or more scanners and/or a recommendation to update the wireless network (e.g., by adding access points, removing access points, relocating access points, etc.).

In one embodiment, an intraoral scanning system includes a first number of intraoral scanners and a computing device (e.g., local server computing device 150 of FIGS. 1A-2). The computing device wirelessly connects to the first number of intraoral scanners via a wireless network. The computing device and/or one or more of the first number of intraoral scanners monitors conditions of the wireless network. The computing device and/or one or more of the first number of intraoral scanners determines a second number of intraoral scanners supported by the wireless network according to the conditions of the wireless network, determines whether the first number of intraoral scanners is equal to or less than the second number of intraoral scanners, and may output a notice based on whether the first number of intraoral scanners is equal to or less than the second number of intraoral scanners.

In one embodiment, at least one of first computing device or one or more intraoral scanners determines that the first number of intraoral scanners exceeds the second number of intraoral scanners, and outputs a recommendation to use one or more intraoral scanners in a wired configuration and/or a recommendation to update the wireless network so that the wireless network will support more intraoral scanners.

In one embodiment, at least one of first computing device or one or more intraoral scanners is determines that the first number of intraoral scanners is equal to or less than the second number of intraoral scanners, and either does not output a notice or outputs an indication that the wireless network is sufficient to accommodate the first number of intraoral scanners.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
   receiving, by a client computing device, a user input to associate the client computing device with a first intraoral scanner of a plurality of intraoral scanners, the user input comprising an identifier of the first intraoral scanner;
   wirelessly connecting the client computing device with a local server computing device; and
   sending the identifier of the first intraoral scanner to the local server computing device, wherein the local server computing device wirelessly connects to the first intraoral scanner and associates the client computing device with the first intraoral scanner;
   wherein once the client computing device and the first intraoral scanner are both wirelessly connected to the local server computing device and associated with one another, intraoral scan data generated by the first intraoral scanner is sent to the local server computing device, the intraoral scan data is processed by the local server computing device to generate a three-dimensional surface of a dental site, the three-dimensional surface or a view of the three-dimensional surface of the dental site is sent to the client computing device, and the three-dimensional surface or the view of the three-dimensional surface of the dental site is displayed by the client computing device.

2. The method of claim 1, further comprising:
   determining, by the client computing device, an available compute unit from a plurality of compute units of the local server computing device, wherein wirelessly connecting the client computing device with the local server computing device comprises wirelessly connecting the client computing device to the available compute unit of the local server computing device.

3. The method of claim 1, further comprising:
   receiving, by the client computing device or by the first intraoral scanner, an identifier of a first display device;
   sending, by the client computing device or by the first intraoral scanner, the identifier of the first display device to the local server computing device, wherein the local server computing device wirelessly connects to the first display device and associates the first display device with the client computing device and the first intraoral scanner, and wherein the view of the three-dimensional surface of the dental site is additionally sent to the first display device and displayed by the first display device.

4. The method of claim 3, wherein the identifier of the first display device comprises a code, wherein the first display device displays the code, and wherein receiving the identifier of the first display device by the first intraoral scanner comprises scanning the code by the first intraoral scanner.

5. The method of claim 4, wherein the code comprises a one-dimensional barcode or a two-dimensional barcode.

6. The method of claim 3, wherein the first intraoral scanner comprises a touchscreen, the method further comprising:
   outputting a touch keypad on the touchscreen of the first intraoral scanner;
   wherein receiving the identifier of the first display device by the first intraoral scanner comprises receiving the identifier of the first display device via the touch keypad.

7. The method of claim 1, further comprising:
   receiving a user command to disconnect the client computing device and the first intraoral scanner from the local server computing device;
   wirelessly sending a disconnect instruction from the client computing device to the local server computing device;
   receiving a disconnect confirmation by the client computing device from the local server computing device; and
   displaying the disconnect confirmation on at least one of the display of the client computing device or a touchscreen of the first intraoral scanner.

8. An intraoral scanning system, comprising:
   a first intraoral scanner configured to generate intraoral scan data;
   a client computing device configured to remotely control an intraoral scan application that executes on a local server computing device; and
   the local server computing device, configured to execute the intraoral scan application, wherein the local server computing device is further configured to:
      receive a first connection request from the client computing device;
      wirelessly connect to the client computing device;
      receive an identifier of the first intraoral scanner from the client computing device responsive to the client computing device receiving a user input to associate the client computing device with the first intraoral scanner;
      wirelessly connect to the first intraoral scanner using the identifier; and
      associate the first intraoral scanner with the client computing device.

9. The intraoral scanning system of claim 8, wherein once the client computing device is associated with the first intraoral scanner and the first intraoral scanner and client computing device are both wirelessly connected to the local server computing device:
   the first intraoral scanner is to send the intraoral scan data to the local server computing device;
   the intraoral scan application of the local server computing device is to process the intraoral scan data to generate or update a three-dimensional surface of a dental site and send a view of the three-dimensional surface to the client computing device; and
   the client computing device is to output the view of the three-dimensional surface of the dental site to a display of the client computing device.

10. The intraoral scanning system of claim 8, wherein the client computing device is one of a plurality of peripheral computing devices of the intraoral scanning system, and wherein the first intraoral scanner is one of a plurality of intraoral scanners of the intraoral scanning system, the intraoral scanning system further comprising:
   a second intraoral scanner of the plurality of intraoral scanners; and
   a second client computing device of the plurality of peripheral computing devices;
   wherein the local server computing device is further to:
      receive a second connection request from the second client computing device;
      wirelessly connect to the second client computing device;
      receive a second identifier of the second intraoral scanner from the second client computing device;
      wirelessly connect to the second intraoral scanner using the second identifier; and
      associate the second intraoral scanner with the second client computing device.

11. The intraoral scanning system of claim 10, wherein the local server computing device comprises a plurality of compute units, wherein the client computing device and the first intraoral scanner are to connect to a first available compute unit of the plurality of compute units, and wherein the second client computing device and the second intraoral scanner are to connect to a second available compute unit of the plurality of compute units.

12. The intraoral scanning system of claim 8, wherein the local server computing device comprises a plurality of compute units, and wherein the client computing device is to:
   determine an available compute unit of the plurality of compute units; and
   wirelessly connect to the available compute unit.

13. The intraoral scanning system of claim 8, further comprising:
   a display device;
   wherein the display device is to display an identifier of the display device;
   wherein the client computing device or the first intraoral scanner is to receive the identifier of the display device and send the identifier of the display device to the local server computing device; and
   wherein the local server computing device is to wirelessly connect to the display device using the identifier and associate the display device with the client computing device and the first intraoral scanner.

14. The intraoral scanning system of claim 13, wherein:
   the first intraoral scanner comprises a touchscreen that is to output a touch keypad; and
   the first intraoral scanner is to receive user input of the identifier of the display device via the touch keypad, wherein the identifier comprises a code.

15. The intraoral scanning system of claim 13, wherein once the client computing device, the first intraoral scanner and the display device are associated with one another and wirelessly connected to the local server computing device:
   the first intraoral scanner is to send the intraoral scan data to the local server computing device;

the intraoral scan application of the local server computing device is to process the intraoral scan data to generate or update a three-dimensional surface of a dental site and send a view of the three-dimensional surface to the client computing device and to the display device;

the client computing device is to output the view of the three-dimensional surface of the dental site to a display of the client computing device; and the display device is to output the view of the three-dimensional surface of the dental site.

16. The intraoral scanning system of claim 13, wherein the first intraoral scanner is to scan the identifier and send the identifier to the local server computing device.

17. The intraoral scanning system of claim 16, wherein the identifier comprises a one-dimensional barcode or a two-dimensional barcode.

18. The intraoral scanning system of claim 8, wherein:

the first intraoral scanner comprises a touchscreen configured to output a plurality of virtual buttons and detect a touch input associated with a virtual button of the plurality of virtual buttons; and the first intraoral scanner is configured to provide a signal associated with the touch input of the virtual button to the local server computing device.

19. The intraoral scanning system of claim 18, wherein the plurality of virtual buttons output by the first intraoral scanner is based on a current mode of the intraoral scan application.

20. The intraoral scanning system of claim 19, wherein the first intraoral scanner is to: receive an input from the local server computing device indicating the current mode of an intraoral scan application; and determine the plurality of virtual buttons to output on the touchscreen based at least in part on the current mode of the intraoral scan application.

21. The intraoral scanning system of claim 19, wherein while the current mode is a scanning mode, the plurality of virtual buttons output by the touchscreen comprise at least one of a next segment button or a previous segment button.

22. The intraoral scanning system of claim 19, wherein while the current mode is a scanning mode, the plurality of virtual buttons output by the touchscreen comprise a lower dental arch segment button, an upper dental arch segment button, and a bite segment button.

23. The intraoral scanning system of claim 19, wherein while the current mode is a three-dimensional surface viewing mode, the plurality of virtual buttons comprise a rotate button, a pan button, and a zoom button.

24. The intraoral scanning system of claim 18, wherein the touchscreen is to output one or more message button responsive to receipt of a confirmation request message from the local server computing device, wherein the one or more message button comprises at least one of a confirm button or a cancel button.

25. The intraoral scanning system of claim 8, wherein:

the first intraoral scanner comprises a touchscreen that is configured to display the identifier of the first intraoral scanner.

* * * * *